United States Patent
Shimizu et al.

(10) Patent No.: US 10,633,322 B2
(45) Date of Patent: *Apr. 28, 2020

(54) PROCESS FOR PRODUCING ACETIC ACID

(71) Applicant: Daicel Corporation, Osaka-shi, Osaka (JP)

(72) Inventors: Masahiko Shimizu, Himeji (JP); Yoshihisa Mizutani, Himeji (JP); Hiroyuki Miura, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,535

(22) Filed: Feb. 1, 2019

(65) Prior Publication Data

US 2019/0263744 A1 Aug. 29, 2019

Related U.S. Application Data

(63) Continuation of application No. 15/577,524, filed as application No. PCT/JP2017/041447 on Nov. 17, 2017, now Pat. No. 10,246,399.

(30) Foreign Application Priority Data

Feb. 7, 2017 (JP) ................ 2017-020775
May 29, 2017 (JP) ................ 2017-105771

(51) Int. Cl.
| | | |
|---|---|---|
| *C07C 51/00* | (2006.01) | |
| *B01J 27/00* | (2006.01) | |
| *C07C 51/44* | (2006.01) | |
| *C07C 51/12* | (2006.01) | |
| *B01D 15/36* | (2006.01) | |
| *B01J 27/08* | (2006.01) | |
| *B01D 3/14* | (2006.01) | |
| *B01J 31/02* | (2006.01) | |
| *C07C 51/47* | (2006.01) | |

(52) U.S. Cl.
CPC ............ *C07C 51/44* (2013.01); *B01D 3/143* (2013.01); *B01D 15/361* (2013.01); *B01J 27/08* (2013.01); *B01J 31/0231* (2013.01); *C07C 51/12* (2013.01); *C07C 51/47* (2013.01)

(58) Field of Classification Search
CPC ......... C07C 51/12; C07C 51/44; B01D 3/143; B01D 15/361
See application file for complete search history.

(56) References Cited

U.S. PATENT DOCUMENTS

| | | |
|---|---|---|
| 5,880,311 A | 3/1999 | Uemura et al. |
| 6,080,373 A | 6/2000 | Uemura et al. |
| 2009/0036710 A1 | 2/2009 | Miura et al. |
| 2013/0264186 A1 | 10/2013 | Shimizu et al. |

FOREIGN PATENT DOCUMENTS

| | | |
|---|---|---|
| JP | 8-231463 A | 9/1996 |
| JP | 2007-526310 A | 9/2007 |
| JP | 2009-501129 A | 1/2009 |
| WO | WO 2005/085166 A1 | 9/2005 |
| WO | WO 2012/086386 A1 | 6/2012 |

OTHER PUBLICATIONS

Database WPI Week 198510, Thomas Scientific, London, GB; AN 1985-061373, XP002787605, 1985, 2 pages.
English translation of International Search Report dated Mar. 29, 2018, in PCT International Application No. PCT/JP2017/041447.
English translation of Written Opinion dated Mar. 13, 2018, in PCT International Application No. PCT/JP2017/041447.
Extended European Search Report, dated Jan. 14, 2019, for European Application No. 17825355.5.
International Search Report dated Dec. 26, 2017, in PCT International Application No. PCT/JP2017/041447.

*Primary Examiner* — Sikarl A Witherspoon
(74) *Attorney, Agent, or Firm* — Birch, Stewart, Kolasch & Birch, LLP

(57) ABSTRACT

A process for producing acetic acid comprises a process comprising: (1) carbonylating methanol; (2) separating the reaction mixture into a volatile phase and a less-volatile phase; (3) distilling the volatile phase to form a first overhead rich in a lower boiling component, and an acetic acid stream rich in acetic acid; and at least one step group selected from the group consisting of the following sections (4), (9), and (15): (4) a section for separating impurities from the acetic acid stream to give purified acetic acid, (9) a section for separating the first overhead into a stream rich in acetaldehyde and a stream rich in methyl iodide, and (15) a section for absorption-treating an off-gas from the process with an absorption solvent and forming a carbon monoxide-rich stream and an acetic acid-rich stream. In this process, the concentration of oxygen in a gaseous phase of the process is controlled to less than 7% by volume and/or the concentration of oxygen in a liquid phase of the process is controlled to less than $7 \times 10^{-5}$ g/g, and the formation of iodine is reduced. The process effectively reduces or prevents local corrosion of an inner wall of a process unit and/or line.

16 Claims, 4 Drawing Sheets

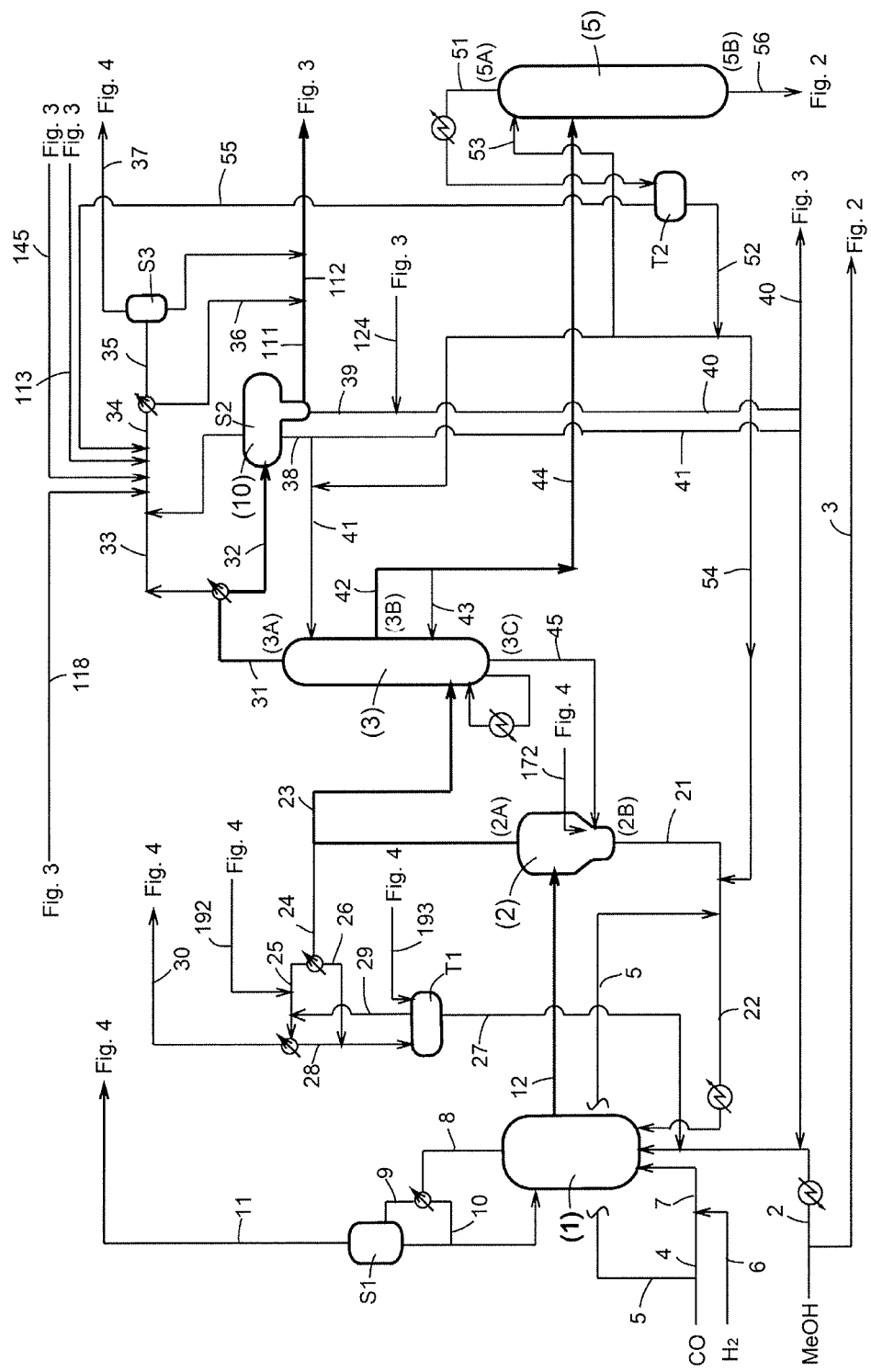
[Fig. 1]

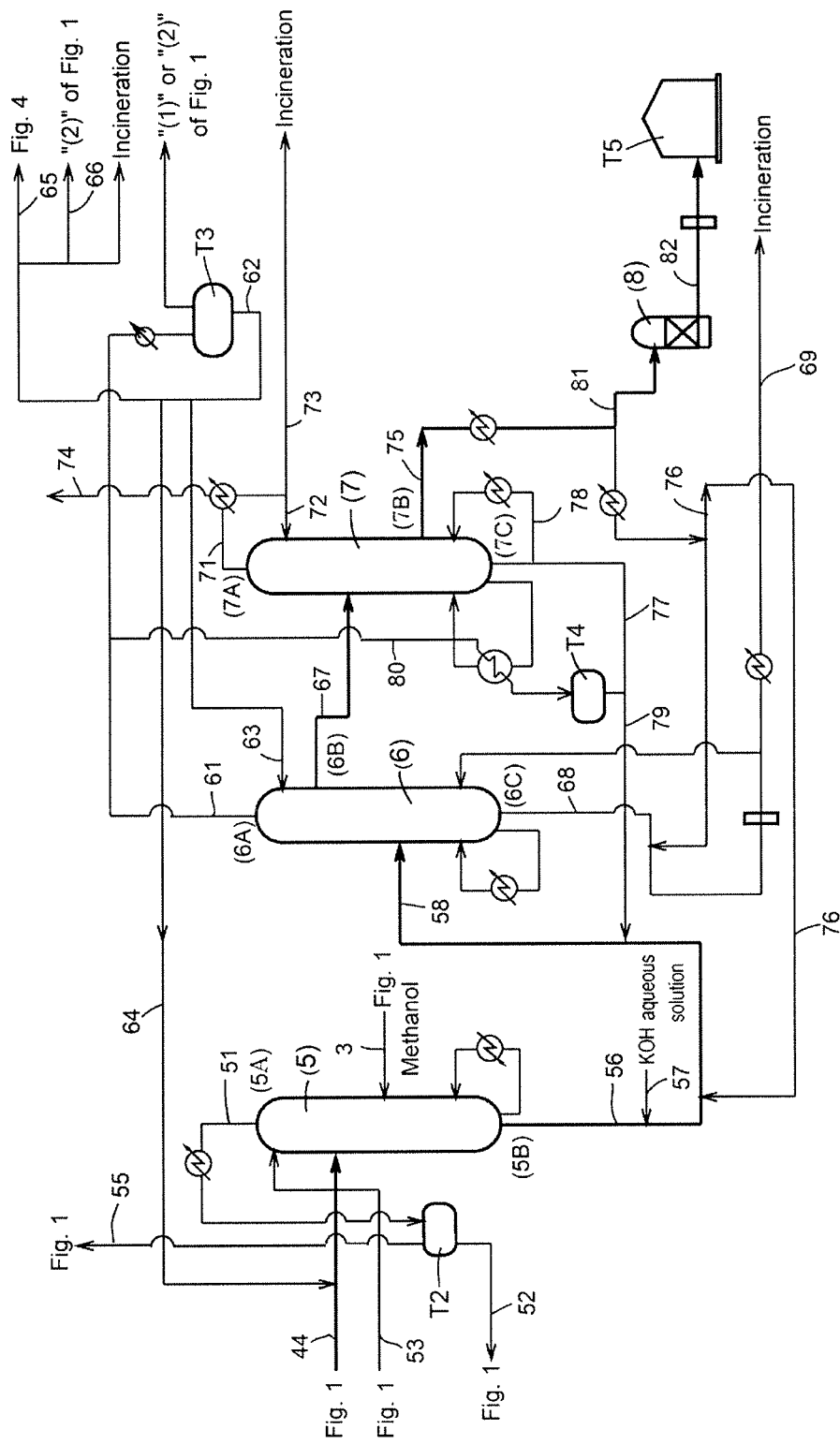
[Fig. 2]

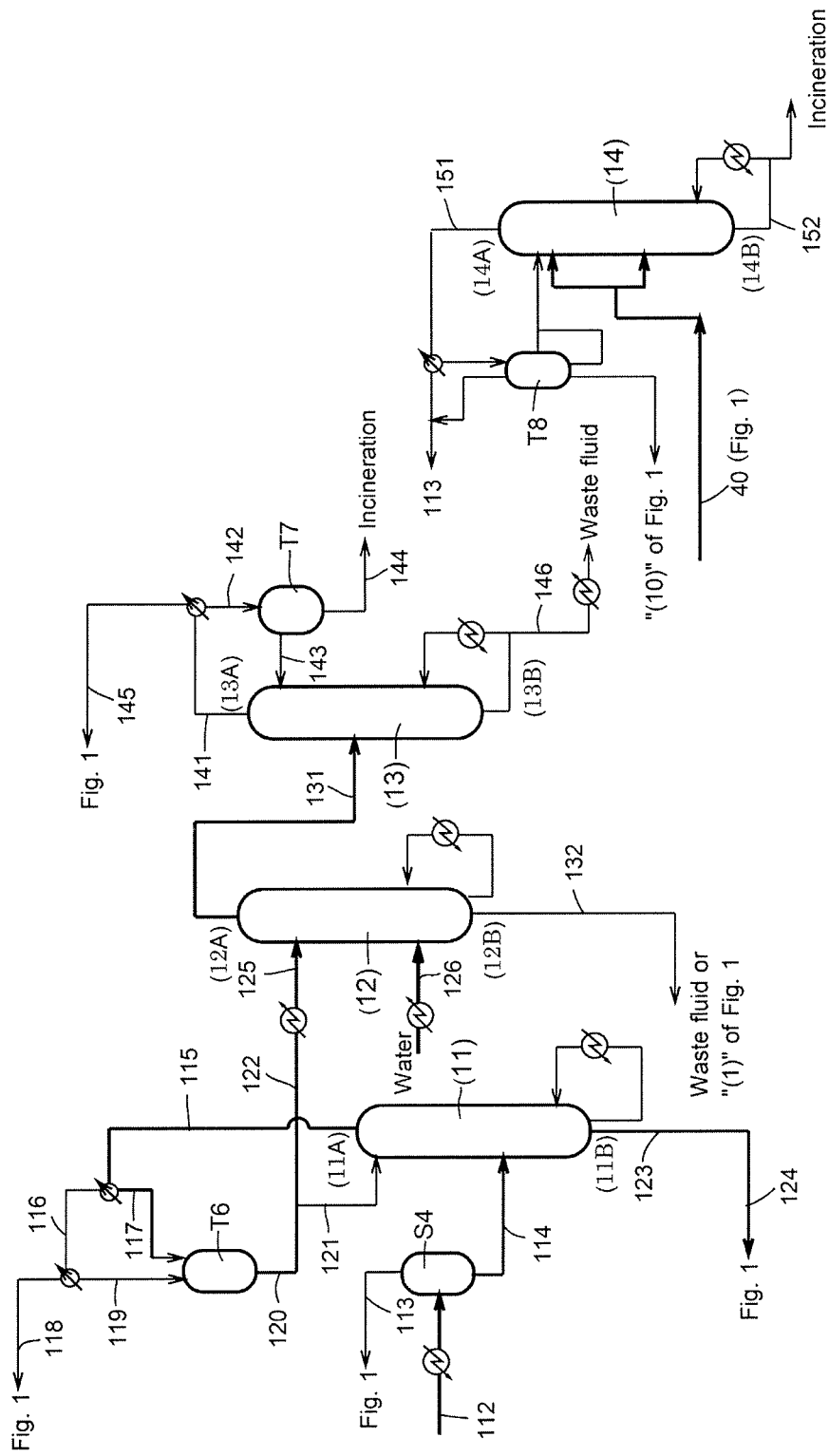
[Fig. 3]

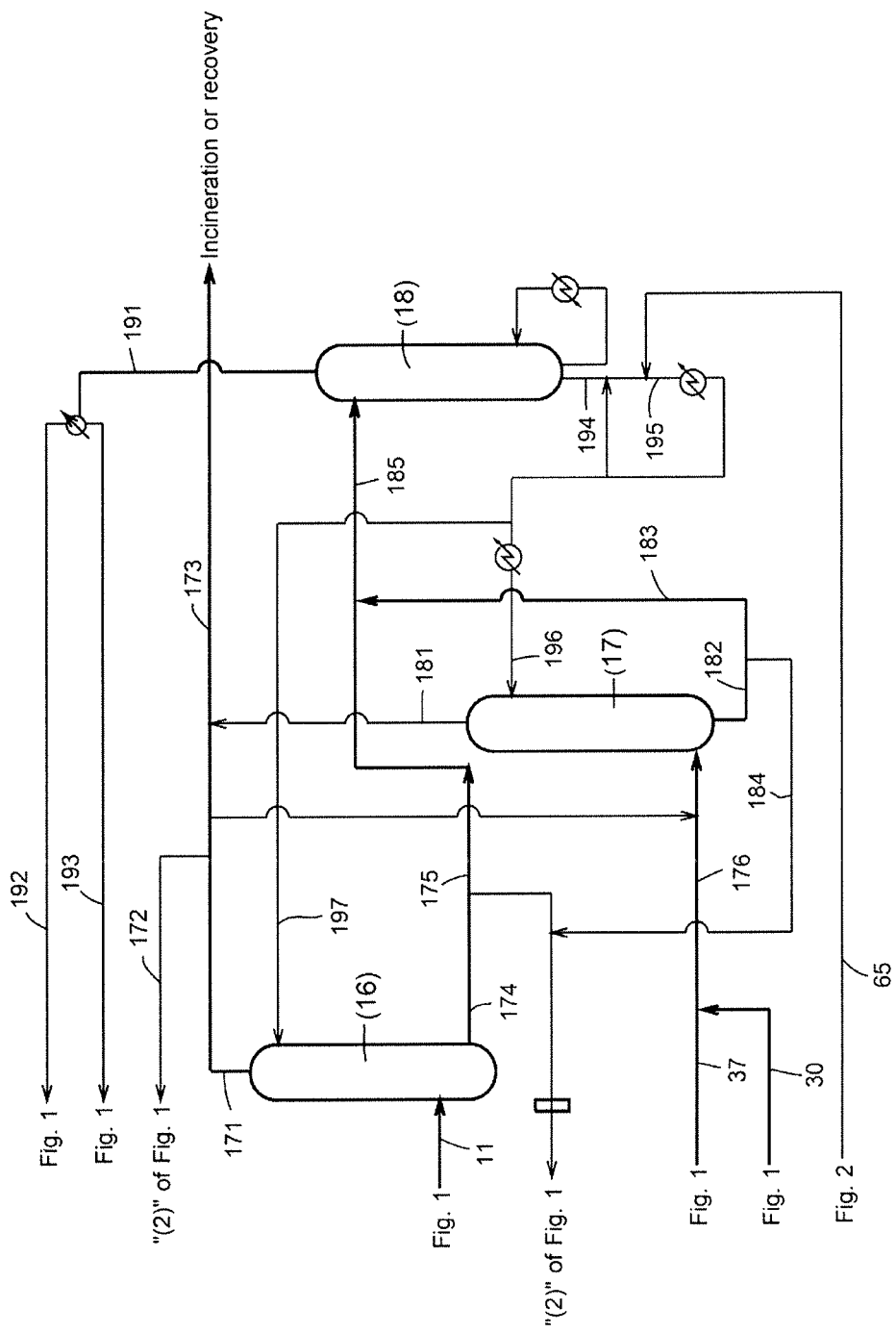
[Fig. 4]

PROCESS FOR PRODUCING ACETIC ACID

CROSS REFERENCE TO RELATED APPLICATIONS

This application is a Continuation of copending application Ser. No. 15/577,524, filed on Nov. 28, 2017, which is a national phase of PCT International Application No. PCT/JP2017/041447 filed on Nov. 17, 2017, which claims the benefit under 35 U.S.C. § 119(a) to Patent Application No. 2017-020775, filed in Japan on Feb. 7, 2017 and Patent Application No. 2017-105771, filed in Japan on May 29, 2017, all of which are hereby expressly incorporated by reference into the present application.

TECHNICAL FIELD

The present invention relates to methods for preventing or reducing the formation of corrosive components such as iodine and processes for producing acetic acid by carbonylation of methanol using the above methods.

BACKGROUND ART

Acetic acid is produced industrially by carbonylating methanol in the presence of water, a rhodium catalyst, a metal iodide, and methyl iodide. In the methanol-carbonylation process, acetic acid is purified and produced by using process units including a reactor for carbonylating methanol under a carbon monoxide atmosphere, an evaporator for separating the reaction mixture fed from the reactor into a volatile phase and a less-volatile phase, a column (or light end column or splitter column) for distilling and separating the volatile phase into at least an overhead and an acetic acid stream, and a dehydration column for separating water from the acetic acid stream. If necessary, acetic acid is produced by further using a column (or heavy end column) for separating higher boiling point impurities and/or a production column following the dehydration column.

Regarding the methanol-carbonylation process, Japanese Patent Application Laid-Open Publication No. 2007-526310 (JP-2007-526310A, Patent Document 1) discloses an improved method for reducing and/or removing a permanganate reducing compound (PRC), a $C_{3-8}$carboxylic acid, and a $C_{2-12}$alkyl iodide compound; the method comprises distilling a volatile phase from a reaction mixture to form a first overhead, distilling the first overhead to form a second overhead containing methyl iodide, dimethyl ether, and the PRC, subjecting the second overhead to water extraction twice, and directly or indirectly introducing at least a portion of the resulting second raffinate to a reaction medium.

Unfortunately, in such a methanol-carbonylation process, corrosion may occur in process units and/or lines. Specifically, an inner wall of a process unit and/or line is selectively corroded, which may result in pitting corrosion or spot corrosion that forms pores. Moreover, a product acetic acid may be colored, lowering in quality.

In the methanol-carbonylation process, it is known that hydrogen iodide corrodes an inner wall of a process unit and/or line. Japanese Patent Application Laid-Open Publication No. 2009-501129 (JP-2009-501129A, Patent Document 2) discloses a process for producing acetic acid comprising: distilling an acetic acid stream containing acetic acid, hydrogen iodide, a lower boiling point component (or lower boiling component), and a higher boiling point component (or higher boiling component) in a first distillation column to form a first lower boiling point stream, a first higher boiling point stream, a first side-cut stream containing acetic acid; and distilling the first side-cut stream in a second distillation column to form a second lower boiling point stream, a second higher boiling point stream, and a second side-cut stream containing acetic acid; wherein water or water and at least one component (A) selected from the group consisting of methanol and methyl acetate is fed to the first distillation column to convert hydrogen iodide into a lower boiling component, such as methyl iodide, for removing hydrogen iodide.

Unfortunately, even after the separation of hydrogen iodide by such a process, pitting corrosion or spot corrosion may still occur in the process unit or line.

CITATION LIST

Patent Literature

Patent Document 1: JP-2007-526310A (Claims)
Patent Document 2: JP-2009-501129A (Claims)

SUMMARY OF INVENTION

Technical Problem

It is therefore an object of the present invention to provide a method for effectively preventing local corrosion of an inner wall of a process unit and/or line and a process for producing acetic acid.

Another object of the present invention is to provide a method for effectively reducing coloring of product acetic acid and a process for producing acetic acid.

It is still another object of the present invention to provide a method for preventing coloring of product acetic acid and preventing corrosion by hydrogen iodide and a process for producing acetic acid.

It is a further object of the present invention to provide a method for effectively preventing corrosion of a process unit and/or line made of a low-grade metal material and a process for producing acetic acid.

Solution to Problem

The inventors of the present invention made intensive studies to achieve the above objects and finally found, in a process for producing acetic acid by carbonylation of methanol, that oxygen enters a process stream by various factors including components introduced in the process from the outside, the oxygen oxidizes hydrogen iodide or methyl iodide to form by-product iodine which corrodes a process unit and/or line; and that control of the concentration of oxygen in the process stream to a predetermined concentration or less effectively reduces the formation of by-product iodine to prevent the local corrosion of the process unit and/or line. The present invention was accomplished based on the above findings.

That is, an aspect of the present invention provides a process for producing acetic acid, comprising: (1) allowing methanol to carbonylation react with carbon monoxide (or carbonylating methanol with carbon monoxide) in the presence of a catalyst system, acetic acid, methyl acetate, and water, wherein the catalyst system contains a metal catalyst, an ionic metal iodide, and methyl iodide; (2) separating the reaction mixture into a volatile phase and a less-volatile phase; (3) distilling the volatile phase to form a first overhead and an acetic acid stream, wherein the first overhead is rich in at least one lower boiling component selected from the group consisting of methyl iodide and acetaldehyde, the acetic acid stream is rich in acetic acid; and at least one section selected from the group consisting of the following sections (4), (9), and (15):

(4) a purification section for obtaining purified acetic acid from the acetic acid stream;

(9) a separation section for separating at least acetaldehyde from the first overhead; and

(15) an off-gas treatment section for absorption-treating an off-gas from the process with an absorption solvent and forming or obtaining a carbon monoxide-rich stream and an acetic acid-rich stream.

The purification section (4) may comprise at least (5) a dehydration step (preferably at least (5) a dehydration step and (6) a higher boiling component removing step) among the following steps (5) to (8):

(5) dehydrating the acetic acid stream (or removing water from the acetic acid stream), (6) removing a higher boiling component (or fraction) from the acetic acid stream, (7) further purification-distilling an acetic acid stream from the step (6), and (8) ion-exchange separating an iodine compound from an acetic acid stream from the step (7).

The separation section (9) may comprise at least steps (10) to (13) among the following steps (10) to (14):

(10) condensing the first overhead to form two liquid phases with an upper phase and a lower phase (or liquid-liquid separating the first overhead by condensation to form an upper phase and a lower phase),

(11) forming a fifth overhead from the upper phase and/or the lower phase, wherein the fifth overhead is rich in acetaldehyde and methyl iodide,

(12) extracting acetaldehyde from the fifth overhead to form an extract and a raffinate, wherein the extract is rich in acetaldehyde and the raffinate is rich in methyl iodide,

(13) separating an aldehyde from the extract and/or the raffinate, and

(14) separating an alkane from the upper phase and/or the lower phase.

The off-gas treatment section (15) may comprise at least one absorption step selected from the group consisting of steps (16) and (17) among the following steps (16) to (18):

(16) absorbing the off-gas to an absorption solvent at a high pressure,

(17) absorbing the off-gas to an absorption solvent at a low pressure, and

(18) diffusing a gas (or a gaseous component) absorbed in the absorption steps (16) and (17).

In the process for producing acetic acid, the concentration of oxygen is controlled (or regulated) in at least one selected from the group consisting of the following (a) and (b):

(a) the concentration of oxygen in a gaseous phase (or a gas phase) of the process is controlled (or regulated) to less than 7% by volume, (b) the concentration of oxygen in a liquid phase of the process is controlled (or regulated) to less than $7 \times 10^{-5}$ g/g.

The gaseous phase of the process may contain at least one member selected from the group consisting of methyl iodide and hydrogen iodide. The gaseous phase of the process may further contain at least one member selected from the group consisting of acetic acid, methyl acetate, methanol, water, acetaldehyde, a by-product derived from acetaldehyde, and a dialkyl ether. The by-product may contain at least one member selected from the group consisting of an alkyl iodide with 2 or more carbon atoms, an alkanal with 4 or more carbon atoms, an alkanecarboxylic acid with 3 or more carbon atoms, an alkane, and a ketone. The dialkyl ether may contain at least dimethyl ether.

In accordance with an aspect of the present invention, in the production process (at least one process stream selected from the group consisting of a stream of a process unit and a stream of a process line), the concentration of oxygen may be controlled or regulated in at least one selected from the group consisting of the following (a-1) and (b-1):

(a-1) the concentration of oxygen in the gaseous phase may be controlled to, for example, 5% by volume or less, (b-1) the concentration of oxygen in the liquid phase may be controlled to, for example, $2 \times 10^{-5}$ g/g or less.

The concentration of oxygen higher than these values may result in the formation of iodine in the process and the corrosion of a process unit or line.

In at least one process stream selected from the group consisting of a stream of a process unit and a stream of a process line, the ratio of oxygen relative to carbon monoxide in each of the gaseous phase and the liquid phase may be 2% by volume or less (for example, 1% by volume or less).

In order to regulate the concentration of oxygen in the gaseous phase and/or the concentration of oxygen in the liquid phase, at least one component (oxygen source) selected from the group consisting of an oxygen-containing gas, an oxygen-containing compound, and an oxygen generator may be introduced in the process. In at least one process stream selected from the group consisting of a stream of a process unit and a stream of a process line, the introduction of such a component (oxygen source) may control (or regulate) the concentration of oxygen in the gaseous phase and/or the concentration of oxygen in the liquid phase to the following concentration(s):

the concentration of oxygen in the gaseous phase may be controlled (or regulated) to 1 ppt by volume or more (for example, 100 ppt by volume or more), the concentration of oxygen in the liquid phase may be controlled (or regulated) to $0.1 \times 10^{-9}$ g/g or more (for example, $0.1 \times 10^{-8}$ g/g or more).

In order to reduce (or prevent) the formation (or production) of iodine, the concentration of oxygen in at least one process stream selected from the group consisting of the gaseous phase and the liquid phase may be controlled (or regulated) to 0.25 mol or less relative to 1 mol of the total amount of hydrogen iodide and methyl iodide.

Another aspect of the present invention provides a method for preventing or reducing formation (or production) of iodine in a process. The method comprises (1) allowing methanol to carbonylation react with carbon monoxide (or carbonylating methanol with carbon monoxide) in the presence of a catalyst system, acetic acid, methyl acetate, and water, wherein the catalyst system contains a metal catalyst, an ionic metal iodide, and methyl iodide; (2) separating the reaction mixture into a volatile phase and a less-volatile phase; (3) distilling the volatile phase to form a first overhead and an acetic acid stream, wherein the first overhead is rich in at least one lower boiling component selected from the group consisting of methyl iodide and acetaldehyde, and the acetic acid stream is rich in acetic acid; and at least one section selected from the group consisting of the following sections (4), (9), and (15):

(4) a purification section for obtaining purified acetic acid from the acetic acid stream;

(9) a separation section for separating at least acetaldehyde from the first overhead; and

(15) an off-gas treatment section for absorption-treating an off-gas from the process with an absorption solvent and forming or obtaining a carbon monoxide-rich stream and an acetic acid-rich stream.

In such a method, the concentration of oxygen is controlled (or regulated) in at least one selected from the group consisting of the following (a) and (b), and the formation of iodine is reduced:

(a) the concentration of oxygen in a gaseous phase portion of the process is controlled (or regulated) to less than 7% by volume, (b) the concentration of oxygen in a liquid stream of the process is controlled (or regulated) to less than $7 \times 10^{-5}$ g/g.

The gaseous phase (or gaseous phase portion) of the process with the predetermined oxygen concentration means all gaseous phases of the process. The gas forming the gaseous phase (or gaseous phase portion) means an off-gas (all off-gases) from the process, and the gas may be an "off-gas" to be subjected to the off-gas treatment section or may be an "off-gas" from a process unit and/or line ("off-gases" from all process units and/or lines). The "off-gas" does not necessarily mean a gas discharged from the process to the outside of the system, but also means a gas in the process (for example, a gas in a process unit and line).

As used in this description and claims, the term "process unit" means an apparatus or a unit for a unit operation of a process, such as a reaction, an evaporation, a distillation, a cooling and/or condensation, a liquid-liquid separation, a holding (storage), or an absorption. As used in this description and claims, acetaldehyde and acetaldehyde-derived by-products that shorten a permanganate time in a permanganate reducing compound test may simply be referred to as PRC's. Examples of such PRC's may include an aldehyde compound, and an alkyl iodide with two or more carbon atoms. Unless otherwise specifically noted, an acetaldehyde-containing aqueous phase obtainable by a liquid-liquid (or biphasic) separation is synonymous with a light phase or an upper phase, and a methyl iodide-containing organic phase obtainable by a liquid-liquid (or biphasic) separation is synonymous with a heavy phase, a methyl iodide phase, or a lower phase. An aqueous phase obtainable by extraction is synonymous with an extract, and an organic phase obtainable by extraction is synonymous with a raffinate.

As used in this description and claims, a gaseous phase portion and a gaseous stream may corretively be referred to as "gaseous phase", and a liquid phase portion and a liquid stream may correctively be referred to as "liquid phase". As used in this description and claims, the total amount of the mixture forming each of the gaseous phase and the liquid phase, including impurities, is 100%. If the mixture forming the gaseous phase (gaseous mixture) contains a condensable component, the composition of the gaseous-phase mixture cannot be measured accurately according to circumstances. The reason why is as follows: even if the mixture is gaseous under a process condition (temperature and pressure), the condensable component in the mixture having a reduced temperature by sampling may be liquefied under a room temperature and an atmospheric pressure (25° C., ≅1 atm 0.1 MPa). Thus, the composition of the mixture forming the gaseous phase (gaseous mixture) is expressed based on the volume (% by volume) or weight (% by weight) of the gaseous-phase mixture at a temperature of 25° C. Moreover, the composition of the mixture forming the liquid phase (liquid mixture) is expressed based on the weight (e.g., % by weight).

Advantageous Effects of Invention

According to the present invention, since the concentration of oxygen in the process stream is controlled (or regulated) to a predetermined concentration or less, the formation of by-product iodine is inhibited and suppressed effectively to reduce or prevent the local corrosion of the inner wall of the process unit and/or line. The process also reduces the total iodine concentration in a product acetic acid to effectively suppress or prevent the coloring of the product acetic acid. Further, the process prevents the coloring of the product acetic acid, as well as reduces the formation of hydrogen iodide from iodine and thus prevents the corrosion by hydrogen iodide. Accordingly, the corrosion of a process unit and/or line made of a low-grade metal material is also effectively preventable.

BRIEF DESCRIPTION OF DRAWINGS

FIG. 1 is a flow diagram for explaining an example of a process from a reaction step through a liquid-liquid separation step and a second distillation step in a production process (or production apparatus) of acetic acid in accordance with an embodiment of the present invention.

FIG. 2 is a flow diagram for explaining an acetic acid purification step including a second distillation step.

FIG. 3 is a flow diagram for explaining a separation step for separating at least acetaldehyde from a liquid-liquid separation step.

FIG. 4 is a flow diagram for explaining an off-gas treatment step for treating an off-gas from a process.

DESCRIPTION OF EMBODIMENTS

In a process for producing acetic acid by carbonylation of methanol, oxygen enters a process stream due to various factors, for example, components introduced in the process from the outside. For example, carbon monoxide or methanol is obtainable by partially oxidizing a carbon source (a carbon compound or a hydrocarbon compound), such as fossil fuel (such as coal or petroleum) or natural gas, with oxygen or air to give a syngas (CO, $H_2$, $CO_2$, a trace of $O_2$), and purifying the syngas; where the method of partially oxidizing the carbon source may include, for example, a steam methane reforming (SMR), an autothermal reforming (ATR), and a partial oxidation (PDX). Not only in the partial oxidation with oxygen but also in the SMR, the carbon source or steam contains oxygen. Accordingly, a trace of oxygen enters the process by introduction (or feeding) of carbon monoxide and methanol as raw materials to a reactor, or by supply or addition of methanol to a process unit (such as a dehydration column or a treatment tank) to convert hydrogen iodide into methyl iodide for removing hydrogen iodide.

Moreover, to adjust a water content in the process, water is supplied to the process or water is used in the process. For example, water is fed to a reaction step; or a first overhead from a light end column (a splitter column) for removing a lower boiling component is distilled in an aldehyde-removing column to form a second overhead, and the second overhead is subjected to extraction with water (e.g., in a water extractor or a water extractive distillation column). Further, an aqueous solution of an alkali metal hydroxide may be used to remove hydrogen iodide in a process unit such as a dehydration column or a treatment tank. Such water contains a trace of oxygen dissolved therein, and oxygen enters the process stream by the use of such water.

Furthermore, the acetic acid production process by carbonylation includes, between a reactor and a production column, apparatuses such as various tanks or hold tanks, pumps, and instruments and gauges (e.g., a level gauge and a pressure gauge). In order to prevent the process stream (e.g., an acetic acid stream) from flowing back to the instruments and gauges and liquefying, or in order to prevent carbon monoxide from leaking from a stirring shaft of the reactor, nitrogen gas purge may be performed to a high-pressure seal portion or other portions. The nitrogen gas purge to the instruments and gauges results in introduction of nitrogen gas into the process. In pressure sealing to a seal portion of the stirring shaft, a portion of nitrogen gas may leak in the reactor through the seal portion. Such nitrogen gas also contains a trace of oxygen.

The oxygen introduced into the process due to various factors as described above reacts with hydrogen iodide or methyl iodide present in the process to generate free iodine $I_2$ by the oxidative reaction (such as $2HI+\frac{1}{2}O_2 \rightarrow I_2+H_2O$; $2CH_3I+\frac{1}{2}O_2 \rightarrow CH_3OCH_3+I_2$). In a case where the generated iodine $I_2$ is attached or adheres to an inner wall of a process unit and/or line, it has been found that the attached portion is selectively or locally corroded, which results in pitting corrosion or spot corrosion that forms pores.

Moreover, in an atmosphere having a water concentration of 5% by weight or less, hydrogen iodide HI usually behaves in the same manner as water and is condensed in top(s) of a light end column for removing a lower boiling component, a dehydration column, a heavy end column for removing a higher boiling component, and/or a production column. Whereas, iodine $I_2$, which has a higher boiling point than hydrogen iodide HI, is carried together with a higher boiling point fraction of the process unit (for example, a side-cut stream from a light end column for removing a lower boiling component, a bottom stream from a dehydration column, and a side-cut stream from a production column) to finally enter the product acetic acid. Thus, it has been also found that the product acetic acid may have an increased iodine concentration or may be colored dark to reddish brown peculiar to iodine $I_2$. The iodine-contaminated product acetic acid inhibits a catalytic activity in producing an acetic acid derivative such as vinyl acetate. Accordingly, it is usually necessary to suppress the concentration of iodine in the product acetic acid to as very low as 10 ppb by weight or less.

Further, as described above, methanol or an alkali metal hydroxide (such as potassium hydroxide) may be added to a process unit such as a dehydration column to convert a trace of hydrogen iodide HI into methyl iodide MeI or an alkali iodide (such as KI) which is then removed. Even in such a method, it is impossible to remove iodine $I_2$ produced from hydrogen iodide HI and/or methyl iodide MeI. In a process downstream side of the process unit such as a dehydration column, the concentration of hydrogen iodide HI is reducible, while exposure of a process stream containing iodine $I_2$ to a reduction atmosphere generates hydrogen iodide HI by the inverse reaction. Thus, an inner wall of a process unit and/or line made of a low-grade metal material (for example, a low-grade material stainless steel (SUS), a HASTELLOY C material) may be corroded not locally by iodine $I_2$ but uniformly by hydrogen iodide HI.

According to an embodiment of the present invention, the concentration of oxygen in the process stream is controlled to solve such problems. Incidentally, the methanol carbonylation process (the reaction system) is usually a pressurized system, and thus the concentration of oxygen in the process stream is regulatable (or controllable) by controlling the oxygen concentrations in raw materials and respective feed lines. For example, the concentration of oxygen in carbon monoxide is controllable by appropriately operating a carbon monoxide production process. For example, the concentration of oxygen in carbon monoxide may be controlled by: regulating (or adjusting) the feed amount of oxygen and/or the feed amount of a steam (water vapor) relative to a carbon monoxide raw material (such as coal or natural gas, heavy oil, or asphalt) to partially oxidize the raw material with oxygen completely; measuring the concentration of oxygen in a purified carbon monoxide to determine the advisability of use based on the measured value; feedback-controlling the carbon monoxide production process based on the measured value to control the concentration of oxygen in carbon monoxide; or introducing an inactive or inert gas based on the measured value to control the concentration of oxygen in carbon monoxide.

Further, with respect to methanol, the concentration of oxygen dissolved in methanol may be measured to determine the advisability of use based on the measured value; or the concentration of dissolved oxygen may be controlled by heating or other means based on the measured value. Moreover, for water and/or an aqueous solution [an alkaline aqueous solution (an aqueous solution of an alkali metal hydroxide) or an aqueous solution of sodium hypophosphite] to be fed to the process (such as the reaction system), the concentration of dissolved oxygen may be measured to determine the advisability of use based on the measured value; or there may be used water or an aqueous solution having a concentration of dissolved oxygen controlled by heating or other means based on the measured value (for example, water or an aqueous solution having a reduced oxygen concentration by boiling or other means).

Further, for a gas or liquid to be fed in the process, the concentration of oxygen may also be measured in the same manner as described above, and the oxygen concentration in the process stream can be adjusted or controlled based on the measured value.

Furthermore, the oxygen concentration in the process stream may be controlled by using a method for minimizing the amount of nitrogen purge gas in the process stream, a method for changing the purge gas to carbon monoxide purge gas or another inactive purge gas, or other methods.

As an oxygen analyzer determining an oxygen concentration in gas or gaseous phase, there may be used various oxygen analyzers, for example, an explosion-proof magnetic pressure type oxygen analyzer (MPA-51d/p manufactured by HORIBA, Ltd.), a separate type zirconia oxygen analyzer (ZR402G, ZR22G, manufactured by Yokogawa Electric Corporation), and a gas analyzer using tunable diode laser absorption spectroscopy [e.g., (all-in-one) SITRANS SL manufactured by NOHKEN Inc.; a gas analyzer manufactured by METTLR; and a gas analyzer ($O_2$ meter) manufactured by Iijima Electronics Corporation].

Examples of an oxygen analyzer (a dissolved oxygen sensor) for liquid or liquid phase may include "DO", "OC", "ODM" and "OBM" types manufactured by DKK-TOA Corporation, "DO meter" manufactured by Iijima Electronics Corporation, and in addition, an oxygen analyzer (manufactured by METTLR) that can measure the concentration of oxygen dissolved in water and a solvent (methanol), and an "OX type" (manufactured by Yokogawa Electric Corporation) for measuring the concentration of oxygen in gas.

According to an "0064 type" 7561L model or other models manufactured by DKK-TOA Corporation, the detection limit of oxygen in a liquid is 0.1 μg/L. For example, the minimum limit of determination of the oxygen concentration in a liquid having a specific gravity of 1 is (0.1/1000000) g/1000 g=0.1 ppb, and the detection limit of the oxygen concentration in a liquid having a specific gravity of 2 is 0.05 ppb. For an "OX400" manufactured by Yokogawa Electric Corporation, the minimum limit of determination of the oxygen concentration in a gas is 0.01 vol ppm (10 ppb). For a sample (a gaseous phase or a liquid phase) having an oxygen concentration of less than the minimum limit of determination, the concentration of oxygen in the sample may be determined by condensing the gaseous phase or the liquid phase using a common method (for example, selective adsorption of oxygen to an adsorbent, selective diffusion of oxygen through a permselective membrane such as an oxygen-enriched membrane, distillation for forming a light fraction and a heavy fraction, and extraction) to give an oxygen concentrate, measuring the concentration of oxygen in the concentrate, and converting the measured value into the concentration of oxygen in the sample.

The concentrations of oxygen in a gas (or a gaseous phase) and a liquid (or a liquid phase) may continuously be observed by monitoring a value detected or measured with an oxygen analyzer (an oxygen sensor) disposed to (or installed in) a process unit or a process line or is observable by regularly taking and analyzing a sample from a process unit or a process line. Moreover, the oxygen concentration may be controlled by comparing the detected or measured value with the oxygen analyzer (the oxygen sensor) with an upper reference value (a threshold value), and, in a case where the detected or measured value reaches the threshold value, automatically introducing a fluid (gas or liquid) having a low oxygen concentration to a process stream or switching the introduction stream to a fluid having a low oxygen concentration. Further, when the oxygen concentration is excessively low (when the concentration of oxygen reaches a threshold value as a lower reference value), an oxygen source may be introduced to the process stream.

In a process under a reduced pressure system, the oxygen concentration in the process stream under the reduced pressure system may be controlled by: controlling the pressure to a predetermined pressure with introduction of an inactive gas while maintaining an airtight condition for holding the operating pressure, then starting the operation, and measuring the oxygen concentration in a waste gas from a vacuum pump.

Such a control of the oxygen concentration allows the reduced formation of by-product iodine and thus provides a useful process condition that solves problems including local corrosion by iodine, increased concentration of total iodine in a product acetic acid, and coloring of the product acetic acid. Moreover, the present invention is highly useful for controlling the iodine concentration in the product acetic acid to a low concentration as extremely low as 10 ppb by weight or less. Furthermore, it is known that high-grade corrosion-resisted metals such as zirconium show a perfect corrosion resistance under a wide-ranging condition including a reducing condition and an oxidizing condition. However, such a high-grade corrosion-resisted metal may be corroded under a strongly oxidizing condition. Thus, depending on the selection of a material of a process unit and/or line, although the process unit and/or line may show a corrosion resistance in an extent of a high oxygen concentration, the process unit and/or line may be corroded according to the concentration of oxygen. The present invention can also reduce such corrosion.

As apparent from these matters, the present invention can also be applied to any process unit (step) and line in a process for producing acetic acid by methanol carbonylation.

The present invention can be applied to a process stream (for example, a gaseous phase of a process) containing at least one member selected from the group consisting of methyl iodide and hydrogen iodide for reducing the formation of by-product iodine. Further, as described later, the process stream (for example, a gaseous phase of a process) may contain at least one member selected from the group consisting of acetic acid, methyl acetate, methanol, water, acetaldehyde, by-products derived from acetaldehyde, and dialkyl ethers, depending on the process unit and/or the process line. The by-products may contain at least one member selected from the group consisting of an alkyl iodide with 2 or more carbon atoms, an alkanal with 4 or more carbon atoms, an alkanecarboxylic acid with 3 or more carbon atoms, an alkane, and a ketone. The dialkyl ethers may contain at least dimethyl ether.

According to an embodiment of the present invention, at least one oxygen concentration selected from the group consisting (a) a concentration of oxygen in a gaseous phase of a process and (b) a concentration of oxygen in a liquid phase of a process as described later is controlled in a production process of acetic acid (at least one process stream selected from the group consisting of a stream of a process unit and a stream of a process line).

(a) The concentration of oxygen in the gaseous phase of the process is controlled to less than 7% by volume, and may be 6.5% by volume or less (for example, 6% by volume or less), preferably 5.5% by volume or less, or may be controlled to usually 5% by volume or less (for example, 3% by volume or less), preferably 1% by volume or less (for example, 0.5% by volume or less), more preferably 0.1% by volume or less (for example, 0.01% by volume or less), and particularly 0.001% by volume (10 ppm by volume) or less (for example, 0.0001% by volume (1 ppm by volume) or less).

The concentration of oxygen in the gaseous phase may have any lower limit, and may be, for example, 1 ppt by volume or more (for example, 100 ppt by volume or more), preferably 1 ppb by volume or more (for example, 100 ppb by volume or more) or may be zero (0) or a minimum limit of determination (or measurement) or less.

(b) The concentration of oxygen in the liquid phase and may be controlled to $2 \times 10^{-5}$ g/g or less (for example, $1 \times 10^{-5}$ g/g or less), preferably $0.5 \times 10^{-5}$ g/g or less (for example, $0.1 \times 10^{5}$ g/g or less), more preferably $0.05 \times 10^{-5}$ g/g or less (for example, $0.01 \times 10^{-5}$ g/g or less), and particularly $0.001 \times 10^{-5}$ g/g or less (for example, $0.0001 \times 10^{-5}$ g/g or less).

Moreover, the concentration of oxygen in the liquid phase may have any lower limit, and may be, for example, $0.1 \times 10^{-9}$ g/g or more or may be zero (0) or a minimum limit of determination (or measurement) or less. In a liquid phase such as a process liquid under pressure or a high-temperature process liquid, in some cases, the concentration of oxygen (or the concentration of dissolved oxygen) cannot be measured accurately due to difficulty of sampling, vaporization of oxygen, or other factors. In such a case, the concentration of oxygen in the process liquid may be measured, as an estimated value (an experimental estimated value), by determining a concentration of oxygen in the process liquid under a plurality of conditions with varying temperatures and/or pressures to estimate an oxygen concentration at an actual process temperature and pressure, or may be calculated using Aspen Plus (manufactured by Aspen Technology, Inc.).

As the concentration of oxygen in the process stream (the gaseous phase and the liquid phase) is increased, iodine is easily formed in the process stream.

Though a lower oxygen concentration is preferred, in a case where the concentration of oxygen is too low, the corrosion speed of the process unit and/or line may be increased due to an excessively strong reducing atmosphere. Thus, to control the oxygen concentration in the process stream (the gaseous phase and the liquid phase), at least one oxygen source selected from the group consisting of an oxygen-containing gas, an oxygen-containing compound, and an oxygen generator may be introduced to the process to control the oxygen concentration in the gaseous phase and/or liquid phase in the process stream.

Examples of the oxygen-containing gas may include air. Examples of the oxygen-containing compound may include ozone. Examples of the oxygen generator may include peracetic acid and hydrogen peroxide. These oxygen sources may be used alone or in combination.

Further, the oxygen concentration in a process stream selected from the group consisting of a gaseous stream as a gaseous phase and a liquid stream as a liquid phase may be, for example, relative to 1 mol of the total amount of hydrogen iodide and methyl iodide, about 0.25 mol or less (e.g., about 0.2 mol or less), preferably about 0.1 mol or less (e.g., about 0.05 mol or less), more preferably about 0.01 mol or less (e.g., about $1\times10^{-3}$ mol or less), particularly about $1\times10^{-4}$ mol or less (e.g., about $1\times10^{-5}$ mol or less) or may be about $1\times10^{-6}$ mol or less (e.g., about $1\times10^{-7}$ mol or less).

Further, in at least one process stream selected from the group consisting of a stream of a process unit and a stream of a process line, the ratio of oxygen relative to carbon monoxide ($O_2/CO$) in each of a gaseous phase and a liquid phase (for example, a gaseous phase) may be 7% by volume or less (e.g., 5% by volume or less), for example, 2% by volume or less (e.g., 1% by volume or less), preferably 0.5% by volume or less (e.g., 0.1% by volume or less), more preferably 0.01% by volume or less (e.g., 0.001% by volume or less), and particularly 0.0001% by volume or less (e.g., 0.00001% by volume or less).

In the process stream, the concentration of oxygen in the liquid phase is low practically, and the ratio ($O_2/CO$) of oxygen relative to carbon monoxide may significantly fluctuate in some cases. The ratio ($O_2/CO$) of oxygen relative to carbon monoxide in the liquid phase may be, for example, 1000% by weight or less (10 times or less) (e.g., 500% by weight or less), or may be 250% by weight or less (e.g., 100% by weight or less), preferably 75% by weight or less (e.g., 50% by weight or less), more preferably 20% by weight or less (e.g., 10% by weight or less), or may be 5% by weight or less (e.g., 1% by weight or less), preferably 0.1% by weight or less (e.g., 0.01% by weight or less), more preferably 0.001% by weight or less (e.g., 0.0001% by weight or less), and particularly 0.00005% by weight or less (e.g., 0.00001% by weight or less).

As described later, the volume percent (% by volume) and the weight percent (% by weight) of each component described above may be calculated or converted mutually using an average molecular weight (a weighted average molecular weight).

Hereinafter, the present invention will be explained in detail with reference to the drawings if necessary. Each step and a main apparatus or unit for the corresponding step may be indicated by the same reference numeral or sign.

The process (or apparatus) for continuously producing acetic acid as shown in FIG. 1 to FIG. 4 comprises (1) a reaction step (a reaction system or a reactor) for carrying out a carbonylation reaction of methanol; (2) a step (a flash evaporation step or a flasher) for separating the reaction mixture into a volatile phase (2A) and a less-volatile phase (2B); and (3) a step (a first distillation step, a splitter column) for distilling and separating the volatile phase (2A) to form a first overhead (3A), an acetic acid stream (3B), and a bottom liquid stream (higher boiling point fraction (or component)) (3C), the first overhead (3A) being rich in at least one lower boiling component selected from the group consisting of methyl iodide and acetaldehyde, the acetic acid stream (3B) being rich in acetic acid; and further comprises (4) a purification section or purification step group for obtaining purified acetic acid from the acetic acid stream (3B) (steps (5) to (8)); (9) a separation section or separation step group for separating at least acetaldehyde from the first overhead (3A) (steps (10) to (14)); and (15) an off-gas treatment section or off-gas treatment step group for absorption-treating an off-gas from the process with an absorption solvent to separate the off-gas into a stream rich in carbon monoxide and a stream rich in acetic acid, methyl iodide, and methyl acetate (steps (16) to (18)).

According to an embodiment of the present invention, the process comprises, in addition to the above steps (1) to (3), at least one section (step group or unit group) selected from the group consisting of the sections (4), (9), and (15). For example, the off-gas treatment section (15) is not necessarily needed. In the off-gas treatment section (15), treatment of off-gases from all units or lines is not necessarily needed, and off-gas(s) from predetermined process unit(s) or line(s) may be treated. The gaseous phase or gaseous phase portion of the process having the predetermined oxygen concentration means all gaseous phases of the process; the gas forming the gaseous phase includes an off-gas from the process irrespective of discharge to the outside of the system. The off-gas may be an "off-gas" to be subjected to the off-gas treatment section or may be an off-gas from a process unit and/or line. Hereinafter, each step will be explained in detail.

(1) Reaction Step (Reactor)

In the reaction step (1), methanol from a feed line 2 and carbon monoxide from a feed line 4 are continuously fed to a reactor (1) in the presence of a reaction medium containing a carbonylation catalyst system and water to produce acetic acid by carbonylation of methanol. The carbon monoxide from the line 4 is mixed with hydrogen fed from a line 6 for the purpose of increasing a catalytic activity, and the mixture is fed as a mixed gas 7 to the reactor (1). Methanol is fed to the reactor (1), and methanol is added to a distillation column of a second distillation step (5) via a line 3. Carbon monoxide from a line 5 is mixed with a less-volatile phase (a bottom catalyst liquid) from a recycle line 21 of an evaporator (2) in order to prevent precipitation of the catalyst and the mixed catalyst liquid is recycled to the reactor (1) via a line 22.

Moreover, in a liquid-liquid separation step (10), an upper phase 38 (an upper phase rich in acetic acid, methyl iodide, methyl acetate, and water) and a lower phase 39 (a lower phase rich in methyl iodide and methyl acetate) are biphasically formed in the decanter S2, and a portion 41 of the upper phase 38 and a portion 40 (or a first portion) of the lower phase 39 may be recycled to the reactor (1). A portion (or a second portion) 40 of the lower phase 39 may be subjected to an alkane separation step (distillation step) (14). Moreover, a portion 54 of a condensate (a portion of a condensate rich in acetic acid) of a second overhead 51 from a distillation column of a second distillation step (5) may also be mixed or merged with the less-volatile phase (2B) (the line 21), and the mixture may be recycled to the reactor (1).

Fresh methanol may be fed to the reaction system (1) directly or indirectly, or methanol or a derivative thereof withdrawn from various succeeding distillation steps may be fed to the reaction system by recycling to the reaction step. As such a raw material methanol, it is preferred to use methanol from which oxygen has been removed beforehand. The carbon monoxide may be used as a pure gas or may be used as a gas diluted with an inactive or inert gas (for example, nitrogen, helium, and carbon dioxide). If necessary, a waste gas containing carbon monoxide obtained from the succeeding step(s) may be recycled to the reaction system. As such carbon monoxide or waste gas, it is preferred to use carbon monoxide or waste gas from which oxygen has been removed beforehand.

In the following Tables, $O_2$ represents oxygen, $H_2$ denotes hydrogen, CO represents carbon monoxide, $CO_2$ denotes carbon dioxide, $CH_4$ represents methane $N_2$ denotes nitrogen, AD represents acetaldehyde, MeOH denotes methanol, MeI represents methyl iodide, MA denotes methyl acetate, $H_2O$ represents water, AcOH denotes acetic acid, HI represents hydrogen iodide, LiI denotes lithium iodide, FrOH represents formic acid, PrOH denotes propionic acid, DME represents dimethyl ether, AcA denotes acetic anhydride, $(CH_3)_2C=O$ represents acetone, EtOH denotes ethanol, EA represents ethyl acetate, EtI denotes ethyl iodide, TOI represents total iodine compounds, and HexI denotes hexyl iodide (the same applies hereinafter). Moreover, the concentration of HI represents a concentration in terms of iodide ion. Metals are represented by atomic symbols.

For reference, some of the following Tables describe an average molecular weight of a stream. The average molecular weight means a weighted average value calculated based on the molecular weight and proportion of each component contained in a stream. Incidentally, when a gaseous-phase mixture has an average molecular weight (a weighted average molecular weight) A and contains a component having a molecular weight B, the volume percent (% by volume) or weight percent (% by weight) of the component can be calculated on the basis of the weight percent (% by weight) or volume percent (% by volume) of the component. For a concentration of oxygen as one example, when the average molecular weight A of a gaseous-phase mixture is 62.2 (weighted average molecular weight) and the measured value of a volume percent D of oxygen in the gaseous-phase mixture is 7.0% by volume, a weight percent C of oxygen can be, for example, calculated from the molecular weight B (=32) of oxygen and the following equation: $(C \times 100) \times A / B = D \times 100$, as follows: $(C \times 62.2)/32=7$, the weight percent C of oxygen=3.6% by weight. Thus, the weight percent (% by weight) and volume percent (% by volume) of each component in the gaseous-phase mixture can be calculated from the above equation. Accordingly, the following Tables denote component concentrations in only weight percent (% by weight).

For a sample (a gaseous phase and a liquid phase) in which a gaseous component other than oxygen has a concentration less than the limit of detection (or detection limit), the concentration of the gaseous component in the sample may be determined by forming a concentrate in the same manner as in the case of the concentration of oxygen, measuring the concentration of the gaseous component in the concentrate, and converting the measured value into a concentration of the gaseous component in the sample.

Moreover, for a sample (a gaseous phase and a liquid phase) in which a component has a concentration less than the detection limit (e.g., less than 0.1 ppb for a metal component, less than 1 ppm for organic matter), the concentration of the component in the sample may be determined by forming a concentrate of the component, measuring the concentration of the component in the concentrate, and converting the measured value into a concentration of the component in the sample. In a case where the component concentration in a sample is unmeasurable, the component concentration may be estimated according to distillation calculation and entrainment by evaporation. For example, with respect to amounts of entrainment in adjacent stages or plates in an evaporation operation or an operation of a distillation column, the amount of entrainment in a higher stage or plate corresponds to about 1 to 20% by weight that in a lower stage or plate, and the concentration of a metal in a liquid in a higher stage or plate is about 1 to 20% by weight of that in a lower stage or plate. Based on such an estimated value, the concentration of the metal may be determined.

Incidentally, an inactive gas may be introduced in the process. For example, an inactive gas (such as nitrogen gas $N_2$) is fed to a process unit (such as a distillation column) for the purpose of regulating an internal pressure of the unit, and/or an inactive gas (such as nitrogen gas $N_2$) purge to a measuring instrument (such as a pressure gauge, a thermometer, or a level gauge) is performed for the purpose of preventing an organic matter vapor from entering the measuring instrument. Moreover, an inactive gas such as carbon monoxide gas CO may be introduced instead of nitrogen gas $N_2$. Further, water, an alkali metal compound, a methanol source, or others may be introduced to the process unit and line. In such a case, a concentration of a feed component [for example, a composition of a gas (e.g., an inactive gas such as nitrogen gas $N_2$ or carbon monoxide)] in the following Tables, which show a composition in the process unit and line, drastically increases or changes depending on the feed component (such as an inactive gas) and an amount thereof.

For example, the raw material methanol (the line 2) may have the following composition (unit: % by weight).

TABLE 1

|  | Range | Preferred range | More preferred range |
| --- | --- | --- | --- |
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 1% (e.g., 1 ppt to 0.1%) | 10 ppt to 0.01% | 100 ppt to 0.001% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.1%) | 10 ppt to 0.01% | 100 ppt to 0.001% |
| AD | 0 to 1% (e.g., 1 ppb to 0.1%) | 10 ppb to 0.01% | 100 ppb to 0.001% |
| MeOH | 95 to 100% | 98 to 99.999% | 99 to 99.99% |
| MeI | 0 to 1% (e.g., 1 ppt to 0.1%) | 10 ppt to 0.01% | 100 ppt to 0.001% |

TABLE 1-continued

|  | Range | Preferred range | More preferred range |
|---|---|---|---|
| MA | 0 to 1% (e.g., 1 ppb to 0.1%) | 10 ppb to 0.01% | 100 ppb to 0.001% |
| $H_2O$ | 1 ppm to 0.1% | 10 ppm to 0.05% | 100 ppm to 0.01% |
| AcOH | 0 to 1% (e.g., 1 ppb to 0.1%) | 10 ppb to 0.01% | 100 ppb to 0.001% |
| HI | 0 to 1% (e.g., 0.1 ppb to 0.5%) | 1 ppb to 0.1% | 10 ppb to 100 ppm |
| FrOH | 0 to 1% (e.g., 1 ppm to 0.1%) | 5 to 100 ppm | 10 to 30 ppm |
| PrOH | 0 to 1% (e.g., 0.1 ppm to 0.1%) | 1 to 100 ppm | 10 to 30 ppm |
| DME | 0 to 1% (e.g., 1 ppb to 100 ppm) | 10 ppb to 30 ppm | 100 ppb to 5 ppm |
| AcA | 0 to 1% (e.g., 1 ppb to 0.1%) | 10 ppb to 100 ppm | 100 ppb to 50 ppm |
| $(CH_3)_2C=O$ | 0 to 1% (e.g., 1 ppb to 100 ppm) | 10 ppb to 50 ppm | 100 ppb to 30 ppm |
| EtOH | 0 to 1% (e.g., 1 ppb to 100 ppm) | 10 ppb to 50 ppm | 100 ppb to 10 ppm |
| EA | 0 to 1% (e.g., 1 ppb to 100 ppm) | 10 ppb to 50 ppm | 100 ppb to 10 ppm |
| EtI | 0 to 1% (e.g., 1 ppb to 100 ppm) | 10 ppb to 50 ppm | 100 ppb to 10 ppm |
| Li | 0 to 0.1% (e.g., 0.01 ppt to 100 ppb) | 1 ppt to 10 ppb | 10 ppt to 1 ppb |
| Rh | 0 to 0.1% (e.g., 0.01 ppt to 100 ppb) | 1 ppt to 10 ppb | 10 ppt to 1 ppb |
| Fe | 0 to 0.1% (e.g., 1 ppt to 1 ppm) | 10 ppt to 0.5 ppm | 100 ppt to 0.1 ppm |
| Ni | 0 to 0.1% (e.g., 1 ppt to 1 ppm) | 10 ppt to 0.5 ppm | 100 ppt to 0.1 ppm |
| Cr | 0 to 0.1% (e.g., 1 ppt to 1 ppm) | 10 ppt to 0.5 ppm | 100 ppt to 0.1 ppm |
| Mo | 0 to 0.1% (e.g., 1 ppt to 1 ppm) | 10 ppt to 0.5 ppm | 100 ppt to 0.1 ppm |
| Zn | 0 to 0.1% (e.g., 1 ppt to 1 ppm) | 10 ppt to 0.5 ppm | 100 ppt to 0.1 ppm |
| Cu | 0 to 0.1% (e.g., 1 ppt to 1 ppm) | 10 ppt to 0.5 ppm | 100 ppt to 0.1 ppm |

For example, the raw material carbon monoxide (the lines 4, 5) may have the following composition (unit: % by weight).

TABLE 2

|  | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%), or less than 7% (e.g., 0.1 ppb to 5%), e.g., 1 ppb to 3% (e.g., 10 ppb to 1%) | 2 ppb to 1% (e.g., 10 ppb to 0.1%), or 20 ppb to 5000 ppm | 50 ppb to 500 ppm (e.g., 100 ppb to 100 ppm), or 50 ppb to 1000 ppm |
| $H_2$ | 0 to 1% (e.g., 1 ppt to 0.1%) | 10 ppt to 0.01% | 100 ppt to 0.001% |
| CO | 95 to 100% | 98 to 99.999% | 99 to 99.99% |
| $CO_2$ | 0 to 1% (e.g., 1 ppt to 0.1%) | 10 ppt to 0.01% | 100 ppt to 0.001% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.1%) | 10 ppt to 0.01% | 100 ppt to 0.001% |
| AD | 0 to 1% (e.g., 1 ppb to 0.1%) | 10 ppb to 0.01% | 100 ppb to 0.1 ppm |
| MeOH | 0 to 1% (e.g., 1 ppb to 0.1%) | 10 ppb to 0.01% | 100 ppb to 0.1 ppm |
| MeI | 0 to 1% (e.g., 1 ppt to 0.1%) | 10 ppt to 0.01% | 100 ppt to 0.1 ppm |
| MA | 0 to 1% (e.g., 1 ppb to 0.1%) | 10 ppb to 0.01% | 100 ppb to 0.1 ppm |
| $H_2O$ | 0 to 1% (e.g., 1 ppm to 0.1%) | 10 ppm to 0.05% | 20 ppm to 0.01% |
| AcOH | 0 to 1% (e.g., 1 ppb to 0.1%) | 10 ppb to 0.01% | 100 ppb to 0.1 ppm |
| FrOH | 0 to 1% (e.g., 1 ppm to 0.1%) | 5 to 100 ppm | 10 to 50 ppm |
| PrOH | 0 to 1% (e.g., 1 ppb to 0.1%) | 1 to 100 ppm | 10 to 50 ppm |
| DME | 0 to 0.1% (e.g., 1 ppb to 100 ppm) | 10 ppb to 30 ppm | 100 ppb to 0.1 ppm |
| $(CH_3)_2C=O$ | 0 to 1% (e.g., 1 ppb to 100 ppm) | 10 ppb to 50 ppm | 100 ppb to 0.1 ppm |
| EtOH | 0 to 1% (e.g., 1 ppb to 100 ppm) | 10 ppb to 50 ppm | 100 ppb to 0.1 ppm |
| EA | 0 to 1% (e.g., 1 ppb to 100 ppm) | 10 ppb to 50 ppm | 100 ppb to 0.1 ppm |
| EtI | 0 to 1% (e.g., 1 ppb to 100 ppm) | 10 ppb to 50 ppm | 100 ppb to 0.1 ppm |

The composition of the mixed gas (the line 7) may, for example, be substantially the same as (or similar to) the composition of the raw material carbon monoxide (the lines 4, 5). Moreover, the composition of the mixed gas (the line 7) may have a component ratio (content of each component) obtained or calculated from the weighted average of the component ratio of the raw material carbon monoxide (the line 4, 5) and the component ratio of hydrogen (the line 6).

The carbonylation catalyst system usually contains a metal catalyst (such as a cobalt catalyst, a rhodium catalyst, or an iridium catalyst), a catalyst stabilizer or reaction accelerator, and/or a co-catalyst. The metal catalysts may be used alone or in combination. The metal catalyst may preferably include a rhodium catalyst and an iridium catalyst (in particular, a rhodium catalyst).

The metal catalyst may be used in the form of a simple metal, a metal oxide (including a complex metal oxide), a metal hydroxide, a metal iodide, a metal carboxylate (e.g., an acetate), a metal salt of an inorganic acid (e.g., a sulfate, a nitrate, and a phosphate), or a metal complex. It is preferred to use the metal catalyst in a form (e.g., a complex form) dissolvable in a liquid phase (or a reaction medium or liquid). The rhodium catalyst may preferably include, for example, a rhodium iodide complex {e.g., $RhI_3$, $[RhI_2(CO)_4]^-$, and $[Rh(CO)_2I_2]^-$} and a rhodium carbonyl complex.

The catalyst stabilizer or reaction accelerator may include an ionic metal iodide capable of producing an iodide ion in the reaction medium, for example, an alkali metal iodide (e.g., lithium iodide, sodium iodide, and potassium iodide). Among these stabilizers, lithium iodide is preferred. The catalyst stabilizer or reaction accelerator may include, in addition to lithium iodide and analogous compounds, a metal compound (such as a metal iodide or a complex) having a transition metal (including a metal or a corroded metal present in the reaction system, as shown in the following Tables). Examples of the transition metal may include a group 6 element of the Periodic Table (such as molybdenum, chromium, or tungsten), a group 7 element of the Periodic Table (such as manganese or rhenium), a group 8 element of the Periodic Table (such as iron, ruthenium, or osmium), a group 9 element of the Periodic Table (such as cobalt, rhodium, or iridium), a group 10 element of the Periodic Table (such as nickel), a group 11 element of the Periodic Table (such as copper), a group 12 element of the Periodic Table (such as cadmium or zinc), and a group 13 element of the Periodic Table (such as gallium or indium). These catalyst stabilizers or accelerators may be used alone or in combination according to the species of the metal catalyst. For an iridium catalyst system, an alkali iodide metal is not necessarily needed. As the co-catalyst, methyl iodide may be used.

A preferred carbonylation catalyst system may comprise a rhodium catalyst, a metal iodide as a catalyst stabilizer (e.g., lithium iodide), and methyl iodide as a co-catalyst. To the reactor may be fed a catalyst mixture (a catalyst liquid) containing the carbonylation catalyst system, and water. It is preferred that oxygen have been removed beforehand from such a catalyst mixture and water by heating or boiling.

The carbon monoxide partial pressure in the reactor may be a pressure of, for example, about 2 to 30 atmospheres and preferably about 4 to 15 atmospheres. The carbonylation reaction produces hydrogen by a reaction of carbon monoxide with water. Hydrogen increases the catalyst activity. Thus hydrogen may be fed to the reactor if necessary. Hydrogen may be fed to the reactor by recycling gaseous component(s) (including hydrogen, carbon monoxide, or other gases) exhausted in the succeeding step(s), if necessary after purifying the gaseous component(s). As such hydrogen, it is preferred to use hydrogen having less oxygen concentration. The hydrogen partial pressure in the reaction system may be a pressure of, for example, about 0.5 to 250 kPa (e.g., about 1 to 200 kPa), preferably about 5 to 150 kPa, and more preferably about 10 to 100 kPa (e.g., about 10 to 50 kPa) in terms of absolute pressure.

The temperature of the carbonylation reaction may be, for example, about 150 to 250° C., preferably about 160 to 230° C., and more preferably about 170 to 220° C. The reaction pressure (total reactor pressure), including partial pressures of by-products, may be, for example, about 15 to 40 atmospheres. The space time yield of acetic acid in the reaction system may be, for example, about 5 to 50 mol/Lh, preferably about 8 to 40 mol/Lh, and more preferably about 10 to 30 mol/Lh.

In the reactor, the carbonylation reaction of methanol proceeds with forming an equilibrium between a liquid-phase reaction system and a gaseous-phase system. The liquid-phase reaction system contains the reactant (s) and the metal catalyst component, and the gaseous-phase system comprises carbon monoxide, reaction by-products (hydrogen, methane, and carbon dioxide), and vaporized lower boiling components (e.g., methyl iodide, a product acetic acid, and methyl acetate).

The metal catalyst in the liquid phase has a concentration of, for example, about 100 to 5000 ppm by weight, preferably about 200 to 3000 ppm by weight, more preferably about 300 to 2000 ppm by weight, and particularly about 500 to 1500 ppm by weight in the whole liquid phase in the reactor. The catalyst stabilizer or reaction accelerator in the whole liquid phase in the reactor has a concentration of, for example, about 1 to 25% by weight, preferably about 2 to 22% by weight, and more preferably about 3 to 20% by weight. The iodide ion in the reaction system may have a concentration of, for example, about 0.05 to 2.5 mol/L and preferably about 0.25 to 1.5 mol/L. The methyl iodide in the whole liquid phase in the reactor has a concentration of, for example, about 1 to 30% by weight, preferably about 5 to 25% by weight, and more preferably about 6 to 20% by weight (e.g., about 8 to 18% by weight).

The reaction medium (or liquid phase) usually contains the product acetic acid, methyl acetate formed by a reaction of the product acetic acid and raw material methanol, and water. The acetic acid also plays as a solvent. Moreover, the reaction medium (or the liquid phase) usually contains unreacted raw material methanol. The proportion of methyl acetate in the whole reaction liquid may be about 0.1 to 30% by weight, preferably about 0.3 to 20% by weight, and more preferably about 0.5 to 10% by weight (e.g., about 0.5 to 6% by weight). The water in the reaction medium may have a low concentration, and may have, in the whole reaction liquid, a concentration of, for example, about 0.1 to 15% by weight, preferably about 0.5 to 10% by weight, and more preferably about 0.8 to 5% by weight (e.g., about 1 to 3% by weight) and may usually be about 1 to 10% by weight (e.g., about 2 to 5% by weight).

The reaction mixture (the crude reaction liquid) also contains various by-products including acetaldehyde and by-products derived from acetaldehyde. The present invention allows effective removal of acetaldehyde in the separation section (9). Thus, the present invention enables the concentration of acetaldehyde in the reactor to be decreased and also enables the production of by-products derived from acetaldehyde to be prevented, although the reaction is a continuous reaction. An acetaldehyde concentration in the liquid phase in the reactor may be, for example, not more than 1500 ppm by weight, e.g., about 10 to 1000 ppm by weight, preferably about 50 to 500 ppm by weight, and more preferably about 100 to 400 ppm by weight.

Examples of the by-products derived from acetaldehyde (acetaldehyde derivatives) may include an aldehyde such as butyraldehyde, crotonaldehyde, 2-ethylcrotonaldehyde, and 2-ethylbutyraldehyde; a ketone such as acetone or methyl ethyl ketone; an aldol condensation product thereof; and a $C_{2-12}$alkyl iodide such as ethyl iodide, propyl iodide, butyl iodide, pentyl iodide, or hexyl iodide. The by-products may also include formic acid, a carboxylic acid having 3 or more carbon atoms [e.g., a straight chain or branched chain carboxylic acid such as propionic acid, butanoic acid, pentanoic acid, hexanoic acid, heptanoic acid, octanoic acid, and a higher fatty acid having 9 or more carbon atoms (e.g., a $C_{3-12}$alkanecarboxylic acid)]; an alkyl alcohol (e.g., ethanol, butyl alcohol, 2-ethylbutyl alcohol, hexyl alcohol, heptyl alcohol, octyl alcohol, and an alkyl alcohol having 9 or more carbon atoms (e.g., a $C_{3-12}$alkyl alcohol); and a hydrocarbon having 2 or more carbon atoms (e.g., a $C_{2-12}$alkane). In the liquid phase, an ester of methanol or the above alkyl alcohol with acetic acid or the above carboxylic acid (such as methyl acetate) and a dialkyl ether such as dimethyl ether are also produced secondarily. A total concentration of these by-products may be about 0.1 ppb to 100 ppm (e.g., about 0.5 ppb to 50 ppm) and preferably about 1 ppb to 10 ppm (e.g., about 2 ppb to 1 ppm) in the whole process including the liquid phase system. Thus, the concentration of these by-products may be omitted from the description or indication in each of the following steps.

The alkyl iodide having 2 or more carbon atoms (such as hexyl iodide) may have a concentration of, for example, about 0.1 ppb to 1 ppm (e.g., about 0.5 to 500 ppb) and preferably about 1 to 100 ppb. The alkanecarboxylic acid (such as formic acid or propionic acid) may have a concentration of, for example, about 0.1 to 500 ppm (e.g., about 1 to 500 ppm) and preferably about 3 to 100 ppm.

The dimethyl ether (DME) may have a concentration of not more than 0.5% by weight (e.g., about 0.1 to 1000 ppm), preferably about 1 to 500 ppm (e.g., about 2 to 300 ppm), and more preferably about 3 to 200 ppm (e.g., about 5 to 100 ppm).

Furthermore, 3-hydroxyalkanal (such as 3-hydroxybutanal) is also produced secondarily. The 3-hydroxyalkanal content of the liquid phase may be about 100 ppm or less (e.g., about 0.1 ppb to 100 ppm) and preferably about 0.5 ppb to 50 ppm. These by-products are usually increased in proportion to the square to the cube of the concentration of acetaldehyde.

Moreover, acetaldehyde and the by-products derived from acetaldehyde (for example, other aldehydes, the ketone, and the aldol condensation product) belong to permanganate reducing compounds (PRC's). Thus, it is preferred to separate and remove acetaldehyde, which is a main by-product, from the reaction mixture and to recover useful components (e.g., methyl iodide) from the process stream(s) for effective utilization. Incidentally, although the $C_{2-12}$alkyl iodide, including methyl iodide, also belongs to the PRC's, methyl iodide is excluded from the PRC's in this description and claims.

The reaction system (the liquid phase) also contains metals produced by corrosion, for example, iron, nickel, chromium, molybdenum, cobalt, and zirconium. The reaction system (the liquid phase) may contain not more than 2000 ppm (e.g., about 1 to 1000 ppm) each of these corroded metals. The total corroded metal content may be about not more than 10000 ppm (e.g., about 5 to 5000 ppm). Incidentally, a liquid stream in the downstream side of the reaction system (the liquid phase) may contain a corroded metal in the same proportion as the above. Thus, the concentration of the corroded metals in the liquid stream is omitted from the description or indication in each of the following steps.

As described above, the reaction mixture (the crude reaction liquid) contains acetic acid, lower boiling components or impurities, each having a boiling point lower than acetic acid (e.g., methyl iodide, methyl acetate, water, and acetaldehyde), and higher boiling components or impurities, each having a boiling point higher than acetic acid [e.g., a metal catalyst component (e.g., a rhodium catalyst), lithium iodide as a catalyst stabilizer, and a $C_{3-12}$alkanecarboxylic acid (e.g., propionic acid)]. Thus, in the process for producing acetic acid, a purified acetic acid is produced by removing impurities from the reaction mixture (the crude reaction liquid).

The reaction system is an exothermic reaction system that accompanies heat generation, and the reaction temperature may be controlled (or regulated) by recycling of the condensate which has been cooled or from which heat has been removed, installation of a heat-removable (or heat-removing) unit or a cooling unit (e.g., a jacket), or other means. In order to remove part of the reaction heat, a vapor (vent gas) from the reactor may be cooled in a condenser, a heat exchanger, or other means to separate the vapor into liquid components and gaseous components, and the liquid components and/or the gaseous components may be recycled to the reactor.

A gaseous phase (a line 8) from the reactor (1) is cooled and condensed in a condenser to form a condensate 10 and a noncondensable gas 9 containing carbon monoxide in relatively large quantity. The condensate 10 is returned to the reactor (1), and the noncondensable gas 9 is introduced into a gas-liquid separating pot or buffer tank S1. A noncondensable gas (an off-gas rich in carbon monoxide and methyl iodide) 11 from the tank is treated in an off-gas treatment section (15) [for example, a high-pressure absorption column (16)]. Typically, at least a portion of the noncondensable gas (off-gas) 11 containing carbon monoxide is treated in the off-gas treatment section (15). A portion of the noncondensable gas (off-gas) can partly be introduced into the flasher or evaporator (2) via a line 172 (or introduced into a liquid phase or a volatile phase (gas) in the flasher) to stabilize the catalyst in the flasher or evaporator (2) [or to prevent precipitation of the metal catalyst (e.g., a rhodium catalyst)].

For example, the gaseous phase (gaseous phase portion or gaseous stream) mixture (the line 8) from the reactor may have the following composition.

When a gaseous-phase mixture has an average molecular weight (a weighted average molecular weight) A and contains a component having a molecular weight B, the volume percent (% by volume) or weight percent (% by weight) of the component can be calculated on the basis of the weight percent (% by weight) or volume percent (% by volume) of the component. For a concentration of oxygen as one example, when the average molecular weight A of a gaseous-phase mixture is 62.2 (weighted average molecular weight) and the measured value of a volume percent D of oxygen in the gaseous-phase mixture is 7.0% by volume, a weight percent C of oxygen can be, for example, calculated from the molecular weight B (=32) of oxygen and the following equation: $(C \times 100) \times A/B = D \times 100$, as follows: $(C \times 62.2)/32 = 7$, the weight percent C of oxygen=3.6% by weight. Thus, the weight percent (% by weight) and volume percent (% by volume) of each component in the gaseous-phase mixture can be calculated from the above equation. Accordingly, the following Tables denote component concentrations in only weight percent (% by weight).

TABLE 3

| Average molecular weight 62.62 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 5% (e.g., 0.01 to 5%) | 20 ppb to 2% (e.g., 30 ppb to 1%) | 100 ppb to 0.1% (e.g., 1 to 100 ppm) |
| CO | 0.1 to 70% (e.g., 1 to 50%) | 3 to 30% | 7 to 20% |
| $CO_2$ | 0 to 5% (e.g., 0.01 to 5%) | 0.05 to 2% | 0.1 to 1% |
| $CH_4$ | 0 to 5% (e.g., 0.01 to 5%) | 0.05 to 3% | 0.1 to 2% |
| $N_2$ | 0 to 5% (e.g., 0.01 to 5%) | 0.05 to 3% | 0.1 to 2% |
| AD | 0.001 to 5% | 0.01 to 2% | 0.02 to 1% |

TABLE 3-continued

| Average molecular weight 62.62 | Range | Preferred range | More preferred range |
|---|---|---|---|
| MeOH | 0.1 ppm to 1% | 1 ppm to 0.5% | 10 ppm to 0.1% |
| MeI | 1 to 95% (e.g., 5 to 90%) | 10 to 80% | 20 to 70% |
| MA | 0.1 to 15% | 0.5 to 10% | 1 to 7% |
| $H_2O$ | 0.1 to 15% | 0.5 to 10% | 1 to 7% |
| AcOH | 1 to 50% | 2 to 40% | 5 to 30% |
| FrOH | 0 to 1% (e.g., 0.01 ppm to 1%) | 0.1 ppm to 0.5% | 1 ppm to 0.1% |
| PrOH | 0 to 1% (e.g., 0.01 ppm to 1%) | 0.01 ppm to 0.5% | 0.1 ppm to 0.1% |
| DME | 0 to 1% (e.g., 0.1 ppm to 1%) | 1 ppm to 0.5% | 10 ppm to 0.2% |
| $(CH_3)_2C{=}O$ | 0 to 1% (e.g., 0.1 ppm to 1%) | 1 ppm to 0.5% | 10 ppm to 0.2% |
| EtOH | 0 to 1% (e.g., 0.1 ppm to 1%) | 1 ppm to 0.5% | 10 ppm to 0.2% |
| EA | 0 to 1% (e.g., 0.1 ppm to 1%) | 1 ppm to 0.5% | 10 ppm to 0.2% |
| EtI | 0 to 1% (e.g., 0.1 ppm to 1%) | 1 ppm to 0.5% | 10 ppm to 0.2% |
| LiI | 0 to 0.1% (e.g., 1 ppt to 100 ppm) | 10 ppt to 10 ppm | 100 ppt to 1 ppm |
| Rh | 0 to 0.1% (e.g., 1 ppt to 100 ppm) | 10 ppt to 10 ppm | 100 ppt to 1 ppm |
| Fe | 0 to 0.1% (e.g., 1 ppt to 100 ppm) | 10 ppt to 10 ppm | 100 ppt to 1 ppm |
| Ni | 0 to 0.1% (e.g., 1 ppt to 10 ppm) | 10 ppt to 1 ppm | 100 ppt to 0.1 ppm |
| Cr | 0 to 0.1% (e.g., 1 ppt to 10 ppm) | 10 ppt to 1 ppm | 100 ppt to 0.1 ppm |
| Mo | 0 to 0.1% (e.g., 1 ppt to 10 ppm) | 10 ppt to 1 ppm | 100 ppt to 0.1 ppm |
| Zn | 0 to 0.1% (e.g., 1 ppt to 10 ppm) | 10 ppt to 1 ppm | 100 ppt to 0.1 ppm |
| Cu | 0 to 0.1% (e.g., 1 ppt to 10 ppm) | 10 ppt to 1 ppm | 100 ppt to 0.1 ppm |

For example, the condensate 10 from the condenser may have the following composition.

TABLE 4

| Average molecular weight 88.44 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.01 ppm to 1%) | 0.1 ppm to 0.1% | 1 ppm to 0.01% |
| CO | 0 to 2% (e.g., 1 ppm to 2%) | 10 ppm to 1% | 100 ppm to 0.5% |
| $CO_2$ | 0 to 1% (e.g., 0.1 ppm to 1%) | 1 ppm to 0.5% | 10 ppm to 0.2% |
| $CH_4$ | 0 to 1% (e.g., 0.1 ppm to 0.1%) | 1 ppm to 0.05% | 10 ppm to 0.01% |
| $N_2$ | 0 to 1% (e.g., 0.1 ppm to 0.1%) | 1 ppm to 0.05% | 10 ppm to 0.01% |
| AD | 0 to 1% (e.g., 1 ppm to 1%) | 10 ppm to 0.5% | 50 ppm to 0.2% |
| MeOH | 0 to 1% (e.g., 1 ppm to 1%) | 10 ppm to 0.5% | 50 ppm to 0.2% |
| MeI | 1 to 95% | 5 to 90% | 10 to 80% |
| MA | 0.1 to 20% | 0.5 to 10% | 1 to 5% |
| $H_2O$ | 0.1 to 20% | 0.5 to 10% | 1 to 7% |
| AcOH | 1 to 50% | 3 to 40% | 5 to 30% |
| FrOH | 0 to 1% (e.g., 1 ppm to 1%) | 5 ppm to 0.1% | 10 ppm to 0.01% |
| PrOH | 0 to 1% (e.g., 0.1 ppm to 1%) | 0.5 ppm to 0.1% | 1 ppm to 0.01% |
| DME | 0 to 2% (e.g., 1 ppm to 2%) | 5 ppm to 0.5% | 10 ppm to 0.1% |
| $(CH_3)_2C{=}O$ | 0 to 2% (e.g., 1 ppm to 2%) | 5 ppm to 0.5% | 10 ppm to 0.1% |
| EtOH | 0 to 2% (e.g., 1 ppm to 2%) | 5 ppm to 0.5% | 10 ppm to 0.1% |
| EA | 0 to 2% (e.g., 1 ppm to 2%) | 5 ppm to 0.5% | 10 ppm to 0.1% |
| EtI | 0 to 2% (e.g., 1 ppm to 2%) | 5 ppm to 0.5% | 10 ppm to 0.1% |
| LiI | 0 to 0.1% (e.g., 1 ppt to 100 ppm) | 10 ppt to 10 ppm | 100 ppt to 1 ppm |
| Rh | 0 to 0.1% (e.g., 1 ppt to 100 ppm) | 10 ppt to 10 ppm | 100 ppt to 1 ppm |
| Fe | 0 to 0.1% (e.g., 1 ppt to 100 ppm) | 10 ppt to 10 ppm | 100 ppt to 1 ppm |
| Ni | 0 to 0.1% (e.g., 1 ppt to 10 ppm) | 10 ppt to 1 ppm | 100 ppt to 0.1 ppm |
| Cr | 0 to 0.1% (e.g., 1 ppt to 10 ppm) | 10 ppt to 1 ppm | 100 ppt to 0.1 ppm |
| Mo | 0 to 0.1% (e.g., 1 ppt to 10 ppm) | 10 ppt to 1 ppm | 100 ppt to 0.1 ppm |
| Zn | 0 to 0.1% (e.g., 1 ppt to 10 ppm) | 10 ppt to 1 ppm | 100 ppt to 0.1 ppm |
| Cu | 0 to 0.1% (e.g., 1 ppt to 10 ppm) | 10 ppt to 1 ppm | 100 ppt to 0.1 ppm |

For example, the noncondensable gas 9 from the condenser may have the following composition.

The composition of the noncondensable gas (off-gas) 11 from the tank S1 may be substantially the same as (or similar to) the composition of the noncondensable gas 9 from the condenser.

TABLE 5

| Average molecular weight 29.86 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 10% (e.g., 0.1 ppm to 10%) | 1 ppm to 5% | 10 ppm to 2% |
| CO | 1 to 99% | 5 to 90% | 10 to 85% |
| $CO_2$ | 0.01 to 5% | 0.1 to 3% | 0.2 to 2% |
| $CH_4$ | 0.1 to 15% | 0.5 to 10% | 1 to 6% |
| $N_2$ | 0.1 to 20% | 0.5 to 15% | 1 to 10% |
| AD | 0 to 1% (e.g., 0.001 to 1%) | 0.01 to 0.5% | 0.02 to 0.2% |
| MeOH | 0 to 1% (e.g., 1 ppm to 1%) | 5 ppm to 0.5% | 10 ppm to 0.1% |
| MeI | 1 to 90% (e.g., 5 to 80%) | 10 to 70% | 20 to 50% |
| MA | 0 to 5% (e.g., 0.001 to 5%) | 0.01 to 1% | 0.05 to 0.5% |
| $H_2O$ | 0 to 5% (e.g., 0.001 to 5%) | 0.01 to 1% | 0.05 to 0.5% |
| AcOH | 0 to 5% (e.g., 0.001 to 5%) | 0.01 to 1% | 0.05 to 0.5% |
| FrOH | 0 to 1% (e.g., 0.1 ppm to 0.5%) | 1 ppm to 0.2% | 10 ppm to 0.1% |
| PrOH | 0 to 1% (e.g., 0.1 ppm to 0.5%) | 0.5 ppm to 0.2% | 1 ppm to 0.1% |
| DME | 0 to 1% (e.g., 0.1 ppm to 0.5%) | 1 ppm to 0.2% | 10 ppm to 0.1% |
| $(CH_3)_2C{=}O$ | 0 to 1% (e.g., 0.1 ppm to 1%) | 1 ppm to 0.1% | 5 ppm to 0.05% |
| EtOH | 0 to 1% (e.g., 0.1 ppm to 1%) | 1 ppm to 0.1% | 5 ppm to 0.05% |
| EA | 0 to 1% (e.g., 0.1 ppm to 1%) | 1 ppm to 0.1% | 5 ppm to 0.05% |
| EtI | 0 to 1% (e.g., 0.1 ppm to 1%) | 1 ppm to 0.1% | 5 ppm to 0.05% |
| LiI | 0 to 0.1% (e.g., 1 ppt to 10 ppm) | 10 ppt to 1 ppm | 100 ppt to 0.1 ppm |
| Rh | 0 to 0.1% (e.g., 1 ppt to 10 ppm) | 10 ppt to 1 ppm | 100 ppt to 0.1 ppm |
| Fe | 0 to 0.1% (e.g., 1 ppt to 10 ppm) | 10 ppt to 1 ppm | 100 ppt to 0.1 ppm |
| Ni | 0 to 0.1% (e.g., 1 ppt to 1 ppm) | 10 ppt to 0.1 ppm | 100 ppt to 0.01 ppm |
| Cr | 0 to 0.1% (e.g., 1 ppt to 1 ppm) | 10 ppt to 0.1 ppm | 100 ppt to 0.01 ppm |
| Mo | 0 to 0.1% (e.g., 1 ppt to 1 ppm) | 10 ppt to 0.1 ppm | 100 ppt to 0.01 ppm |
| Zn | 0 to 0.1% (e.g., 1 ppt to 1 ppm) | 10 ppt to 0.1 ppm | 100 ppt to 0.01 ppm |
| Cu | 0 to 0.1% (e.g., 1 ppt to 1 ppm) | 10 ppt to 0.1 ppm | 100 ppt to 0.01 ppm |

The reaction mixture 12 from the reactor (1) is introduced or fed to the flasher (evaporator) (2) via a line 12 for flash evaporation to form a volatile phase (2A) and a less-volatile phase (2B); the volatile phase (2A) contains the product acetic acid, methyl iodide, acetaldehyde, methyl acetate, water, or other components, and the less-volatile phase (2B) contains the rhodium catalyst and lithium iodide.

For example, the reaction mixture 12 may have the following composition.

TABLE 6

| Average molecular weight 65.23 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 1%) | 1 ppm to 0.5% (e.g., 10 ppm to 0.2%) | 100 ppm to 0.1% |
| CO | 0.1 ppm to 5% (e.g., 1 ppm to 2%) | 10 ppm to 1% | 100 ppm to 0.5% |
| $CO_2$ | 0 to 1% (e.g., 0.1 ppm to 1%) | 1 ppm to 0.5% (e.g., 10 ppm to 0.2%) | 100 ppm to 0.1% |
| $CH_4$ | 0 to 1% (e.g., 0.1 ppm to 1%) | 1 ppm to 0.5% (e.g., 10 ppm to 0.2%) | 100 ppm to 0.1% |
| $N_2$ | 0 to 1% (e.g., 0.1 ppm to 1%) | 1 ppm to 0.5% (e.g., 10 ppm to 0.2%) | 100 ppm to 0.1% |
| AD | 0 to 1% (e.g., 0.1 ppm to 1%) | 1 ppm to 0.5% (e.g., 10 ppm to 0.2%) | 100 ppm to 0.1% |
| MeOH | 0 to 1% (e.g., 0.1 ppm to 1%) | 1 ppm to 0.5% (e.g., 10 ppm to 0.2%) | 10 ppm to 0.25% (e.g., 50 ppm to 0.2%), e.g., 100 ppm to 0.1% |

TABLE 6-continued

| Average molecular weight 65.23 | Range | Preferred range | More preferred range |
|---|---|---|---|
| MeI | 1 to 20% (e.g., 2 to 17%) | 4 to 15% | 5 to 13% |
| MA | 0.5 to 7% (e.g., 1 to 4%) | 1.5 to 5% (e.g., 1.5 to 3%) | 1.7 to 4% (e.g., 1.8 to 2.5%) |
| $H_2O$ | 0.1 to 12% (e.g., 0.5 to 5%) | 0.8 to 3% | 1 to 2.5% |
| AcOH | 30 to 95% (e.g., 40 to 90%) | 50 to 85% | 60 to 80% |
| HI | 0 to 1% (e.g., 0.001 to 1%), e.g., 0.002 to 0.8% (e.g., 0.01 to 0.7%) | 0.003 to 0.5% (e.g., 0.02 to 0.5%) | 0.005 to 0.3% (e.g., 0.05 to 0.3%), e.g., 0.05 to 0.2% |
| FrOH | 0 to 1% (e.g., 1 ppm to 0.1%) | 5 to 500 ppm | 10 to 200 ppm |
| PrOH | 0 to 1% (e.g., 1 ppm to 0.2%) | 5 ppm to 0.1% (e.g., 10 to 500 ppm) | 30 to 300 ppm |
| DME | 0 to 1% (e.g., 0.1 ppm to 0.5%) | 1 ppm to 0.3% (e.g., 5 ppm to 0.1%) | 10 to 500 ppm (e.g., 10 to 300 ppm), e.g., 10 to 100 ppm |
| $(CH_3)_2C{=}O$ | 0 to 1% (e.g., 1 ppm to 0.1%) | 10 to 300 ppm | 20 to 100 ppm |
| EtOH | 0 to 1% (e.g., 1 ppm to 0.1%) | 10 to 300 ppm | 20 to 100 ppm |
| EA | 0 to 1% (e.g., 1 ppm to 0.1%) | 10 to 300 ppm | 20 to 100 ppm |
| EtI | 0 to 1% (e.g., 1 ppm to 0.1%) | 10 to 300 ppm | 20 to 100 ppm |
| LiI | 0.1 to 25% (e.g., 1 to 20%) | 5 to 23% (e.g., 5 to 17%) | 7 to 20% (e.g., 8 to 15%) |
| Rh | 100 ppm to 0.5% | 200 ppm to 0.2% | 500 to 1500 ppm |
| Fe | 0 to 1% (e.g., 10 ppm to 1%) | 100 ppm to 0.7% | 500 ppm to 0.5% |
| Ni | 0 to 1% (e.g., 1 ppm to 0.5%) | 10 ppm to 0.2% | 100 ppm to 0.1% |
| Cr | 0 to 1% (e.g., 1 ppm to 0.5%) | 10 ppm to 0.2% | 100 ppm to 0.1% |
| Mo | 0 to 1% (e.g., 1 ppm to 0.5%) | 10 ppm to 0.2% | 50 ppm to 0.05% |
| Zn | 0 to 1% (e.g., 10 ppm to 1%) | 100 ppm to 0.7% | 500 ppm to 0.5% |
| Cu | 0 to 1% (e.g., 0.01 ppm to 0.1%) | 0.1 to 100 ppm | 1 to 30 ppm |

(2) Flash Evaporation Step

In the flash evaporation step (2), as described above, the reaction mixture is separated into the volatile phase (2A) and the less-volatile phase (2B), and the less-volatile phase or catalyst liquid (2B) is recycled to the reactor of the reaction step (1) via the recycle line 21.

For example, the less-volatile phase (2B) (the line 21) may have the following composition.

TABLE 7

| Average molecular weight 63.47 | Range | Preferred range | More preferred range |
|---|---|---|---|
| Metal catalyst | 200 ppm to 0.5% | 500 ppm to 0.4% | 0.1 to 0.3% |
| Ionic iodide | 1 to 60% (e.g., 2 to 50%) | 3 to 40% (e.g., 5 to 35%) | 5 to 25% (e.g., , 8 to 20%) |
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 0.1% (e.g., 1 ppt to 100 ppm) | 30 ppt to 2 ppm | 50 ppt to 1 ppm |
| CO | 0 to 1% (e.g., 5000 ppt to 30 ppm) | 300 ppb to 20 ppm (e.g., 1000 ppb to 10 ppm) | 500 ppb to 5 ppm (e.g., 200 ppb to 1 ppm) |
| $CO_2$ | 0 to 0.1% (e.g., 1 ppt to 100 ppm) | 30 ppt to 2 ppm | 50 ppt to 1 ppm |
| $CH_4$ | 0 to 0.1% (e.g., 1 ppt to 100 ppm) | 30 ppt to 2 ppm | 50 ppt to 1 ppm |
| $N_2$ | 0 to 0.1% (e.g., 1 ppt to 100 ppm) | 30 ppt to 2 ppm | 50 ppt to 1 ppm |
| AD | 0 to 1500 ppm (e.g., 10 to 0.1%) | 5 to 700 ppm (e.g., 30 to 500 ppm) | 10 to 400 ppm (e.g., 20 to 200 ppm), e.g., 50 to 300 ppm |
| MeOH | 0 to 1% (e.g., 0 to 0.8%) | 0 to 0.3% | 0 to 0.2% |
| MeI | 0.01 to 8% (e.g., 0.05 to 6%) | 0.1 to 4% (e.g., 0.5 to 2.5%) | 0.3 to 2.5% (e.g., 0.5 to 2%) |
| MA | 0.6 to 20% (e.g., 0.7 to 15%) | 0.7 to 10% (e.g., 0.8 to 5%) | 0.9 to 3% (e.g., 0.9 to 2%) |
| $H_2O$ | 0.1 to 12% (e.g., 0.5 to 10%) | 0.7 to 8% (e.g., 0.8 to 5%) | 0.8 to 3% (e.g., 0.8 to 2%) |
| AcOH | 35 to 95% (e.g., 45 to 90%) | 60 to 90% | 50 to 85% |
| HI | 0.001 to 1% (e.g., 0.01 to 0.7%) | 0.003 to 0.6% (e.g., 0.02 to 0.5%) | 0.005 to 0.4% (e.g., 0.05 to 0.3%) |
| FrOH | 0 to 0.1% (e.g., 1 ppm to 0.1%) | 5 to 500 ppm | 10 to 200 ppm |
| PrOH | 0 to 0.2% (e.g., 1 ppm to 0.2%) | 5 ppm to 0.1% (e.g., 10 to 500 ppm) | 30 to 300 ppm |
| DME | 0 to 0.5% (e.g., 0.1 to 0.1%) | 1 to 500 ppm (e.g., 3 to 200 ppm) | 5 to 500 ppm (e.g., 10 to 300 ppm), e.g., 5 to 100 ppm |
| $(CH_3)_2C{=}O$ | 0 to 0.1% (e.g., 0.01 ppm to 0.1%) | 0.1 to 100 ppm | 1 to 50 ppm |
| EtOH | 0 to 0.1% (e.g., 0.01 ppm to 0.1%) | 0.1 to 100 ppm | 1 to 50 ppm |
| EA | 0 to 0.1% (e.g., 0.01 ppm to 0.1%) | 0.1 to 100 ppm | 1 to 50 ppm |
| EtI | 0 to 0.1% (e.g., 0.01 ppm to 0.1%) | 0.1 to 100 ppm | 1 to 50 ppm |
| LiI | 0.1 to 33% (e.g., 1 to 26%) | 5 to 30% (e.g., 6 to 21%) | 8 to 27% (e.g., 8 to 24%), e.g., 9 to 19% |

TABLE 7-continued

| Average molecular weight 63.47 | Range | Preferred range | More preferred range |
|---|---|---|---|
| Rh | 150 to 7000 ppm | 300 to 2500 ppm | 600 to 1800 ppm |
| Fe | 0 to 1% (e.g., 10 ppm to 1%) | 100 ppm to 0.7% | 500 ppm to 0.5% |
| Ni | 0 to 0.5% (e.g., 1 ppm to 0.5%) | 10 ppm to 0.2% | 100 ppm to 0.1% |
| Cr | 0 to 0.5% (e.g., 1 ppm to 0.5%) | 10 ppm to 0.2% | 100 ppm to 0.1% |
| Mo | 0 to 0.5% (e.g., 1 ppm to 0.5%) | 10 ppm to 0.2% | 50 ppm to 0.05% |
| Zn | 0 to 1% (e.g., 10 ppm to 1%) | 100 ppm to 0.7% | 500 ppm to 0.5% |
| Cu | 0 to 0.1% (e.g., 0.01 ppm to 0.1%) | 0.1 to 100 ppm | 1 to 30 ppm |

The less-volatile phase (2B) also contains metals produced by corrosion, for example, iron, nickel, chromium, molybdenum, cobalt, zirconium, zinc, and copper. The less-volatile phase (2B) may contain about not more than 2000 ppm (e.g., about 1 to 1000 ppm) each of these corroded metals.

Further, the less-volatile phase or catalyst liquid (2B) is mixed with the portion 54 of the condensate (the portion of the condensate rich in acetic acid) of the second overhead 51 from the distillation column (dehydration column) of the second distillation step (5) at the recycle line 21, and the mixture is recycled to the reactor (1) of the reaction step (1).

For example, the condensate 54 may have the following composition.

Mo, zinc Zn, and copper Cu in a condensate may be in the ranges as described in the above Table 8.

At least a portion of the volatile phase (2A) from the flasher (evaporator) (2) is fed to a distillation column (splitter column) of the first distillation step (3) via a feed line 23. A portion 24 of the volatile phase from the flasher (evaporator) (2) is cooled and condensed in first and second condensers sequentially to form condensates 26, 28 and noncondensable gases (off-gases) 25, 30. The condensates 26, 28 are recycled to the reactor (1) via a hold tank T1 and a recycle line 27, thereby cooling the reaction system of the reactor (1).

A gaseous phase 29 from the hold tank T1 is cooled in the second condenser, and the noncondensable gas (off-gas) 30 from the second condenser is fed to the off-gas treatment

TABLE 8

| Average molecular weight 56.08 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppt to 1%) | 0.1 ppb to 0.1% (e.g., 1 ppb to 100 ppm) | 1 to 10 ppm |
| CO | 0 to 1% (e.g., 0.1 ppm to 1%) | 1 ppm to 0.5% (e.g., 2 ppm to 0.1%) | 10 to 100 ppm |
| $CO_2$ | 0 to 1% (e.g., 0.1 ppt to 1%) | 0.1 ppb to 0.1% (e.g., 1 ppb to 100 ppm) | 1 to 10 ppm |
| $CH_4$ | 0 to 1% (e.g., 0.1 ppt to 1%) | 0.1 ppb to 0.1% (e.g., 1 ppb to 100 ppm) | 1 to 10 ppm |
| $N_2$ | 0 to 1% (e.g., 0.1 ppt to 1%) | 1 ppm to 0.5% (e.g., 2 ppm to 0.1%) | 10 to 100 ppm |
| AD | 10 ppm to 0.5% | 50 ppm to 0.2% | 100 ppm to 0.1% |
| MeOH | 0 to 2% (e.g., 10 ppm to 2%) | 50 ppm to 1% | 100 ppm to 0.5% |
| MeI | 1 to 30% | 2 to 20% | 5 to 15% |
| MA | 1 to 20% | 2 to 15% | 3 to 12% |
| $H_2O$ | 1 to 20% | 2 to 15% | 3 to 10% |
| AcOH | 30 to 95% | 50 to 90% | 60 to 85% |
| FrOH | 0 to 1% (e.g., 0.1 ppm to 1%) | 10 ppm to 0.1% | 30 to 500 ppm |
| PrOH | 0 to 1% (e.g., 0.1 ppm to 0.1%) | 1 to 100 ppm | 5 to 50 ppm |
| DME | 0 to 2% (e.g., 0.1 ppm to 2%) | 1 ppm to 1% | 10 ppm to 0.2% |
| $(CH_3)_2C=O$ | 0 to 1% (e.g., 0.1 ppm to 1%) | 1 ppm to 0.5% | 10 ppm to 0.1% |
| EtOH | 0 to 1% (e.g., 0.1 ppm to 1%) | 1 ppm to 0.5% | 10 ppm to 0.1% |
| EA | 0 to 1% (e.g., 0.1 ppm to 1%) | 1 ppm to 0.5% | 10 ppm to 0.1% |
| EtI | 0 to 1% (e.g., 0.1 ppm to 1%) | 1 ppm to 0.5% | 10 ppm to 0.1% |
| LiI | 0 to 0.1% (e.g., 0.001 ppb to 10 ppm) | 0.01 ppb to 1 ppm | 0.1 ppb to 0.1 ppm |
| Rh | 0 to 0.1% (e.g., 0.001 ppb to 10 ppm) | 0.01 ppb to 1 ppm | 0.1 ppb to 0.1 ppm |
| Fe | 0 to 0.1% (e.g., 10 ppt to 10 ppm) | 100 ppt to 5 ppm | 1000 ppt to 1 ppm |
| Ni | 0 to 0.1% (e.g., 1 ppt to 1 ppm) | 10 ppt to 0.1 ppm | 100 ppt to 0.05 ppm |
| Cr | 0 to 0.1% (e.g., 1 ppt to 1 ppm) | 10 ppt to 0.1 ppm | 100 ppt to 0.01 ppm |
| Mo | 0 to 0.1% (e.g., 1 ppt to 1 ppm) | 10 ppt to 0.1 ppm | 100 ppt to 0.01 ppm |
| Zn | 0 to 0.1% (e.g., 1 ppt to 1 ppm) | 10 ppt to 0.1 ppm | 100 ppt to 0.01 ppm |
| Cu | 0 to 0.1% (e.g., 1 ppt to 1 ppm) | 10 ppt to 0.1 ppm | 100 ppt to 0.01 ppm |

Unless otherwise specifically noted hereinafter, the concentrations of iron Fe, nickel Ni, chromium Cr, molybdenum section (15) (a low-pressure absorption column (17)). Incidentally, as described later, a noncondensable gas 192 from the off-gas treatment section (15) is also fed between the first condenser and the second condenser, and is cooled and condensed in the second condenser. To the hold tank T1 is also fed a condensate (a condensate rich in methyl iodide) 193 from the off-gas treatment section (15).

As described above, a portion 172 of an overhead stream 171 from the off-gas treatment section (15) (the high-pressure absorption column (16)) is introduced to the flasher (catalyst separation column) (2).

The flash evaporation may include a thermostatic flash in which the reaction mixture is heated and depressurized, an adiabatic flash in which the reaction mixture is depressurized without heating, or a combination of these flash conditions. By such a flash evaporation, the reaction mixture may be separated into the vapor phase and the liquid phase. For example, the flash distillation (evaporation) may be carried out at a temperature of about 100 to 250° C. (e.g., about 120 to 230° C.), preferably about 150 to 220° C. (e.g., about 160 to 210° C.), and more preferably about 170 to 200° C. The flash distillation (evaporation) may be carried out at a pressure (absolute pressure) of about 0.03 to 1 MPa (e.g., about 0.05 to 1 MPa), preferably about 0.07 to 0.7 MPa, and more preferably about 0.1 to 0.5 MPa (e.g., about 0.15 to 0.4 MPa). Moreover, the less-volatile phase or catalyst liquid (2B) may have a temperature of, for example, about 80 to 200° C. (e.g., about 90 to 180° C.), preferably about 100 to 170° C. (e.g., about 120 to 160° C.), and more preferably about 130 to 160° C. Under such a relatively high temperature (and high pressure) condition, hydrogen iodide is easily produced, and iodine is easily formed depending on the concentration of oxygen. The present invention allows effectively reduced formation of iodine even if hydrogen iodide is produced.

For example, the volatile phase (2A) (lines 23, 24) may have the following composition.

TABLE 9

| Average molecular weight 70.17 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.1 ppm to 1%) | 1 ppm to 0.1% | 10 ppm to 0.01% |
| CO | 100 ppm to 3% | 0.1 to 2% | 0.2 to 1% |
| $CO_2$ | 10 ppm to 2% | 100 ppm to 1% (e.g., 0.1 to 0.5%) | 0.02 to 0.5% |
| $CH_4$ | 0 to 1% (e.g., 1 ppm to 1%) | 10 ppm to 0.5% | 100 ppm to 0.1% |
| $N_2$ | 0 to 1% (e.g., 1 ppm to 1%) | 10 ppm to 0.5% | 100 ppm to 0.1% |
| AD | 0 to 1% (e.g., 0.01 to 0.5%) | 0.02 to 0.2% (e.g., 0.03 to 0.15%) | 0.04 to 0.1% |
| MeOH | 0 to 2% (e.g., 10 ppm to 2%) | 50 ppm to 1.5% (e.g., 100 ppm to 1%) | 500 ppm to 0.7% (e.g., 0.1% to 0.5%) |
| MeI | 10 to 60% | 15 to 50% | 20 to 45% |
| MA | 1 to 15% (e.g., 2 to 12%) | 4 to 10% | 5 to 8% |
| $H_2O$ | 0.1 to 10% | 0.8 to 8% | 1.5 to 4% |
| AcOH | 20 to 80% (e.g., 30 to 75%) | 40 to 70% (e.g., 50 to 65%) | 60 to 70% |
| HI | 0 to 1% (e.g., 0.1 ppm to 1%) | 1 ppm to 0.5% (e.g., 5 ppm to 0.3%) | 10 ppm to 0.1% |
| LiI | 0 to 1% (e.g., 0.1 ppm to 1%) | 1 ppm to 0.5% (e.g., 10 ppm to 0.1%) | 30 ppm to 0.03% |
| FrOH | 0 to 1% (e.g., 0.1 ppm to 0.1%) | 1 to 100 ppm | 5 to 50 ppm |
| PrOH | 0 to 1% (e.g., 0.1 ppm to 0.1%) | 1 to 300 ppm (e.g., 5 to 200 ppm) | 10 to 100 ppm |
| DME | 0 to 1% (e.g., 0.1 ppm to 0.1%) | 1 to 700 ppm (e.g., 1 to 100 ppm) | 5 to 500 ppm (e.g., 5 to 50 ppm) |
| $(CH_3)_2C{=}O$ | 0 to 1% (e.g., 1 ppm to 0.1%) | 10 to 500 ppm | 20 to 100 ppm |
| EtOH | 0 to 1% (e.g., 1 ppm to 0.1%) | 10 to 500 ppm | 20 to 100 ppm |
| EA | 0 to 1% (e.g., 1 ppm to 0.1%) | 10 to 500 ppm | 20 to 100 ppm |
| EtI | 0 to 1% (e.g., 1 ppm to 0.1%) | 10 to 500 ppm | 20 to 100 ppm |
| LiI | 0 to 0.5% (e.g., 1 ppb to 0.1%) | 0.01 to 500 ppm | 0.1 to 200 ppm |
| Rh | 0 to 0.5% (e.g., 1 ppb to 0.1%) | 0.01 to 500 ppm | 0.1 to 100 ppm |
| Fe | 0 to 1% (e.g., 0.1 ppm to 0.2%) | 1 ppm to 0.1% | 10 to 500 ppm |
| Ni | 0 to 0.5% (e.g., 0.1 ppm to 0.1%) | 1 to 500 ppm | 10 to 200 ppm |
| Cr | 0 to 0.5% (e.g., 0.1 ppm to 0.1%) | 1 to 500 ppm | 10 to 200 ppm |
| Mo | 0 to 0.5% (e.g., 0.01 to 500 ppm) | 0.1 to 200 ppm | 1 to 100 ppm |
| Zn | 0 to 1% (e.g., 0.1 ppm to 0.2%) | 1 ppm to 0.1% | 10 to 500 ppm |
| Cu | 0 to 0.1% (e.g., 0.001 to 100 ppm) | 0.01 to 50 ppm | 0.1 to 10 ppm |

For example, the condensate 26 from the first condenser may have the following composition.

The composition of the condensate (recycle line) 27 recycled from the hold tank T1 to the reactor (1) may be substantially the same as (or similar to) the composition of the condensate 26 from the first condenser. Moreover, the composition of the above condensate (recycle line) 27 may have a component ratio (content of each component) obtained or calculated from the weighted average of the component ratio of the condensate 26 from the first condenser and the component ratio of the condensate 28 from the second condenser.

TABLE 10

| Average molecular weight 70.60 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.01 ppm to 1%) | 0.1 ppm to 0.1% | 1 ppm to 0.01% |
| CO | 0 to 1% (e.g., 1 ppm to 1%) | 10 ppm to 0.5% | 100 ppm to 0.1% |
| $CO_2$ | 0 to 1% (e.g., 1 ppm to 1%) | 10 ppm to 0.5% | 100 ppm to 0.1% |
| $CH_4$ | 0 to 1% (e.g., 1 ppm to 1%) | 10 ppm to 0.5% | 100 ppm to 0.1% |
| $N_2$ | 0 to 1% (e.g., 1 ppm to 1%) | 10 ppm to 0.5% | 100 ppm to 0.1% |
| AD | 0 to 1% (e.g., 1 ppm to 1%) | 10 ppm to 0.5% | 100 ppm to 0.1% |
| MeOH | 0 to 1% (e.g., 1 ppm to 1%) | 10 ppm to 0.5% | 100 ppm to 0.1% |
| MeI | 1 to 95% | 5 to 90% | 10 to 70% |
| MA | 0.1 to 40% | 0.5 to 20% | 1 to 10% |
| $H_2O$ | 0.1 to 40% | 0.5 to 20% | 1 to 7% |
| AcOH | 1 to 95% | 10 to 90% | 30 to 80% |
| HI | 0 to 0.5% (e.g., 0.01 ppm to 0.1%) | 0.1 ppm to 0.01% | 1 ppm to 0.001% |
| LiI | 0 to 0.5% (e.g., 0.01 ppm to 0.1%) | 0.1 ppm to 0.05% | 1 ppm to 0.01% |
| FrOH | 0 to 0.5% (e.g., 0.01 ppm to 0.1%) | 0.1 ppm to 0.05% | 1 ppm to 0.01% |
| PrOH | 0 to 1% (e.g., 0.1 ppm to 1%) | 1 ppm to 0.1% | 2 ppm to 0.01% |
| DME | 0 to 1% (e.g., 0.01 ppm to 1%) | 0.1 ppm to 0.1% | 1 ppm to 0.01% |
| $(CH_3)_2C{=}O$ | 0 to 1% (e.g., 0.1 ppm to 1%) | 1 ppm to 0.1% | 5 ppm to 0.05% |
| EtOH | 0 to 1% (e.g., 0.1 ppm to 1%) | 1 ppm to 0.1% | 5 ppm to 0.05% |
| EA | 0 to 1% (e.g., 0.1 ppm to 1%) | 1 ppm to 0.1% | 5 ppm to 0.05% |
| EtI | 0 to 1% (e.g., 0.1 ppm to 1%) | 1 ppm to 0.1% | 5 ppm to 0.05% |
| LiI | 0 to 0.1% (e.g., 0.1 ppt to 10 ppm) | 1 ppt to 1 ppm | 10 ppt to 0.1 ppm |
| Rh | 0 to 0.1% (e.g., 0.1 ppt to 10 ppm) | 1 ppt to 1 ppm | 10 ppt to 0.1 ppm |
| Fe | 0 to 0.5% (e.g., 0.1 ppm to 0.2%) | 1 ppm to 0.1% | 10 to 500 ppm |
| Ni | 0 to 0.2% (e.g., 0.1 ppm to 0.1%) | 1 to 500 ppm | 10 to 200 ppm |
| Cr | 0 to 0.2% (e.g., 0.1 ppm to 0.1%) | 1 to 500 ppm | 10 to 200 ppm |
| Mo | 0 to 0.1% (e.g., 0.01 to 500 ppm) | 0.1 to 200 ppm | 1 to 100 ppm |
| Zn | 0 to 0.5% (e.g., 0.1 ppm to 0.2%) | 1 ppm to 0.1% | 10 to 500 ppm |
| Cu | 0 to 0.1% (e.g., 0.001 to 100 ppm) | 0.01 to 50 ppm | 0.1 to 10 ppm |

For example, the noncondensable gas (off-gas) 25 from the first condenser may have the following composition.

TABLE 11

| Average molecular weight 46.42 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.1 to 10% | 0.2 to 5% | 0.5 to 5% |
| CO | 1 to 99% | 5 to 90% | 10 to 80% |
| $CO_2$ | 0.1 to 20% | 0.2 to 15% | 0.5 to 8% |
| $CH_4$ | 0.1 to 20% | 0.2 to 15% | 0.5 to 8% |
| $N_2$ | 0.1 to 20% | 0.2 to 15% | 0.5 to 8% |
| AD | 0.001 to 3% | 0.01 to 1% | 0.02 to 0.5% |
| MeOH | 0 to 1% (e.g., 1 ppm to 1%) | 5 ppm to 0.5% | 10 ppm to 0.1% |
| MeI | 1 to 95% | 10 to 90% | 20 to 80% |
| MA | 0.1 to 20% | 0.5 to 10% | 1 to 5% |
| $H_2O$ | 0.01 to 2% | 0.05 to 1% | 0.1 to 0.5% |
| AcOH | 0.1 to 20% | 0.5 to 10% | 1 to 5% |
| FrOH | 0 to 1% (e.g., 0.1 ppm to 0.5%) | 1 ppm to 0.2% | 10 ppm to 0.1% |
| PrOH | 0 to 1% (e.g., 0.1 ppm to 0.5%) | 1 ppm to 0.2% | 10 ppm to 0.1% |
| DME | 0 to 1% (e.g., 0.1 ppm to 1%) | 1 ppm to 0.1% | 5 ppm to 0.05% |
| $(CH_3)_2C{=}O$ | 0 to 1% (e.g., 0.1 ppm to 1%) | 1 ppm to 0.1% | 5 ppm to 0.05% |
| EtOH | 0 to 1% (e.g., 0.1 ppm to 1%) | 1 ppm to 0.1% | 5 ppm to 0.05% |
| EA | 0 to 1% (e.g., 0.1 ppm to 1%) | 1 ppm to 0.1% | 5 ppm to 0.05% |
| EtI | 0 to 1% (e.g., 0.1 ppm to 1%) | 1 ppm to 0.1% | 5 ppm to 0.05% |
| LiI | 0 to 0.1% (e.g., 0.1 ppt to 100 ppm) | 1 ppt to 10 ppm | 10 ppt to 1 ppm |
| Rh | 0 to 0.1% (e.g., 0.1 ppt to 100 ppm) | 1 ppt to 10 ppm | 10 ppt to 1 ppm |
| Fe | 0 to 0.1% (e.g., 0.1 ppt to 100 ppm) | 1 ppt to 10 ppm | 10 ppt to 1 ppm |
| Ni | 0 to 0.1% (e.g., 0.1 ppt to 100 ppm) | 1 ppt to 10 ppm | 10 ppt to 1 ppm |
| Cr | 0 to 0.1% (e.g., 0.1 ppt to 100 ppm) | 1 ppt to 10 ppm | 10 ppt to 1 ppm |
| Mo | 0 to 0.1% (e.g., 0.1 ppt to 100 ppm) | 1 ppt to 10 ppm | 10 ppt to 1 ppm |

TABLE 11-continued

| Average molecular weight 46.42 | Range | Preferred range | More preferred range |
|---|---|---|---|
| Zn | 0 to 0.1% (e.g., 0.1 ppt to 100 ppm) | 1 ppt to 10 ppm | 10 ppt to 1 ppm |
| Cu | 0 to 0.1% (e.g., 0.1 ppt to 100 ppm) | 1 ppt to 10 ppm | 10 ppt to 1 ppm |

For example, the condensate 28 from the second condenser may have the following composition.

TABLE 12

| Average molecular weight 111.15 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 2% (e.g., 0.01 ppm to 1%) | 0.1 ppm to 0.1% | 1 ppm to 0.01% |
| CO | 0 to 2% (e.g., 1 ppm to 1%) | 10 ppm to 0.5% | 100 ppm to 0.1% |
| $CO_2$ | 0 to 2% (e.g., 1 ppm to 1%) | 10 ppm to 0.5% | 100 ppm to 0.1% |
| $CH_4$ | 0 to 1% (e.g., 0.1 ppm to 0.1%) | 1 ppm to 0.05% | 10 ppm to 0.01% |
| $N_2$ | 0 to 1% (e.g., 0.1 ppm to 0.1%) | 1 ppm to 0.05% | 10 ppm to 0.01% |
| AD | 0 to 1% (e.g., 0.1 ppm to 0.1%) | 1 ppm to 0.05% | 10 ppm to 0.01% |
| MeOH | 0 to 1% (e.g., 0.1 ppm to 0.1%) | 1 ppm to 0.05% | 10 ppm to 0.01% |
| MeI | 1 to 95% (e.g., 5 to 90%) | 10 to 85% (e.g., 50 to 85%) | 70 to 83% |
| MA | 0.1 to 40% | 0.5 to 20% | 1 to 10% |
| $H_2O$ | 0.1 to 40% (e.g., 0.3 to 20%) | 0.5 to 20% (e.g., 1 to 7%) | 0.7 to 5% |
| AcOH | 1 to 95% (e.g., 10 to 90%) | 5 to 30% | 7 to 15% |
| FrOH | 0 to 1% (e.g., 0.01 ppm to 0.1%) | 0.1 ppm to 0.01% | 1 ppm to 0.001% |
| PrOH | 0 to 1% (e.g., 0.01 ppm to 0.1%) | 0.1 ppm to 0.05% | 1 ppm to 0.01% |
| DME | 0 to 1% (e.g., 0.01 ppm to 0.1%) | 0.1 ppm to 0.05% | 1 ppm to 0.01% |
| $(CH_3)_2C{=}O$ | 0 to 1% (e.g., 0.1 ppm to 0.1%) | 1 ppm to 0.05% | 5 ppm to 0.05% |
| EtOH | 0 to 1% (e.g., 0.1 ppm to 0.1%) | 1 ppm to 0.05% | 5 ppm to 0.05% |
| EA | 0 to 1% (e.g., 0.1 ppm to 0.1%) | 1 ppm to 0.05% | 5 ppm to 0.05% |
| EtI | 0 to 1% (e.g., 0.1 ppm to 0.1%) | 1 ppm to 0.05% | 5 ppm to 0.05% |
| LiI | 0 to 0.1% (e.g., 0.1 ppt to 10 ppm) | 1 ppt to 1 ppm | 10 ppt to 0.1 ppm |
| Rh | 0 to 0.1% (e.g., 0.1 ppt to 10 ppm) | 1 ppt to 1 ppm | 10 ppt to 0.1 ppm |

For example, the noncondensable gas 30 from the second condenser may have the following composition.

TABLE 13

| Average molecular weight 41.38 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01 to 5% | 0.05 to 2% | 0.1 to 1% |
| CO | 1 to 99% | 5 to 80% | 10 to 70% |
| $CO_2$ | 0.1 to 20% | 0.5 to 15% | 1 to 10% |
| $CH_4$ | 0.1 to 20% | 0.5 to 15% | 1 to 10% |
| $N_2$ | 0.1 to 20% | 0.5 to 15% | 1 to 10% |
| AD | 0.001 to 3% | 0.01 to 1% | 0.1 to 0.5% |
| MeOH | 0 to 1% (e.g., 1 ppm to 1%) | 5 ppm to 0.5% | 10 ppm to 0.1% |
| MeI | 1 to 95% | 10 to 90% | 20 to 80% |
| MA | 0.01 to 20% | 0.1 to 10% | 0.5 to 5% |
| $H_2O$ | 0.01 to 10% | 0.02 to 1% | 0.05 to 0.5% |
| AcOH | 0.001 to 10% | 0.01 to 1% | 0.05 to 0.5% |
| FrOH | 0 to 1% (e.g., 0.1 ppm to 0.5%) | 1 ppm to 0.2% | 10 ppm to 0.1% |
| PrOH | 0 to 1% (e.g., 0.1 ppm to 0.5%) | 1 ppm to 0.2% | 10 ppm to 0.1% |
| DME | 0 to 1% (e.g., 0.1 ppm to 1%) | 1 ppm to 0.1% | 5 ppm to 0.05% |
| $(CH_3)_2C{=}O$ | 0 to 1% (e.g., 0.1 ppm to 1%) | 1 ppm to 0.1% | 5 ppm to 0.05% |
| EtOH | 0 to 1% (e.g., 0.1 ppm to 1%) | 1 ppm to 0.1% | 5 ppm to 0.05% |
| EA | 0 to 1% (e.g., 0.1 ppm to 1%) | 1 ppm to 0.1% | 5 ppm to 0.05% |
| EtI | 0 to 1% (e.g., 0.1 ppm to 1%) | 1 ppm to 0.1% | 5 ppm to 0.05% |

TABLE 13-continued

| Average molecular weight 41.38 | Range | Preferred range | More preferred range |
|---|---|---|---|
| LiI | 0 to 0.1% (e.g., 0.1 ppt to 10 ppm) | 1 ppt to 1 ppm | 10 ppt to 0.1 ppm |
| Rh | 0 to 0.1% (e.g., 0.1 ppt to 10 ppm) | 1 ppt to 1 ppm | 10 ppt to 0.1 ppm |

As the flasher (2), a single flasher or a plurality of flashers may be used. Moreover, a portion of the volatile phase (2A) may be condensed in a condenser to form a condensate which is then recycled to the reaction step (reactor) (1). The whole quantity of the volatile phase (2A) may be fed to the distillation column of the first distillation step (3) without recycling of a portion of the volatile phase (2A) to the reactor (1).

If necessary, the catalyst component (metal catalyst component) may be separated from the less-volatile phase (2B) by a single step or a plurality of steps and may be returned to the reaction step (1) for recycle or reuse.

(3) First Distillation Step (Splitter Column or Distillation Column)

In the first distillation step (splitter column) (3), the volatile phase (2A) (the line 23) is separated into a first overhead (3A), a crude acetic acid stream or side-cut crude acetic acid stream (3B), and a bottom stream (3C); the first overhead (3A) (overhead gas, lower boiling point fraction) is withdrawn from a top or upper part of the column via a withdrawing line 31, the crude acetic acid stream (3B) is side-cut via a line 42 and mainly contains acetic acid, and the bottom stream (higher boiling point fraction) (3C) is withdrawn from a bottom or lower part of the column via a bottom line 45.

Incidentally, to the distillation column (splitter column) (3) are recycled: a portion 66 of a third overhead (6A) (a line 61) from a third distillation column (6), a portion 172 of an overhead stream 171 from the off-gas treatment section (15) (the high-pressure absorption column (16)), and a bottom acetic acid stream 184 from the off-gas treatment section (15) (the low-pressure absorption column (17)).

The first overhead (3A) contains methyl iodide, water, and methyl acetate and also contains acetaldehyde and carbon monoxide. The first overhead (3A) is fed to the separation section (9) for separating impurities such as acetaldehyde, and the off-gas treatment section (15).

The crude acetic acid stream (3B) (the line 42) mainly or primarily contains acetic acid, and also contains methyl iodide, methyl acetate, water, and others. A portion 43 of the crude acetic acid stream 42 may be returned to the first distillation column (splitter column) (3), the residual portion 44 of the crude acetic acid stream 42 is purified by a purification section (4) for removing, for example, water and a higher boiling point fraction, to product acetic acid with a high purity.

The bottom liquid stream (3C) (the line 45) usually contains at least water and acetic acid and also often contains propionic acid or others. A portion of the bottom liquid stream (3C) is returned to a bottom of the splitter column (3). The bottom liquid stream 45, which may contain an entrained metal catalyst component (lithium iodide), is recycled to the flasher or evaporator (2).

The first overhead (3A) contains at least one permanganate reducing compound (PRC) and methyl iodide. The PRC contains at least by-product acetaldehyde. The first overhead (3A) usually contains methyl acetate and may practically contain acetic acid, methanol, water, dimethyl ether, by-products derived from acetaldehyde (e.g., an aldehyde such as crotonaldehyde or butyraldehyde; a $C_{2-12}$alkyl iodide; an acetaldehyde derivative such as a $C_{3-12}$alkanecarboxylic acid; and a $C_{2-12}$alkane).

For example, the first overhead (3A) (the line 31) may have the following composition.

TABLE 14

| Average molecular weight 52.19 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.1 ppm to 1%) | 1 ppm to 0.1% | 10 ppm to 0.03% |
| CO | 500 ppm to 10% | 0.1 to 5% | 0.2 to 3% |
| $CO_2$ | 100 ppm to 2% | 500 ppm to 1% | 0.1% to 0.5% |
| $CH_4$ | 0 to 1% (e.g., 1 ppm to 1%) | 10 ppm to 0.5% | 100 ppm to 0.3% |
| $N_2$ | 0 to 1% (e.g., 1 ppm to 1%) | 10 ppm to 0.5% | 100 ppm to 0.3% |
| AD | 0.01 to 1% | 0.05 to 0.5% | 0.1 to 0.3% |
| MeOH | 0 to 4%, e.g., 0 to 2% (e.g., 10 ppm to 2%) | 100 ppm to 1% | 200 ppm to 0.7% (e.g., 0.1 to 0.5%) |
| MeI | 20 to 95% | 30 to 90% | 50 to 80% |
| MA | 1 to 40% | 3 to 30% | 7 to 20% |
| $H_2O$ | 1 to 60% | 5 to 50% | 10 to 30% |
| AcOH | 0.1 to 20% | 1 to 15% | 2 to 10% |
| HI | 0 to 1% (e.g., 0.1 ppm to 1%) | 1 ppm to 0.5% | 5 ppm to 0.3% (e.g., 10 ppm to 0.1%) |
| FrOH | 0 to 1% (e.g., 0.1 ppm to 1%) | 1 ppm to 0.5% | 10 ppm to 0.1% |
| PrOH | 0 to 0.5% (e.g., 0.1 ppm to 0.1%) | 1 to 700 ppm (e.g., 1 to 100 ppm) | 3 to 500 ppm (e.g., 3 to 50 ppm) |

TABLE 14-continued

| Average molecular weight 52.19 | Range | Preferred range | More preferred range |
|---|---|---|---|
| DME | 0 to 0.5% (e.g., 0.1 ppm to 0.1%) | 0.5 to 700 ppm (e.g., 1 to 300 ppm) | 5 to 500 ppm (e.g., 10 to 100 ppm) |
| $(CH_3)_2C{=}O$ | 0 to 0.5% (e.g., 0.1 ppm to 0.1%) | 1 to 100 ppm | 10 to 70 ppm |
| EtOH | 0 to 0.5% (e.g., 0.1 ppm to 0.1%) | 1 to 100 ppm | 10 to 70 ppm |
| EA | 0 to 0.5% (e.g., 0.1 ppm to 0.1%) | 1 to 100 ppm | 10 to 70 ppm |
| EtI | 0 to 0.5% (e.g., 0.1 ppm to 0.1%) | 1 to 100 ppm | 10 to 70 ppm |
| LiI | 0 to 0.1% (e.g., 0.1 ppt to 10 ppm) | 1 ppt to 1 ppm | 10 ppt to 0.1 ppm |
| Rh | 0 to 0.1% (e.g., 0.1 ppt to 10 ppm) | 1 ppt to 1 ppm | 10 ppt to 0.1 ppm |

For example, the crude acetic acid stream (3B) (the line 42) may have the following composition.

The composition of the crude acetic acid stream 44 to be fed to the purification section (purification step group or unit group) may be substantially the same as (or similar to) the composition of the crude acetic acid stream (3B) (the line 42).

TABLE 15

| Average molecular weight 58.72 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 1%) | 1 ppm to 0.1% | 10 ppm to 0.03% |
| CO | 0 to 1% (e.g., 10 ppm to 1%) | 50 ppm to 0.5% | 100 ppm to 0.3% |
| $CO_2$ | 0 to 1% (e.g., 0.1 ppm to 0.5%) | 1 ppm to 0.2% | 2 ppm to 0.1% |
| $CH_4$ | 0 to 1% (e.g., 1 ppm to 1%) | 10 ppm to 0.5% | 100 ppm to 0.3% |
| $N_2$ | 0 to 1% (e.g., 1 ppm to 1%) | 10 ppm to 0.5% | 100 ppm to 0.3% |
| AD | 0 to 1% (e.g., 5 ppm to 1%) | 10 ppm to 0.5% | 20 ppm to 0.3% |
| MeOH | 0 to 2% (e.g., 10 ppm to 1.5%) | 20 ppm to 1.2% (e.g., 100 ppm to 1%) | 30 ppm to 0.1% (or 0.1% to 0.5%) |
| MeI | 0.1 to 15% | 0.5 to 10% | 1 to 5% |
| MA | 0.1 to 15% | 0.5 to 10% | 1 to 5% |
| $H_2O$ | 0.1 to 10% | 0.5 to 8% | 1 to 5% |
| AcOH | 10 to 99% (e.g., 30 to 98%) | 50 to 97% | 60 to 95% |
| HI | 0 to 1% (e.g., 0.1 ppm to 1%) | 1 ppm to 0.5% | 10 ppm to 0.1% |
| FrOH | 0 to 1% (e.g., 0.1 ppm to 1%) | 1 ppm to 0.5% | 10 ppm to 0.1% |
| PrOH | 0 to 0.5% (e.g., 0.1 ppm to 0.1%) | 1 to 700 ppm (e.g., 1 to 100 ppm) | 3 to 500 ppm (e.g., 3 to 50 ppm) |
| DME | 0 to 0.5% (e.g., 0.1 ppm to 0.1%) | 0.5 to 700 ppm (e.g., 1 to 300 ppm) | 5 to 500 ppm (e.g., 10 to 100 ppm) |
| $(CH_3)_2C{=}O$ | 0 to 0.5% (e.g., 0.1 ppm to 0.1%) | 1 to 100 ppm | 10 to 70 ppm |
| EtOH | 0 to 0.5% (e.g., 0.1 ppm to 0.1%) | 1 to 100 ppm | 10 to 70 ppm |
| EA | 0 to 0.5% (e.g., 0.1 ppm to 0.1%) | 1 to 100 ppm | 10 to 70 ppm |
| EtI | 0 to 0.5% (e.g., 0.1 ppm to 0.1%) | 1 to 100 ppm | 10 to 70 ppm |
| Li | 0 to 0.1% (e.g., 100 ppt to 10 ppm) | 0.5 ppb to 50 ppm (e.g., 1 ppb to 1 ppm) | 5 ppb to 10 ppm (e.g., 10 ppb to 0.5 ppm) |
| Rh | 0 to 0.1% (e.g., 10 ppt to 10 ppm) | 0.1 ppb to 1 ppm | 1 to 100 ppb |
| Fe | 0 to 0.1% (e.g., 0.1 ppt to 100 ppm) | 1 ppt to 10 ppm | 10 ppt to 1 ppm |
| Ni | 0 to 0.1% (e.g., 0.1 ppt to 100 ppm) | 1 ppt to 10 ppm | 10 ppt to 1 ppm |
| Cr | 0 to 0.1% (e.g., 0.1 ppt to 100 ppm) | 1 ppt to 10 ppm | 10 ppt to 1 ppm |
| Mo | 0 to 0.1% (e.g., 0.1 ppt to 100 ppm) | 1 ppt to 10 ppm | 10 ppt to 1 ppm |
| Zn | 0 to 0.1% (e.g., 0.1 ppt to 100 ppm) | 1 ppt to 10 ppm | 10 ppt to 1 ppm |
| Cu | 0 to 0.1% (e.g., 0.1 ppt to 100 ppm) | 1 ppt to 10 ppm | 10 ppt to 1 ppm |

The ratio of the flow rate of the crude acetic acid stream (3B) to be fed to the purification section (4) relative to that to be recycled to the splitter column (3) [the former/the latter] may be about 100/1 to 2/1 (e.g., about 25/1 to 5/1) and preferably about 15/1 to 7/1 (e.g., about 10/1 to 8/1).

For example, the bottom liquid stream (3C) (the line 45) may have the following composition.

TABLE 16

| Average molecular weight 58.88 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 1%) | 1 ppm to 0.1% | 10 ppm to 0.01% |
| CO | 0 to 2% (e.g., 1 ppm to 2%) | 10 ppm to 1% | 100 ppm to 0.1% |
| $CO_2$ | 0 to 1% (e.g., 0.1 ppm to 1%) | 1 ppm to 0.1% | 10 ppm to 0.01% |
| $CH_4$ | 0 to 1% (e.g., 0.1 ppm to 1%) | 1 ppm to 0.1% | 10 ppm to 0.01% |
| $N_2$ | 0 to 1% (e.g., 0.1 ppm to 1%) | 1 ppm to 0.1% | 10 ppm to 0.01% |
| AD | 0 to 0.1% (e.g., 0.01 to 500 ppm) | 0.1 to 200 ppm | 1 to 100 ppm |
| MeOH | 0 to 1% (e.g., 0.1 ppm to 1%) | 1 ppm to 0.2% | 10 ppm to 0.1% |
| MeI | 5 ppm to 5% (e.g., 10 ppm to 2%) | 50 ppm to 3% (e.g., 100 ppm to 1%) | 200 ppm to 2% (e.g., 300 ppm to 0.5%) |
| MA | 0.01 to 6% | 0.1 to 4% | 0.5 to 3% |
| $H_2O$ | 0.01 to 10% | 0.1 to 5% | 0.5 to 4% (e.g., 1 to 3%) |
| AcOH | 60 to 99.5% (e.g., 80 to 99%) | 85 to 99% | 90 to 98% |
| HI | 0 to 1% (e.g., 0.01 ppm to 1%) | 0.1 ppm to 0.5% | 1 ppm to 0.1% |
| FrOH | 0 to 1% (e.g., 0.1 ppm to 0.1%) | 1 to 500 ppm | 5 to 100 ppm |
| PrOH | 0.1 ppm to 0.1% | 1 to 500 ppm | 3 to 300 ppm (e.g., 5 to 100 ppm) |
| DME | 0 to 1% (e.g., 0.1 ppm to 0.1%) | 1 to 500 ppm | 3 to 300 ppm (e.g., 5 to 100 ppm) |
| $(CH_3)_2C{=}O$ | 0 to 1% (e.g., 0.1 ppm to 0.1%) | 1 to 500 ppm | 5 to 100 ppm |
| EtOH | 0 to 1% (e.g., 0.1 ppm to 0.1%) | 1 to 500 ppm | 5 to 100 ppm |
| EA | 0 to 1% (e.g., 0.1 ppm to 0.1%) | 1 to 500 ppm | 5 to 100 ppm |
| EtI | 0 to 1% (e.g., 0.1 ppm to 0.1%) | 1 to 500 ppm | 5 to 100 ppm |
| LiI | 1 ppm to 2% (e.g., 1 ppm to 0.5%) | 3 ppm to 1.5% (e.g., 5 ppm to 0.1%) | 5 ppm to 1% (e.g., 10 to 500 ppm) |
| Rh | 1 ppb to 300 ppm | 10 ppb to 100 ppm | 100 ppb to 50 ppm |
| Fe | 0 to 1% (e.g., 0.1 ppm to 0.5%) | 1 ppm to 0.2% | 10 ppm to 0.1% |
| Ni | 0 to 0.5% (e.g., 0.1 ppm to 0.2%) | 1 ppm to 0.1% | 10 to 400 ppm |
| Cr | 0 to 0.5% (e.g., 0.1 ppm to 0.2%) | 1 ppm to 0.1% | 10 to 400 ppm |
| Mo | 0 to 0.5% (e.g., 0.01 ppm to 0.1%) | 0.1 to 400 ppm | 1 to 200 ppm |
| Zn | 0 to 1% (e.g., 0.1 ppm to 4000 ppm) | 1 ppm to 0.2% | 10 ppm to 0.1% |
| Cu | 0 to 0.1% (e.g., 0.001 to 200 ppm) | 0.01 to 100 ppm | 0.1 to 20 ppm |

As the distillation column (splitter column), there may be used a plate column, a packed column, or other columns. The liquid stream (3C) may be discharged. A portion or whole of the liquid stream (3C) may be returned to the splitter column (3) or may be recycled to the reaction step (the reactor) (1).

(4) Purification Section (Purification Step Group or Unit Group)

The crude acetic acid stream (3B) (a line 44) contains impurities such as a lower boiling point impurity, a higher boiling point impurity, and an ionic iodine compound. In order to separate and remove these impurities for purification, the crude acetic acid stream (3B) is fed to the purification section (purification step group or unit group) (4). For example, the purification section (4) may comprise the following steps (5), (6), (7), and (8): (5) a dehydration step (a dehydration distillation column) for mainly removing water from the crude acetic acid stream; (6) a higher boiling component (or fraction) removing step (a heavy end column or a higher boiling component (or fraction) distillation column) for removing a higher boiling component (or fraction) from the crude acetic acid stream; (7) a purification step (a purification distillation column) for further removing impurities from the crude acetic acid stream; and (8) an ion exchange step for separating an iodine compound from the crude acetic acid stream. The arrangement of the dehydration step (5), the higher boiling component removing step (6), the purification step (7), and the ion exchange step (8) is not limited to this order, and, for example, after the ion exchange step (8), the dehydration step (5), the higher boiling point (or heavy) component removing step (6), and the purification step (7) may be arranged in this order. After the dehydration step (5) and the higher boiling component removing step (6), the ion exchange step (8) and then the purification step (7) may be arranged in this order. After the dehydration step (5), the higher boiling component removing step (6), and the purification step (7), the ion exchange step (8) may be carried out. The purification section (4) usually comprises at least the dehydration step (5) among the steps (5) to (8). The purification step (7) is not necessarily needed.

(5) Dehydration Step (Dehydration Distillation Column)

In the dehydration step (5), the crude acetic acid stream (3B) (the line 44) is distilled in the second distillation column (dehydration distillation column) to form a second overhead (5A) rich in water and a bottom acetic acid stream (5B) rich in acetic acid; the second overhead (5A) is withdrawn from a top or upper part of the column via a withdrawing line 51, and the bottom acetic acid stream (5B) is withdrawn from a bottom or lower part of the column via a bottom line 56. A portion of the bottom acetic acid stream (5B) is heated by a heating unit and is then returned to the dehydration step (dehydration distillation column) (5), and the residual portion of the bottom acetic acid stream (5B) is fed to the third distillation column (heavy end column or higher boiling component distillation column) (6).

The second overhead (5A) is cooled in a condenser and is then introduced to a hold tank T2 to form a condensate 52 and a gaseous phase 55. A portion 53 of the condensate 52 is returned to the second distillation column (5) for reflux, and another portion of the condensate is mixed with the less-volatile phase (2B) via a line 54, and the mixture is recycled to the reactor (1). The gaseous phase (noncondensable gas (off-gas)) 55 from the hold tank T2, which is rich in carbon monoxide, is fed to the off-gas treatment section (15).

For example, the second overhead (5A) (the line 51) may have the following composition.

The composition of the condensates 52, 53 of the second overhead (5A) may be substantially the same as (or similar to) the composition of the second overhead (5A). The compositions of the condensates 52, 53 may have a component ratio (content of each component) obtained or calculated by subtracting the component ratio of the gaseous phase (noncondensable gas) 55 from the hold tank T2 from the component ratio of the second overhead (5A).

TABLE 17

| Average molecular weight 56.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.01 ppm to 0.1%) | 0.1 ppb to 500 ppm (e.g., 0.1 to 500 ppm) | 1 ppb to 100 ppm (e.g., 1 to 100 ppm) |
| CO | 0 to 1% (e.g., 0.1 ppm to 1%) | 0.1 ppb to 0.5% (e.g., 1 ppm to 0.5%) | 10 ppb to 0.1% (e.g., 10 ppm to 0.1%) |
| $CO_2$ | 0 to 1% (e.g., 0.01 ppm to 0.1%) | 0.1 ppb to 500 ppm (e.g., 0.1 to 500 ppm) | 1 ppb to 100 ppm (e.g., 1 to 100 ppm) |
| $CH_4$ | 0 to 1% (e.g., 0.01 ppm to 0.1%) | 0.1 ppb to 500 ppm (e.g., 0.1 to 500 ppm) | 1 ppb to 100 ppm (e.g., 1 to 100 ppm) |
| $N_2$ | 0 to 5%, 0 to 2%, 0 to 1% (e.g., 0.01 ppm to 0.1%) | 0.1 to 500 ppm | 1 to 100 ppm |
| AD | 0.1 ppm to 1%, e.g., 1 ppm to 0.3% | 1 ppm to 0.2%, e.g., 10 ppm to 0.1% | 1 ppm to 0.1%, e.g., 50 to 500 ppm |
| MeOH | 0 to 2% (e.g., 10 ppm to 2%) | 100 ppm to 1% | 200 ppm to 0.5%, e.g., 0.1 to 0.5% |
| MeI | 0.1 to 30% | 1 to 20% | 3 to 15% |
| MA | 0.1 to 20% | 1 to 15% | 2 to 12% |
| $H_2O$ | 0.1 to 20% | 1 to 15% | 2 to 10% |
| AcOH | 10 to 95% (e.g., 30 to 90%) | 50 to 85% | 60 to 85% |
| HI | 0 to 1% (e.g., 0.1 ppm to 1%), e.g., 0.1 ppb to 1% | 10 ppb to 0.5% (e.g., 1 ppm to 0.5%) | 0.1 ppm to 0.1% (e.g., 10 ppm to 0.1%) |
| FrOH | 0 to 1% (e.g., 0.1 ppm to 1%) | 1 ppm to 0.5% | 10 ppm to 0.1% |
| PrOH | 0 to 0.3% (e.g., 0.1 ppm to 0.1%) | 1 to 700 ppm (e.g., 1 to 100 ppm) | 3 to 500 ppm (e.g., 3 to 200 ppm), e.g., 3 to 50 ppm |
| DME | 0 to 1% (e.g., 0.1 ppm to 0.5%) | 1 ppm to 0.1% | 10 to 500 ppm |
| $(CH_3)_2C=O$ | 0 to 0.5% (e.g., 0.01 ppm to 0.1%) | 0.1 to 100 ppm | 1 to 50 ppm |
| EtOH | 0 to 0.5% (e.g., 0.01 ppm to 0.1%) | 0.1 to 100 ppm | 1 to 50 ppm |
| EA | 0 to 0.5% (e.g., 0.01 ppm to 0.1%) | 0.1 to 100 ppm | 1 to 50 ppm |
| EtI | 0 to 0.5% (e.g., 0.01 ppm to 0.1%) | 0.1 to 100 ppm | 1 to 50 ppm |
| Li | 0 to 0.1% (e.g., 0.1 ppt to 10 ppm) | 1 ppt to 1 ppm | 10 ppt to 0.1 ppm |
| Rh | 0 to 0.1% (e.g., 0.1 ppt to 10 ppm) | 1 ppt to 1 ppm | 10 ppt to 0.1 ppm |

The composition of the condensate 52 from the hold tank T2 may be substantially the same as (or similar to) the composition of the second overhead (5A) (the line 51).

For example, the gaseous phase (noncondensable gas) 55 from the hold tank T2 may have the following composition.

Incidentally, as described above, in a case where an inactive gas (such as nitrogen gas $N_2$) is introduced to regulate the pressure of the distillation column (5) and/or to prevent an organic matter from entering the measuring instrument, the composition of the inactive gas (such as nitrogen gas $N_2$) shown in the following Table 18 drastically increases.

TABLE 18

| Average molecular weight 27.90 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.01 ppm to 0.1%) | 0.1 to 500 ppm | 1 to 300 ppm |
| CO | 1 to 99.9% | 50 to 99.8% | 70 to 99.6% |
| $CO_2$ | 0 to 1% (e.g., 0.01 ppm to 0.5%) | 0.1 ppm to 0.1% | 1 to 500 ppm |
| $CH_4$ | 1 ppm to 10% | 10 ppm to 3% | 100 ppm to 1% |
| $N_2$ | 1 ppm to 10% | 10 ppm to 3% | 100 ppm to 1% |
| AD | 0 to 1% (e.g., 0.1 ppm to 0.5%) | 1 ppm to 0.1% | 10 to 500 ppm |
| MeOH | 0 to 1% (e.g., 0.1 ppm to 0.5%) | 1 ppm to 0.1% | 10 to 500 ppm |
| MeI | 0 to 1% (e.g., 1 ppm to 1%) | 5 ppm to 0.5% | 10 pm to 0.1% |
| MA | 0 to 1% (e.g., 1 ppm to 1%) | 5 ppm to 0.5% | 10 pm to 0.1% |
| $H_2O$ | 0 to 1% (e.g., 1 ppm to 1%) | 5 ppm to 0.5% | 10 pm to 0.1% |
| AcOH | 0 to 1% (e.g., 1 ppm to 1%) | 5 ppm to 0.5% | 10 pm to 0.1% |
| HI | 0 to 0.5% (e.g., 0.01 ppm to 0.1%) | 0.1 ppm to 0.05% | 1 ppm to 0.01% |
| FrOH | 0 to 0.5% (e.g., 0.01 ppm to 0.1%) | 0.1 ppm to 0.05% | 1 ppm to 0.01% |
| PrOH | 0 to 0.5% (e.g., 0.01 ppm to 0.1%) | 0.1 ppm to 0.05% | 1 ppm to 0.01% |
| DME | 0 to 0.5% (e.g., 0.01 ppm to 0.1%) | 0.1 ppm to 0.05% | 1 ppm to 0.01% |
| $(CH_3)_2C=O$ | 0 to 0.5% (e.g., 0.01 ppm to 0.1%) | 0.1 to 100 ppm | 1 to 50 ppm |
| EtOH | 0 to 0.5% (e.g., 0.01 ppm to 0.1%) | 0.1 to 100 ppm | 1 to 50 ppm |
| EA | 0 to 0.5% (e.g., 0.01 ppm to 0.1%) | 0.1 to 100 ppm | 1 to 50 ppm |
| EtI | 0 to 0.5% (e.g., 0.01 ppm to 0.1%) | 0.1 to 100 ppm | 1 to 50 ppm |
| Li | 0 to 0.1% (e.g., 0.1 ppt to 10 ppm) | 1 ppt to 1 ppm | 10 ppt to 0.1 ppm |
| Rh | 0 to 0.1% (e.g., 0.1 ppt to 10 ppm) | 1 ppt to 1 ppm | 10 ppt to 0.1 ppm |

For example, the bottom acetic acid stream (5B) (the line 56) may have the following composition.

TABLE 19

| Average molecular weight 59.99 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 0.1% (e.g., 0.01 to 100 ppm) | 0.1 to 50 ppm | 1 to 10 ppm |
| CO | 0 to 0.1% (e.g., 0.01 to 100 ppm) | 0.1 to 50 ppm | 1 to 10 ppm |
| $CO_2$ | 0 to 0.1% (e.g., 0.01 to 100 ppm) | 0.1 to 50 ppm | 1 to 10 ppm |
| $CH_4$ | 0 to 0.1% (e.g., 0.01 to 100 ppm) | 0.1 to 50 ppm | 1 to 10 ppm |
| $N_2$ | 0 to 0.1% (e.g., 0.01 to 100 ppm) | 0.1 to 50 ppm | 1 to 10 ppm |
| AD | 0 to 0.05% (e.g., 0.001 to 50 ppm) | 0.01 to 20 ppm | 0.1 to 10 ppm |
| MeOH | 0 to 0.1% (e.g., 0.001 to 100 ppm) | 0.01 to 10 ppm | 0.1 to 5 ppm |
| MeI | 0 to 0.01% (e.g., 0.01 to 10 ppb) | 0.05 to 200 ppb (e.g., 0.1 to 5 ppb) | 0.2 to 50 ppb (e.g., 0.2 to 10 ppb), e.g., 0.3 to 2 ppb |
| MA | 0 to 0.1% (e.g., 0.001 ppm to 0.1%) | 0.01 to 100 ppm | 0.1 to 50 ppm |
| $H_2O$ | 0 to 1% (e.g., 1 ppm to 1%) | 10 ppm to 0.5% | 100 ppm to 0.1% |
| AcOH | 98 to 100% | 99 to 99.999% | 99.5 to 99.99% |
| HI | 0 to 0.1% (e.g., 0.01 ppb to 100 ppm) | 0.1 ppb to 10 ppm | 1 ppb to 1 ppm |
| FrOH | 0 to 0.1% (e.g., 0.1 to 500 ppm) | 1 to 100 ppm | 5 to 50 ppm |
| PrOH | 0 to 0.2% (e.g., 5 ppm to 0.2%) | 30 ppm to 0.1% | 70 to 500 ppm (e.g., 100 to 250 ppm) |
| DME | 0 to 0.1% (e.g., 1 ppb to 10 ppm) | 10 ppb to 5 ppm | 50 ppb to 1 ppm |
| $(CH_3)_2C=O$ | 0 to 0.1% (e.g., 0.1 ppb to 100 ppm) | 1 ppb to 10 ppm | 10 ppb to 1 ppm |
| EtOH | 0 to 0.1% (e.g., 0.1 ppb to 100 ppm) | 1 ppb to 10 ppm | 10 ppb to 1 ppm |
| EA | 0 to 0.1% (e.g., 0.1 ppb to 100 ppm) | 1 ppb to 10 ppm | 10 ppb to 1 ppm |
| EtI | 0 to 0.1% (e.g., 0.1 ppb to 100 ppm) | 1 ppb to 10 ppm | 10 ppb to 1 ppm |

TABLE 19-continued

| Average molecular weight 59.99 | Range | Preferred range | More preferred range |
|---|---|---|---|
| Li | 0 to 0.1% (e.g., 1 ppt to 10 ppm) | 10 ppt to 1 ppm | 100 ppt to 0.1 ppm |
| Rh | 0 to 0.1% (e.g., 1 ppt to 10 ppm) | 10 ppt to 1 ppm | 100 ppt to 0.1 ppm |

In the second distillation step (5), in order to convert hydrogen iodide in the crude acetic acid stream 44 into methyl iodide which is distilled out as the second overhead (5A) (the line 51), methanol 3 may be added to one or a plurality of sites of the second distillation column (dehydration distillation column) (5). Further, the bottom acetic acid stream 56 from the second distillation step (5) may be mixed with a potassium hydroxide aqueous solution 57 to allow hydrogen iodide to react with potassium hydroxide for removing hydrogen iodide as potassium iodide. The bottom acetic acid stream 58 which has been treated with potassium hydroxide may be distilled in the third distillation step (6) for mainly separating and removing a higher boiling component (or fraction).

In order to remove hydrogen iodide, a methanol source, for example, at least one component selected from the group consisting of methanol, methyl acetate, and dimethyl ether, may be added to the distillation column. Potassium hydroxide is used in the above embodiment. However, other alkali metal components may also be used. The alkali metal components may include, for example, an alkali metal hydroxide (e.g., sodium hydroxide), an alkali metal carbonate, and an alkali metal acetate (such as sodium acetate or potassium acetate).

The composition of the methanol 3 is substantially the same as described above.

For example, the potassium hydroxide aqueous solution 57 may have the following composition.

TABLE 20

| Average molecular weight 25.94 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2O$ | 40 to 99.9% | 50 to 99% | 55 to 90% |
| KOH | 0.1 to 60% | 1 to 50% | 10 to 45% |

For example, the bottom acetic acid stream 58 may have the following composition.

TABLE 21

| Average molecular weight 59.98 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 0.1% (e.g., 0.01 to 100 ppm) | 0.1 to 50 ppm | 1 to 10 ppm |
| CO | 0 to 0.1% (e.g., 0.01 to 100 ppm) | 0.1 to 50 ppm | 1 to 10 ppm |
| $CO_2$ | 0 to 0.1% (e.g., 0.01 to 100 ppm) | 0.1 to 50 ppm | 1 to 10 ppm |
| $CH_4$ | 0 to 0.1% (e.g., 0.01 to 100 ppm) | 0.1 to 50 ppm | 1 to 10 ppm |
| $N_2$ | 0 to 0.1% (e.g., 0.01 to 100 ppm) | 0.1 to 50 ppm | 1 to 10 ppm |
| AD | 0 to 0.1% (e.g., 0.001 to 50 ppm) | 0.01 to 20 ppm | 0.1 to 10 ppm |
| MeOH | 0 to 0.1% (e.g., 0.001 to 100 ppm) | 0.01 to 10 ppm | 0.1 to 5 ppm |
| MeI | 0 to 0.01% (e.g., 0.01 to 10 ppb) | 0.1 to 5 ppb | 0.3 to 2 ppb |
| MA | 0 to 0.1% (e.g., 0.001 ppm to 0.1%) | 0.01 to 100 ppm | 0.1 to 50 ppm |
| $H_2O$ | 0 to 1% (e.g., 1 ppm to 1%) | 10 ppm to 0.5% | 100 ppm to 0.1% |
| AcOH | 98 to 99.999% | 99 to 99.99% | 99.5 to 99.9% |
| HI | 0 to 0.1% (e.g., 0.01 ppb to 100 ppm) | 0.1 ppb to 10 ppm | 1 ppb to 1 ppm |
| FrOH | 0 to 0.1% (e.g., 0.1 to 500 ppm) | 1 to 100 ppm | 5 to 50 ppm |
| PrOH | 0 to 0.2% (e.g., 5 ppm to 0.2%) | 30 ppm to 0.1% (e.g., 70 to 500 ppm) | 100 to 250 ppm |
| KOH | 0 to 0.1% (e.g., 1 ppm to 0.1%) | 5 to 500 ppm | 10 to 100 ppm |
| DME | 0 to 0.1% (e.g., 1 ppb to 10 ppm) | 10 ppb to 5 ppm | 50 ppb to 1 ppm |
| $(CH_3)_2C{=}O$ | 0 to 0.1% (e.g., 0.01 to 10 ppm) | 0.1 ppb to 1 ppm | 1 ppb to 0.1 ppm |
| EtOH | 0 to 0.1% (e.g., 0.01 to 10 ppm) | 0.1 ppb to 1 ppm | 1 ppb to 0.1 ppm |
| EA | 0 to 0.1% (e.g., 0.01 to 10 ppm) | 0.1 ppb to 1 ppm | 1 ppb to 0.1 ppm |
| EtI | 0 to 0.1% (e.g., 0.01 to 10 ppm) | 0.1 ppb to 1 ppm | 1 ppb to 0.1 ppm |

TABLE 21-continued

| Average molecular weight 59.98 | Range | Preferred range | More preferred range |
|---|---|---|---|
| Li | 0 to 0.1% (e.g., 1 ppt to 10 ppm) | 10 ppt to 1 ppm | 100 ppt to 0.1 ppm |
| Rh | 0 to 0.1% (e.g., 1 ppt to 10 ppm) | 10 ppt to 1 ppm | 100 ppt to 0.1 ppm |

The dehydration step (dehydration distillation column) (5) may comprise a single step (a distillation column) or may comprise a plurality of steps (distillation columns) for distilling the bottom stream (5B) by one or a plurality of succeeding step(s) (distillation column(s)). For example, a portion of the bottom stream (5B) may be returned to the dehydration step (dehydration distillation column) (5), while the residual portion of the bottom stream (5B) may be fed to the succeeding dehydration step (dehydration distillation column) (5). As the distillation column(s) of the second distillation step (5), there may be used a plate column, a packed column, or other columns.

(6) Higher Boiling Component Removing Step (Heavy End Column)

The bottom acetic acid stream (5B) still contains a higher boiling component such as propionic acid, although the bottom acetic acid stream, from which a lower boiling component (or fraction) has been removed, has a significantly improved acetic acid purity. Thus, the bottom acetic acid stream (a line 56 or a line 58) is subjected to the third distillation step (heavy end column) (6) for removing the higher boiling component. Specifically, in the third distillation step (heavy end column) (6), the bottom acetic acid stream (5B) is distilled to form a third overhead (6A) (a line 61) rich in acetic acid, an acetic acid stream (6B) (a line 67) rich in acetic acid, and a bottom stream (6C) (a line 68) rich in a higher boiling component (or fraction) containing acetic acid; the third overhead (6A) is withdrawn from a top or upper part of the column, the acetic acid stream (6B) is side-cut at a portion upper than a middle portion of the column, and the bottom stream (6C) is withdrawn from a bottom or lower part of the column.

The side-cut acetic acid stream (6B) (the line 67) is further purified in a fourth distillation step (purification column) (7) for removal of impurities. A side-cut acetic acid stream (7B) from the fourth distillation step (purification column) (7) id fed to the ion exchange step (8). A portion of the side-cut acetic acid stream (7B) (a line 75) is mixed with the bottom stream (5B) of the second distillation step (dehydration distillation column) (5) via a line 76.

The third overhead (6A) is cooled and condensed in a condenser to forma condensate 62 which is then held in a hold tank T3. A first portion of the condensate 62 is returned for reflux to an upper part of the higher boiling point removing step (heavy end column) (6) via a reflux line 63. A second portion of the condensate 62 is recycled to the distillation column (dehydration distillation column) (5) via a line 64. A third portion of the condensate 62 is fed to a diffusion step (diffusion column) (18) of the off-gas treatment section (15) via a line 65 and the flash evaporator (2) via a line 66. A noncondensable gas from the hold tank T3 may be fed to the reactor (1) or the evaporator (2).

A portion of the bottom stream (6C) (the line 68) containing acetic acid is returned to the third distillation step (heavy end column) (6), and the residual portion of the bottom stream (6C) (the line 68) is fed to an incineration unit (not shown) via a line 69.

For example, the third overhead (6A) may have the following composition.

The compositions of the reflux liquid (lines 62, 63) and the condensate (line 64, line 65) may have a composition ratio (content of each component) obtained or calculated by subtracting a component ratio of a noncondensable gas in the condenser and a noncondensable gas in the hold tank T3 from the component ratio of the third overhead (6A).

TABLE 22

| Average molecular weight 59.58 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.001 ppm to 0.1%) | 0.01 to 100 ppm | 0.1 to 10 ppm |
| CO | 0 to 1% (e.g., 0.01 ppm to 1%) | 0.1 ppm to 0.1% | 10 ppm to 0.01% |
| $CO_2$ | 0 to 1% (e.g., 0.001 ppm to 0.1%) | 0.01 to 100 ppm | 0.1 to 10 ppm |
| $CH_4$ | 0 to 1% (e.g., 0.001 ppm to 0.1%) | 0.01 to 100 ppm | 0.1 to 10 ppm |
| $N_2$ | 0 to 1% (e.g., 0.001 ppm to 0.1%) | 0.01 to 100 ppm | 0.1 to 10 ppm |
| AD | 0 to 1% (e.g., 0.01 ppm to 0.1%) | 0.1 to 100 ppm | 0.2 to 50 ppm, 0.5 to 50 ppm |
| MeOH | 0 to 1% (e.g., 0.01 ppm to 0.1%) | 0.1 to 100 ppm | 0.5 to 50 ppm |
| MeI | 0 to 1% (e.g., 0.01 ppm to 0.1%) | 0.001 to 300 ppm (e.g., 0.1 to 100 ppm) | 0.003 to 50 ppm (e.g., 0.5 to 10 ppm) |
| MA | 0 to 1% (e.g., 1 ppm to 1%) | 0.1 ppm to 0.5% (e.g., 10 ppb to 0.1%) | 1 to 750 ppm (e.g., 50 to 500 ppm) |
| $H_2O$ | 10 ppm to 2% | 100 ppm to 1% | 0.1% to 0.5% |
| AcOH | 90 to 99.99% | 98 to 99.9% | 99 to 99.8% |
| HI | 0 to 1% (e.g., 0.1 ppb to 0.1%) | 1 ppb to 100 ppm | 2 ppb to 10 ppm (e.g., 10 ppb to 10 ppm) |
| FrOH | 0 to 1% (e.g., 0.1 ppb to 0.5%) | 1 ppm to 0.1% | 10 to 500 ppm |

TABLE 22-continued

| Average molecular weight 59.58 | Range | Preferred range | More preferred range |
|---|---|---|---|
| PrOH | 0 to 1% (e.g., 0.01 ppm to 0.1%) | 0.1 to 200 ppm | 1 to 50 ppm |
| DME | 0 to 1% (e.g., 0.01 ppm to 0.1%) | 0.1 to 200 ppm | 1 to 50 ppm |
| $(CH_3)_2C=O$ | 0 to 1% (e.g., 0.01 ppb to 10 ppm) | 0.1 ppb to 1 ppm | 1 ppb to 0.1 ppm |
| EtOH | 0 to 1% (e.g., 0.01 ppb to 10 ppm) | 0.1 ppb to 1 ppm | 1 ppb to 0.1 ppm |
| EA | 0 to 1% (e.g., 0.01 ppb to 10 ppm) | 0.1 ppb to 1 ppm | 1 ppb to 0.1 ppm |
| EtI | 0 to 1% (e.g., 0.01 ppb to 10 ppm) | 0.1 ppb to 1 ppm | 1 ppb to 0.1 ppm |
| Li | 0 to 0.1% (e.g., 0.01 ppt to 1 ppm) | 0.1 ppt to 0.1 ppm | 1 ppt to 0.01 ppm |
| Rh | 0 to 0.1% (e.g., 0.01 ppt to 1 ppm) | 0.1 ppt to 0.1 ppm | 1 ppt to 0.01 ppm |

For example, the side-cut acetic acid stream (6B) (the line 67) may have the following composition.

TABLE 23

| Average molecular weight 60.01 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.001 ppm to 0.1%) | 0.01 to 100 ppm | 0.1 to 10 ppm |
| CO | 0 to 1% (e.g., 0.01 ppm to 1%) | 0.1 ppm to 0.1% | 10 ppm to 0.01% |
| $CO_2$ | 0 to 1% (e.g., 0.001 ppm to 0.1%) | 0.01 to 100 ppm | 0.1 to 10 ppm |
| $CH_4$ | 0 to 1% (e.g., 0.001 ppm to 0.1%) | 0.01 to 100 ppm | 0.1 to 10 ppm |
| $N_2$ | 0 to 1% (e.g., 0.001 ppm to 0.1%) | 0.01 to 100 ppm | 0.1 to 10 ppm |
| AD | 0 to 1% (e.g., 0.001 ppm to 0.1%) | 0.01 to 100 ppm | 0.1 to 10 ppm |
| MeOH | 0 to 1% (e.g., 0.1 ppb to 100 ppm) | 1 ppb to 10 ppm | 10 ppb to 1 ppm |
| MeI | 0 to 1% (e.g., 0.01 ppb to 20 ppb) | 0.1 ppb to 10 ppm | 0.5 to 5 ppb |
| MA | 0 to 1% (e.g., 0.001 ppm to 0.1%) | 0.01 to 100 ppm | 0.1 to 10 ppm |
| $H_2O$ | 0 to 1% (e.g., 1 ppm to 0.5%) | 10 ppm to 0.2% | 50 ppm to 0.1% |
| AcOH | 99 to 100% | 99.8 to 99.999% | 99.9 to 99.99% |
| HI | 0 to 1% (e.g., 0.01 to 100 ppb) | 0.1 to 10 ppb | 0.5 to 5 ppb |
| FrOH | 0 to 1% (e.g., 0.1 to 500 ppm) | 1 to 100 ppm | 5 to 50 ppm |
| PrOH | 0 to 1% (e.g., 0.1 ppm to 0.1%) | 1 to 500 ppm | 10 to 250 ppm |
| DME | 50 ppm or less (1 ppt to 50 ppm) | 1 ppb to 10 ppm | 10 ppb to 1 ppm |
| $(CH_3)_2C=O$ | 0 to 1% (e.g., 0.01 ppb to 10 ppm) | 0.1 ppb to 1 ppm | 1 ppb to 0.1 ppm |
| EtOH | 0 to 1% (e.g., 0.01 ppb to 10 ppm) | 0.1 ppb to 1 ppm | 1 ppb to 0.1 ppm |
| EA | 0 to 1% (e.g., 0.01 ppb to 10 ppm) | 0.1 ppb to 1 ppm | 1 ppb to 0.1 ppm |
| EtI | 0 to 1% (e.g., 0.01 ppb to 10 ppm) | 0.1 ppb to 1 ppm | 1 ppb to 0.1 ppm |
| Li | 0 to 0.1% (e.g., 1 ppt to 1 ppm) | 10 ppt to 0.1 ppm | 100 ppt to 0.01 ppm |
| Rh | 0 to 0.1% (e.g., 1 ppt to 1 ppm) | 10 ppt to 0.1 ppm | 50 ppt to 0.01 ppm |

For example, the bottom stream (6C) (the line 68) may have the following composition.

TABLE 24

| Average molecular weight 59.70 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 100 ppm) | 10 ppt to 10 ppm | 1 ppb to 1 ppm |
| CO | 0 to 1% (e.g., 1 ppt to 0.1%) | 10 ppt to 100 ppm | 1 ppb to 10 ppm |
| $CO_2$ | 0 to 1% (e.g., 1 ppt to 100 ppm) | 10 ppt to 10 ppm | 1 ppb to 1 ppm |
| $CH_4$ | 0 to 1% (e.g., 1 ppt to 100 ppm) | 10 ppt to 10 ppm | 1 ppb to 1 ppm |
| $N_2$ | 0 to 1% (e.g., 1 ppt to 100 ppm) | 10 ppt to 10 ppm | 1 ppb to 1 ppm |
| AD | 0 to 1% (e.g., 1 ppt to 100 ppm) | 10 ppt to 10 ppm | 1 ppb to 1 ppm |
| MeOH | 0 to 1% (e.g., 1 ppt to 100 ppm) | 10 ppt to 10 ppm | 1 ppb to 1 ppm |
| MeI | 0 to 1% (e.g., 1 ppt to 10 ppm) | 10 ppt to 10 ppm | 0.1 ppb to 1 ppm |
| MA | 0 to 1% (e.g., 1 ppt to 100 ppm) | 0.01 to 10 ppm | 0.1 ppm to 1 ppm |
| $H_2O$ | 0 to 1% (e.g., 1 ppm to 0.5%) | 5 ppm to 0.1% | 20 ppm to 0.02% |
| AcOH | 80 to 99% | 85 to 98% | 90 to 95% |
| HI | 0 to 1% (e.g., 0.01 ppb to 100 ppm) | 0.1 ppb to 10 ppm | 0.5 ppb to 1 ppm |
| FrOH | 0 to 1% (e.g., 0.1 ppb to 0.5%) | 1 ppb to 0.1% | 10 ppb to 500 ppm |

TABLE 24-continued

| Average molecular weight 59.70 | Range | Preferred range | More preferred range |
|---|---|---|---|
| PrOH | 0 to 1% (e.g., 10 ppm to 10%) | 50 ppm to 1% | 100 ppm to 0.1% |
| DME | 1 ppm or less (1 ppt to 1 ppm) | 1 ppb to 10 ppm | 10 ppb to 1 ppm |
| $(CH_3)_2C{=}O$ | 0 to 1% (e.g., 0.01 ppb to 10 ppm) | 0.1 ppb to 1 ppm | 1 ppb to 0.1 ppm |
| KOH | 0.01 to 40% | 0.1 to 20% | 1 to 15%, e.g., 3 to 10% |
| EtOH | 0 to 1% (e.g., 0.01 ppb to 10 ppm) | 0.1 ppb to 1 ppm | 1 ppb to 0.1 ppm |
| EA | 0 to 1% (e.g., 0.01 ppb to 10 ppm) | 0.1 ppb to 1 ppm | 1 ppb to 0.1 ppm |
| EtI | 0 to 1% (e.g., 0.01 ppb to 10 ppm) | 0.1 ppb to 1 ppm | 1 ppb to 0.1 ppm |
| Li | 0 to 0.1% (e.g., 1 ppb to 100 ppm) | 10 ppb to 10 ppm | 100 ppb to 5 ppm |
| Rh | 0 to 0.1% (e.g., 0.1 ppb to 50 ppm) | 1 ppb to 2 ppm | 10 ppb to 1 ppm |
| Fe | 0 to 0.1% (e.g., 100 ppt to 100 ppm) | 1000 ppt to 50 ppm | 1000 ppt to 10 ppm |
| Ni | 0 to 0.1% (e.g., 10 ppt to 10 ppm) | 100 ppt to 1 ppm | 1000 ppt to 0.5 ppm |
| Cr | 0 to 0.1% (e.g., 10 ppt to 10 ppm) | 100 ppt to 1 ppm | 1000 ppt to 0.5 ppm |
| Mo | 0 to 0.1% (e.g., 10 ppt to 10 ppm) | 100 ppt to 1 ppm | 1000 ppt to 0.5 ppm |
| Zn | 0 to 0.1% (e.g., 10 ppt to 10 ppm) | 100 ppt to 1 ppm | 1000 ppt to 0.5 ppm |
| Cu | 0 to 0.1% (e.g., 10 ppt to 10 ppm) | 100 ppt to 1 ppm | 1000 ppt to 0.5 ppm |

The higher boiling component removing step (heavy end column) (6) may also comprise a single step (a distillation column) or a plurality of steps (distillation columns). For example, a portion of the bottom stream (6C) may be returned to the higher boiling component removing step (heavy end column) (6), while the residual portion of the bottom stream (6C) may be fed to the succeeding higher boiling component removing step (heavy end column) (6). The bottom stream(s) (6C) from one or a plurality of higher boiling component removing steps (heavy end columns) (in particular, the last higher boiling component removing step) may be discharged as a waste fluid. As the distillation column(s) of the third distillation step (6), there may be used a plate column, a packed column, or other columns.

(7) Purification step

In the purification step (purification distillation column) (7), the acetic acid stream (6B) (the line 67) from the higher boiling component removing step (third distillation column) (6) is distilled to form a fourth overhead (7A) rich in a lower boiling component (or fraction), a purified acetic acid (7B), and a bottom stream (7C) containing a higher boiling component (or fraction); the fourth overhead (7A) is withdrawn from a top or upper part of the column via a withdrawing line 71, the purified acetic acid (7B) is side-cut via a withdrawing line 75, and the bottom stream (7C) is withdrawn from a bottom or lower part of the column via a bottom line 77.

The fourth overhead (7A) is cooled and condensed in a condenser on the line 71 to form a condensate and a noncondensable gas. A portion of the condensate from the condenser is returned to the purification step (purification distillation column) (7) via a line 72 for reflux, and the residual portion of the condensate is fed to an incineration unit (not shown) via a line 73. The noncondensable gas (off-gas) is fed to an incineration unit (not shown) via a line 74. The noncondensable gas (off-gas) may be recycled to the reaction system.

A first portion of the bottom stream (7C) is steam-heated by a reboiler (heat exchanger) on a line 80 by a portion of the third overhead (6A) (the line 61) from the higher boiling component removing step (third distillation column) (6) and is recycled to the purification step (purification distillation column) (7). Specifically, the heat energy of the portion of the third overhead (6A) is supplied to the first portion of the bottom stream (7C) as a heat source in the purification step (purification distillation column) (7).

A second portion of the bottom stream (7C) is heated by a reboiler (heater) on a line 78, and the resulting vapor is recycled to the purification step (purification distillation column) (7).

The portion of the third overhead (6A) cooled by the reboiler (heat exchanger) on the line 80 is held in a hold tank T4 and is then mixed with the residual portion of the bottom stream (7C), and the mixture is also recycled to the higher boiling component removing step (higher boiling component distillation column) (6) via a line 79 to remove a higher boiling component.

The side-cut purified acetic acid (7B) (the line 75) is cooled in a condenser or cooler and is then fed to the ion exchange step (8) via a line 81, and the treated purified acetic acid may be held in a product tank T5.

For example, the fourth overhead (7A) (the line 71) may have the following composition.

TABLE 25

| | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.001 ppm to 0.1%) | 0.01 to 100 ppm | 0.1 to 10 ppm |
| CO | 0 to 1% (e.g., 0.01 ppm to 1%) | 0.1 ppm to 0.1% | 10 ppm to 0.01% |
| $CO_2$ | 0 to 1% (e.g., 0.001 ppm to 0.1%) | 0.01 to 100 ppm | 0.1 to 10 ppm |
| $CH_4$ | 0 to 1% (e.g., 0.001 ppm to 0.1%) | 0.01 to 100 ppm | 0.1 to 10 ppm |
| $N_2$ | 0 to 1% (e.g., 0.001 ppm to 0.1%) | 0.01 to 100 ppm | 0.1 to 10 ppm |
| AD | 0 to 1% (e.g., 0.01 ppm to 0.1%) | 0.1 to 100 ppm | 0.5 to 50 ppm |
| MeOH | 0 to 1% (e.g., 0.01 ppm to 0.1%) | 0.1 to 100 ppm | 0.5 to 50 ppm |

TABLE 25-continued

| | Range | Preferred range | More preferred range |
|---|---|---|---|
| MeI | 0 to 1% (e.g., 1 ppb to 0.1%) | 0.01 to 100 ppm | 0.1 to 10 ppm |
| MA | 0 to 5% (e.g., 1 ppm to 3%) | 10 ppm to 2% | 100 ppm to 1% |
| $H_2O$ | 0.1 to 50% | 1 to 30% | 10 to 30% |
| AcOH | 50 to 99% | 60 to 95% | 70 to 90% |
| HI | 0 to 1% (e.g., 0.01 ppb to 0.1%) | 0.1 ppb to 100 ppm | 1 ppb to 10 ppm |
| FrOH | 0 to 1% (e.g., 10 ppm to 3%) | 100 ppm to 2% | 0.1% to 1% |
| PrOH | 0 to 1% (e.g., 0.01 ppm to 0.1%) | 0.1 to 200 ppm | 1 to 50 ppm |
| DME | 0 to 1% (e.g., 1 ppb to 0.1%) | 10 ppb to 200 ppm | 100 ppb to 50 ppm |
| $(CH_3)_2C{=}O$ | 0 to 1% (e.g., 0.01 ppb to 10 ppm) | 0.1 ppb to 1 ppm | 1 ppb to 0.1 ppm |
| EtOH | 0 to 1% (e.g., 0.01 ppb to 10 ppm) | 0.1 ppb to 1 ppm | 1 ppb to 0.1 ppm |
| EA | 0 to 1% (e.g., 0.01 ppb to 10 ppm) | 0.1 ppb to 1 ppm | 1 ppb to 0.1 ppm |
| EtI | 0 to 1% (e.g., 0.01 ppb to 10 ppm) | 0.1 ppb to 1 ppm | 1 ppb to 0.1 ppm |
| Li | 0 to 0.1% (e.g., 0.01 ppt to 0.1 ppm) | 0.1 ppt to 0.01 ppm | 1 ppt to 0.001 ppm |
| Rh | 0 to 0.1% (e.g., 0.01 ppt to 0.1 ppm) | 0.1 ppt to 0.01 ppm | 1 ppt to 0.001 ppm |

For example, the composition of the condensates 72, 73 may be substantially the same as (or similar to) the composition of the fourth overhead (7A) (the line 71). The compositions of the condensates 72, 73 may have a component ratio (content of each component) obtained or calculated by subtracting the component ratio of an off-gas 74 from the component ratio of the fourth overhead (7A) (the line 71).

For example, the off-gas 74 may have the following composition.

Incidentally, as described above, in a case where the inactive gas (such as nitrogen gas or carbon monoxide gas) purge is performed to regulate the pressure of the distillation column (7) and/or to protect the measuring instrument, the nitrogen or other concentrations as shown in the following Table 26 drastically increases according to the amount of the inactive gas introduced.

TABLE 26

| | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 1 ppb to 1%) | 0.01 ppm to 0.5% | 0.1 to 500 ppm |
| CO | 0 to 1% (e.g., 1 ppm to 99.9%) | 10 ppm to 99% | 100 ppm to 98% |
| $CO_2$ | 0 to 1% (e.g., 1 ppb to 1%) | 0.01 ppm to 0.5% | 0.1 to 500 ppm |
| $CH_4$ | 0 to 1% (e.g., 1 ppb to 1%) | 0.01 ppm to 0.5% | 0.1 to 500 ppm |
| $N_2$ | 0 to 1% (e.g., 1 ppm to 80%) | 10 ppm to 75% | 100 ppm to 70% |
| AD | 0 to 1% (e.g., 0.1 ppm to 0.5%) | 1 ppm to 0.1% | 10 to 500 ppm |
| MeOH | 0 to 1% (e.g., 0.1 ppm to 0.5%) | 1 ppm to 0.1% | 10 to 500 ppm |
| MeI | 1 ppm to 5% | 10 ppm to 3% | 100 ppm to 1% |
| MA | 1 ppm to 20% | 10 ppm to 5% | 100 ppm to 1% |
| $H_2O$ | 10 ppm to 30% | 100 ppm to 20% | 0.1 to 10% |
| AcOH | 10 ppm to 30% | 100 ppm to 20% | 0.1 to 10% |
| HI | 0 to 1% (e.g., 1 ppb to 0.1%) | 10 ppb to 0.01% | 100 ppb to 0.001% |
| FrOH | 0 to 1% (e.g., 0.1 ppm to 1%) | 1 ppm to 0.5% | 10 ppm to 0.1% |
| PrOH | 0 to 1% (e.g., 0.01 ppm to 0.1%) | 0.1 ppm to 0.05% | 1 ppm to 0.01% |
| DME | 0 to 1% (e.g., 0.01 ppm to 0.1%) | 0.1 ppm to 0.05% | 1 ppm to 0.01% |
| $(CH_3)_2C{=}O$ | 0 to 1% (e.g., 0.01 ppb to 10 ppm) | 0.1 ppb to 1 ppm | 1 ppb to 0.1 ppm |
| EtOH | 0 to 1% (e.g., 0.01 ppb to 10 ppm) | 0.1 ppb to 1 ppm | 1 ppb to 0.1 ppm |
| EA | 0 to 1% (e.g., 0.01 ppb to 10 ppm) | 0.1 ppb to 1 ppm | 1 ppb to 0.1 ppm |
| EtI | 0 to 1% (e.g., 0.01 ppb to 10 ppm) | 0.1 ppb to 1 ppm | 1 ppb to 0.1 ppm |
| Li | 0 to 0.1% (e.g., 0.01 ppt to 0.1 ppm) | 0.1 ppt to 0.01 ppm | 1 ppt to 0.001 ppm |
| Rh | 0 to 0.1% (e.g., 0.01 ppt to 0.1 ppm) | 0.1 ppt to 0.01 ppm | 1 ppt to 0.001 ppm |

For example, the side-cut purified acetic acid (7B) (the line 75) may have the following composition.

TABLE 27

| | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.001 ppm to 0.1%) | 0.01 to 100 ppm | 0.1 to 10 ppm |
| CO | 0 to 1% (e.g., 0.01 ppm to 1%) | 0.1 ppm to 0.1% | 1 to 100 ppm |
| $CO_2$ | 0 to 1% (e.g., 0.001 ppm to 0.1%) | 0.01 to 100 ppm | 0.1 to 10 ppm |

TABLE 27-continued

| | Range | Preferred range | More preferred range |
|---|---|---|---|
| $CH_4$ | 0 to 1% (e.g., 0.001 ppm to 0.1%) | 0.01 to 100 ppm | 0.1 to 10 ppm |
| $N_2$ | 0 to 1% (e.g., 0.001 ppm to 0.1%) | 0.01 to 100 ppm | 0.1 to 10 ppm |
| AD | 0 to 1% (e.g., 0.001 to 100 ppm) | 0.01 to 50 ppm | 0.1 to 10 ppm |
| MeOH | 0 to 1% (e.g., 0.1 ppb to 100 ppm) | 1 ppb to 10 ppm | 10 ppb to 1 ppm |
| MeI | 0 to 0.1% (e.g., 1 ppt to 20 ppb) | 10 ppt to 10 ppb | 100 ppt to 5 ppb |
| MA | 0 to 1% (e.g., 1 ppb to 100 ppm) | 5 ppb to 50 ppm (e.g., 10 ppb to 10 ppm) | 50 ppb to 25 ppm (e.g., 100 ppb to 5 ppm) |
| $H_2O$ | 0 to 1% (e.g., 1 ppm to 0.5%) | 10 ppm to 0.2% | 50 ppm to 0.1% |
| AcOH | 99.8 to 100% | 99.9 to 99.999% | 99.95 to 99.99% |
| HI | 0 to 0.1% (e.g., 1 ppt to 20 ppb) | 10 ppt to 10 ppb | 100 ppt to 5 ppb |
| TOI | 0 to 1% (e.g., 0.1 ppb to 0.1%) | 1 ppb to 100 ppm | 10 ppb to 10 ppm |
| HexI | 0 to 0.1% (e.g., 1 ppt to 20 ppb) | 10 ppt to 10 ppb | 100 ppt to 5 ppb |
| FrOH | 0 to 1% (e.g., 0.1 to 500 ppm) | 1 to 100 ppm | 5 to 50 ppm |
| PrOH | 0 to 1% (e.g., 0.1 ppm to 0.1%) | 1 to 500 ppm | 10 to 250 ppm |
| DME | 0 to 1% (e.g., 1 ppt to 50 ppm) | 1 ppb to 10 ppm | 10 ppb to 1 ppm |
| AcA | 0 to 1% (e.g., 0.1 ppb to 0.1%) | 1 ppb to 100 ppm | 10 ppb to 10 ppm |
| $(CH_3)_2C{=}O$ | 0 to 1% (e.g., 0.01 ppb to 10 ppm) | 0.1 ppb to 1 ppm | 1 ppb to 0.1 ppm |
| EtOH | 0 to 1% (e.g., 0.01 ppb to 10 ppm) | 0.1 ppb to 1 ppm | 1 ppb to 0.1 ppm |
| EA | 0 to 1% (e.g., 0.01 ppb to 10 ppm) | 0.1 ppb to 1 ppm | 1 ppb to 0.1 ppm |
| EtI | 0 to 1% (e.g., 0.01 ppb to 10 ppm) | 0.1 ppb to 1 ppm | 1 ppb to 0.1 ppm |
| Li | 0 to 0.1% (e.g., 0.01 to 100 ppb) | 0.1 to 10 ppb | 0.5 to 5 ppb |
| Rh | 0 to 0.1% (e.g., 1 ppt to 50 ppb) | 10 ppt to 10 ppb | 50 ppt to 3 ppb |

Incidentally, cooling of the side-cut purified acetic acid (7B) in the condenser seems to hardly generate a noncondensable gas. For example, in cooling the purified acetic acid (7B), the noncondensable gas has a volume proportion of 1% or less (e.g., 0.1% or less) in the whole fluid (or phases). Thus, the purified acetic acid (8B) (the line 81) from the condenser is different from the above side-cut purified acetic acid (8B) in only temperature from each other (for example, the former purified acetic acid (8B) has a temperature of 17 to 60° C.) and have substantially the same (or similar) composition.

The composition of the bottom stream (7C) (lines 77, 78, 79) is substantially the same as (or similar to) the composition of side-cut purified acetic acid (7B) (the line 75), for example, except Li and/or Rh. For example, the concentrations of Li and Rh are as follows.

Incidentally, oxygen contained in the distillation column (7) causes coloring of the side-cut purified acetic acid (7B) (the line 75) and stronger coloring of the bottom stream (7C).

TABLE 28

| | Range | Preferred range | More preferred range |
|---|---|---|---|
| Li | 1 ppm or less (0.1 ppb to 1000 ppb) | 1 to 100 ppb | 5 to 50 ppb |
| Rh | 1 ppm or less (10 ppt to 500 ppb) | 100 ppt to 100 ppb | 500 ppt to 30 ppb |

(8) Ion Exchange Step

In order to separate an iodine compound from the acetic acid stream (7B) from the purification step (purification distillation column) (7), the acetic acid stream (7B) is cooled and treated in an ion exchange tank (8) to give purified acetic acid stream (8A). The purified acetic acid stream (8A) is sent to the product tank T5 for storage via a line 82.

For example, the concentration of oxygen and the composition of other components of the acetic acid stream 82 treated in the ion exchange tank (8) may be substantially the same as (or similar to) those of the side-cut purified acetic acid (7B) (the line 75), except for components to be removed by ion exchange.

As an ion exchanger in the ion exchange tank (8), there may be used an ion exchanger capable of removing or adsorbing an iodine compound (e.g., a zeolite, an activated carbon, and an ion exchange resin), particularly, a cation exchange resin. The cation exchange resin may be a slightly acidic cation exchange resin. A preferred cation exchange resin may include a strongly acidic cation exchange resin, for example, a macroreticular ion exchange resin. The ion exchanger may have at least a part of an active site replaced with or exchanged for a metal which may include silver Ag, mercury Hg, and/or copper Cu. Examples of the active site may include a cationic group such as a sulfone group, a carboxyl group, a phenolic hydroxyl group, and a phosphine group. In other words, the ion exchanger may be a metal-supported ion exchanger. For example, the ion exchanger may be a metal-supported ion exchanger in which about 10 to 80% by mol, preferably about 25 to 75% by mol, and more preferably 30 to 70% by mol of the active site is replaced with the metal (e.g., silver Ag).

The ion exchanger (e.g., a silver-supported ion exchange resin) is usually fed or filled in the ion exchange column or treatment unit. The contact of the acetic acid stream with the ion exchanger (preferably the running or passing of the acetic acid stream through the ion exchanger) enables the iodine compound to be removed. The contact of the acetic acid stream with the ion exchanger (or the running or passing of the acetic acid stream through the ion exchanger), if necessary, under heating continuously or stepwise, achieves prevention of the metal from flowing out of the ion exchanger and effective removal of the iodine compound. The ion exchange column may include a packed column having at least an ion exchanger (e.g., a metal-supported ion exchanger) packed therein, and a column provided with an ion exchanger bed (e.g., a bed having a granular ion exchanger) (a guard bed). The ion exchange column may be filled or packed with another ion exchanger (e.g., a cation exchange resin, an anion exchange resin, and a nonion exchange resin) in addition to the ion exchanger. Moreover, the acetic acid stream may be subjected to the ion exchange treatment with a column filled or packed with the ion exchanger and a column filled or packed with another ion exchanger. For example, the treatment unit may be provided with the anion exchange resin column and an ion exchange column containing a metal-supported ion exchange resin; the ion exchange column may be located in a downstream side of the anion exchange resin or in an upstream side thereof. The details of the former embodiment may be referred to, for example, WO02/062740.

The temperature of the ion exchange treatment may be a temperature of, for example, about 18 to 100° C., preferably about 30 to 70° C., and more preferably about 40 to 60° C. The flow rate of the acetic acid stream may be, for example, about 3 to 15 bed volume/h, preferably about 5 to 12 bed volume/h, and more preferably about 6 to 10 bed volume/h for a removal column having a guard bed.

The purification section (purification step group or purification unit group) (4) may comprise at least one step selected from the group consisting of the dehydration step (5), the higher boiling component removing step (6), the purification step (purification distillation column) (7), and the ion exchange step (8). The purification section (4) usually comprises at least the dehydration step (5) and the higher boiling component removing step (6). The ion exchange step (8) may be carried out after any step of the purification section (4), for example, the dehydration step (5) and/or the higher boiling component removing step (6), or may be carried out between the higher boiling component removing step (6) and the purification step (purification distillation column) (7).

(9) Separation Section (Step Group or Unit Group)

As described above, the first overhead (3A) from the first distillation step (3) contains impurities and useful components, such as PRC's, methyl iodide, and methyl acetate. Thus, in the separation section (step group or unit group) (9), at least acetaldehyde is separated from the first overhead (3A). In particular, in the separation section (9), the first overhead (3A) is separated into a stream rich in acetaldehyde and a stream rich in useful methyl iodide.

The separation section (9) may comprise the following steps: (10) a step for condensing the first overhead (3A) to form two liquid phases with upper and lower phases (a liquid-liquid separation step), (11) a step (a first aldehyde separation step or distillation step) for forming a fifth overhead rich in acetaldehyde and methyl iodide from the upper phase and/or the lower phase, (12) a step (an extraction step) for extracting acetaldehyde from the fifth overhead obtained in the step (11) to form an extract rich in acetaldehyde and a raffinate rich in methyl iodide, (13) a step (a second aldehyde separation step or distillation step) for separating an aldehyde from the extract and/or the raffinate, and (14) a step (an alkane separation step or distillation step) for separating an alkane from the upper phase and/or the lower phase.

(10) Liquid-Liquid Separation Step

In the liquid-liquid (or biphasic) separation step (10), the first overhead (3A) (the line 31) is cooled and condensed in a condenser to form a condensate 32 being rich in methyl iodide and containing water or other compounds, and the condensate 32 is separated into two phases, an aqueous phase 38 and an organic phase 39, in the decanter S2. A portion of the condensate (upper phase) is returned to the splitter column (3) for reflux via a reflux line 42, at least a portion of the upper phase (aqueous phase or light phase rich in acetaldehyde) 38 separated in the decanter S2 is recycled to the reactor (1) via a line 41, and at least a portion of the lower phase (organic phase or heavy phase rich in methyl iodide) 39 separated in the decanter S2 is recycled to the reactor (1) via a line 40.

Moreover, at least a portion of the lower phase (organic phase or heavy phase) rich in methyl iodide separated in the decanter S2 is fed to the fifth distillation column (distillation step) (11) via feed lines 111, 112 for forming the fifth overhead rich in acetaldehyde and methyl iodide. The lower phase (organic phase) rich in methyl iodide from the decanter S2 is mixed with a portion (branched stream) 124 of a lower stream (11B) (a line 123) from the fifth distillation column (distillation step) (11), and the mixture is recycled to the reactor (1).

A noncondensable gas (off-gas) 33 that has not been condensed in the condenser is rich in methyl iodide and contains carbon monoxide or other compounds. In the same manner as in the off-gas, the noncondensable gas (off-gas) 33 is fed to the off-gas treatment section (15) together with a noncondensable gas in the decanter S2 via lines 34, 35, 37, and treated in the off-gas treatment section (15). The noncondensable gas (off-gas) is further cooled and condensed in a condenser on the line 34 to form a condensate and a noncondensable gas; the condensate passes through a line 36 and is mixed with the lower phase (organic phase or heavy phase) 39 from a feed line 111, and the noncondensable gas is fed to a decanter S3 via the line 35. A condensate liquefied in the decanter S3 is mixed or merged with the lower phase (organic phase or heavy phase) 39 from the feed line 112, and a noncondensable gas in the decanter S3 passes through the line 37 and is treated in the off-gas treatment section (15).

For example, the composition of the condensate 32 may be substantially the same as (or similar to) that of the first overhead (3A) (the line 31). The composition of the condensate 32 may have a component ratio (content of each component) obtained calculated by subtracting the component ratio of the noncondensable gas (off-gas) 33 that is not condensed in the condenser from the component ratio of the first overhead (3A).

For example, the upper phase (aqueous phase) 38 in the decanter S2 may have the following composition.

TABLE 29

| Average molecular weight 23.26 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 1%) | 1 ppm to 0.1% | 2 ppm to 0.1% |
| CO | 0 to 1% (e.g., 0.1 ppm to 1%) | 1 ppm to 0.1% | 10 ppm to 0.05% |
| $CO_2$ | 0 to 1% (e.g., 0.1 ppm to 1%) | 1 ppm to 0.1% | 10 ppm to 0.05% |
| $CH_4$ | 0 to 1% (e.g., 0.1 ppm to 1%) | 1 ppm to 0.1% | 2 ppm to 0.1% |
| $N_2$ | 0 to 1% (e.g., 0.1 ppm to 1%) | 1 ppm to 0.1% | 2 ppm to 0.1% |
| AD | 0 to 2% (e.g., 0.01 to 2%) | 0.05 to 1% | 0.1 to 0.7% |

TABLE 29-continued

| Average molecular weight 23.26 | Range | Preferred range | More preferred range |
|---|---|---|---|
| MeOH | 0 to 10% (e.g., 10 ppm to 10%) | 100 ppm to 5% | 0.1 to 3% |
| MeI | 0.1 to 15% | 1 to 10% | 2 to 6% |
| MA | 1 to 40% | 5 to 30% | 10 to 25% |
| $H_2O$ | 10 to 95% | 20 to 90% | 40 to 80% |
| AcOH | 1 to 30% | 3 to 20% | 8 to 15% |
| HI | 0 to 1% (e.g., 0.01 ppm to 1%) | 0.1 ppm to 0.5% | 1 ppm to 0.1% |
| FrOH | 0 to 1% (e.g., 0.1 ppm to 1%) | 1 ppm to 0.5% | 10 ppm to 0.1% |
| PrOH | 0 to 1% (e.g., 0.1 ppm to 0.1%) | 1 to 100 ppm | 3 to 50 ppm |
| DME | 0 to 1% (e.g., 0.1 ppm to 1%) | 1 ppm to 0.1% | 10 ppm to 0.05% |
| $(CH_3)_2C=O$ | 0 to 1% (e.g., 1 ppm to 0.5%) | 10 ppm to 0.2% | 50 ppm to 0.1% |
| EtOH | 0 to 1% (e.g., 1 ppm to 0.5%) | 10 ppm to 0.2% | 50 ppm to 0.1% |
| EA | 0 to 1% (e.g., 1 ppm to 0.5%) | 10 ppm to 0.2% | 50 ppm to 0.1% |
| EtI | 0 to 1% (e.g., 1 ppm to 0.5%) | 10 ppm to 0.2% | 50 ppm to 0.1% |
| Li | 0 to 0.1% (e.g., 0.01 ppt to 0.1 ppm) | 0.1 ppt to 0.01 ppm | 1 ppt to 0.001 ppm |
| Rh | 0 to 0.1% (e.g., 0.01 ppt to 0.1 ppm) | 0.1 ppt to 0.01 ppm | 1 ppt to 0.001 ppm |

The composition of the upper phase (aqueous phase) in the line 41 connecting to the reactor and splitter column (3) may also be substantially the same as (or similar to) that of the upper phase (aqueous phase) 38 in the decanter S2.

For example, the lower phase (organic phase) 39 in the decanter S2 may have the following composition.

TABLE 30

| Average molecular weight 119.79 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 1%) | 1 ppm to 0.1% | 2 ppm to 0.1% |
| CO | 0 to 1% (e.g., 0.1 ppm to 1%) | 1 ppm to 0.1% | 10 ppm to 0.05% |
| $CO_2$ | 0 to 1% (e.g., 0.1 ppm to 1%) | 1 ppm to 0.1% | 10 ppm to 0.05% |
| $CH_4$ | 0 to 1% (e.g., 0.1 ppm to 1%) | 1 ppm to 0.1% | 2 ppm to 0.1% |
| $N_2$ | 0 to 1% (e.g., 0.1 ppm to 1%) | 1 ppm to 0.1% | 2 ppm to 0.1% |
| AD | 0 to 2% (e.g., 0.01 to 2%) | 0.05 to 1% | 0.08 to 0.5% |
| MeOH | 0 to 2% (e.g., 1 ppm to 2%) | 10 ppm to 1% | 100 ppm to 0.3% |
| MeI | 20 to 99% | 40 to 95% | 60 to 92% |
| MA | 1 to 40% | 4 to 30% | 7 to 20% |
| $H_2O$ | 0.01 to 20% | 0.1 to 10% | 0.5 to 3% |
| AcOH | 0.01 to 20% | 0.1 to 10% | 0.5 to 3% |
| HI | 0 to 1% (e.g., 0.01 ppm to 0.1%) | 0.1 to 500 ppm | 1 to 100 ppm |
| FrOH | 0 to 1% (e.g., 0.1 ppm to 0.1%) | 1 to 100 ppm | 3 to 50 ppm |
| PrOH | 0 to 1% (e.g., 0.1 ppm to 0.1%) | 1 to 100 ppm | 3 to 30 ppm |
| DME | 0 to 1% (e.g., 1 ppm to 1%) | 10 ppm to 0.5% | 100 ppm to 0.1% |
| $(CH_3)_2C=O$ | 0 to 1% (e.g., 1 ppm to 0.5%) | 10 ppm to 0.2% | 50 ppm to 0.1% |
| EtOH | 0 to 1% (e.g., 1 ppm to 0.5%) | 10 ppm to 0.2% | 50 ppm to 0.1% |
| EA | 0 to 1% (e.g., 1 ppm to 0.5%) | 10 ppm to 0.2% | 50 ppm to 0.1% |
| EtI | 0 to 1% (e.g., 1 ppm to 0.5%) | 10 ppm to 0.2% | 50 ppm to 0.1% |
| Li | 0 to 0.1% (e.g., 0.01 ppt to 0.1 ppm) | 0.1 ppt to 0.01 ppm | 1 ppt to 0.001 ppm |
| Rh | 0 to 0.1% (e.g., 0.01 ppt to 0.1 ppm) | 0.1 ppt to 0.01 ppm | 1 ppt to 0.001 ppm |

For example, the noncondensable gas (off-gas) (the line 33) from the condenser may have the following composition.

TABLE 31

| Average molecular weight 79.89 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., |

TABLE 31-continued

| Average molecular weight 79.89 | Range | Preferred range | More preferred range |
|---|---|---|---|
| | 5%), e.g., less than 3.6% (e.g., 0.1 ppb to 2%), e.g., 1 ppb to 1% (e.g., 10 ppb to 0.5%) | | 100 ppb to 200 ppm) |
| $H_2$ | 1 ppm to 5% | 5 ppm to 2.5% (e.g., 10 ppm to 1%) | 50 ppm to 1% (e.g., 100 ppm to 0.1%) |
| CO | 0.01 to 50% | 0.1 to 30% | 1 to 15% |
| $CO_2$ | 0.01 to 20% | 0.1 to 10% | 0.5 to 5% |
| $CH_4$ | 1 ppm to 10% | 10 ppm to 3% | 100 ppm to 1% |
| $N_2$ | 1 ppm to 10% | 10 ppm to 3% | 100 ppm to 1% |
| AD | 1 ppm to 10% | 10 ppm to 3% | 100 ppm to 1% |
| MeOH | 0 to 1% (e.g., 0.1 ppm to 1%) | 1 ppm to 0.5% | 10 ppm to 0.1% |
| MeI | 1 to 99% | 10 to 95% | 40 to 90% |
| MA | 0.01 to 50% | 0.1 to 20% | 1 to 10% |
| $H_2O$ | 0.001 to 20% | 0.01 to 10% | 0.1 to 5% |
| AcOH | 0.001 to 20% | 0.01 to 10% | 0.1 to 5% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 10% (e.g., 0.1 ppm to 10%) | 1 ppm to 2% | 10 ppm to 1% |
| $(CH_3)_2C{=}O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the noncondensable gas of the line 34 may have the following composition.

TABLE 32

| Average molecular weight 82.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 1 ppm to 5% | 10 ppm to 1% | 100 ppm to 0.1% |
| CO | 0.01 to 50% | 0.1 to 30% | 1 to 15% |
| $CO_2$ | 0.01 to 20% | 0.1 to 10% | 0.5 to 5% |
| $CH_4$ | 1 ppm to 10% | 10 ppm to 3% | 100 ppm to 1% |
| $N_2$ | 1 ppm to 10% | 10 ppm to 3% | 100 ppm to 1% |
| AD | 1 ppm to 10% | 10 ppm to 3% | 100 ppm to 1% |
| MeOH | 0 to 1% (e.g., 0.1 ppm to 1%) | 1 ppm to 0.5% | 10 ppm to 0.1% |
| MeI | 1 to 99% | 10 to 95% | 40 to 90% |
| MA | 0.01 to 50% | 0.1 to 20% | 1 to 20% |
| $H_2O$ | 0.001 to 20% | 0.01 to 10% | 0.1 to 5% |
| AcOH | 0.001 to 20% | 0.01 to 10% | 0.1 to 5% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 10% (e.g., 0.1 ppm to 10%) | 1 ppm to 2% | 10 ppm to 1% |
| $(CH_3)_2C{=}O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the noncondensable gas of the line 35 may have the following composition.

TABLE 33

| Average molecular weight 42.11 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 1 ppm to 10% | 10 ppm to 5% | 100 ppm to 1% |
| CO | 0.01 to 90% | 0.1 to 70% | 1 to 50% |
| $CO_2$ | 0.01 to 30% | 0.1 to 20% | 0.5 to 10% |
| $CH_4$ | 10 ppm to 20% | 100 ppm to 10% | 0.1% to 5% |
| $N_2$ | 10 ppm to 20% | 100 ppm to 10% | 0.1% to 5% |
| AD | 1 ppm to 10% | 10 ppm to 3% | 100 ppm to 1% |
| MeOH | 0 to 1% (e.g., 0.1 ppm to 1%) | 1 ppm to 0.5% | 10 ppm to 0.1% |
| MeI | 1 to 99% | 10 to 90% | 20 to 70% |
| MA | 0.01 to 50% | 0.1 to 20% | 1 to 10% |
| $H_2O$ | 0.001 to 20% | 0.01 to 10% | 0.1 to 5% |
| AcOH | 0 to 10% (e.g., 1 ppm to 10%) | 10 ppm to 5% | 100 ppm to 1% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 10% (e.g., 0.1 ppm to 10%) | 1 ppm to 2% | 10 ppm to 1% |
| $(CH_3)_2C{=}O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the noncondensable gas of the line 36 may have the following composition.

TABLE 34

| Average molecular weight 112.80 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.01 ppm to 1%) | 0.1 ppm to 0.1% | 1 ppm to 0.01% |
| CO | 0 to 1% (e.g., 1 ppm to 1%) | 10 ppm to 0.5% | 100 ppm to 0.1% |
| $CO_2$ | 1 ppm to 1% | 10 ppm to 0.5% | 100 ppm to 0.2% |
| $CH_4$ | 0 to 1% (e.g., 0.1 ppm to 0.1%) | 1 ppm to 0.05% | 10 ppm to 0.01% |
| $N_2$ | 0 to 1% (e.g., 0.1 ppm to 0.1%) | 1 ppm to 0.05% | 10 ppm to 0.01% |
| AD | 100 ppm to 3% | 0.1% to 1% | 0.2% to 6000 ppm |
| MeOH | 0 to 1% (e.g., 1 ppm to 1%) | 10 ppm to 0.5% | 100 ppm to 0.3% |
| MeI | 20 to 99% | 50 to 97% | 70 to 90% |
| MA | 1 to 40% | 5 to 30% | 7 to 20% |
| $H_2O$ | 0.01 to 10% | 0.1 to 8% | 0.5 to 5% |
| AcOH | 0.001 to 5% | 0.01 to 1% | 0.05 to 0.5% |
| HI | 0 to 1% (e.g., 0.01 ppm to 0.1%) | 0.1 to 500 ppm | 1 to 100 ppm |
| FrOH | 0 to 1% (e.g., 0.1 ppm to 0.1%) | 1 to 100 ppm | 3 to 50 ppm |
| PrOH | 0 to 1% (e.g., 0.1 ppm to 0.1%) | 1 to 100 ppm | 3 to 30 ppm |
| DME | 0 to 3% (e.g., 1 ppm to 3%) | 10 ppm to 2% | 100 ppm to 1% |
| $(CH_3)_2C{=}O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the noncondensable gas of the line 37 from the decanter S3 may have the following composition.

TABLE 35

| Average molecular weight 42.11 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01 to 5% | 0.05 to 2% | 0.1 to 1% |
| CO | 1 to 99% | 5 to 80% | 10 to 70% |
| $CO_2$ | 0.1 to 20% | 0.5 to 15% | 1 to 15% |
| $CH_4$ | 0.1 to 20% | 0.5 to 15% | 1 to 10% |
| $N_2$ | 0.1 to 20% | 0.5 to 15% | 1 to 10% |
| AD | 0 to 10% (e.g., 0.001 to 10%) | 0.01 to 5% | 0.1 to 3% |
| MeOH | 0 to 1% (e.g., 1 ppm to 1%) | 5 ppm to 0.5% | 10 ppm to 0.1% |
| MeI | 1 to 95% | 10 to 90% | 20 to 80% |
| MA | 0.01 to 40% | 0.1 to 20% | 1 to 10% |
| $H_2O$ | 0 to 10% (e.g., 0.01 to 10%) | 0.02 to 5% | 0.05 to 2% |
| AcOH | 0 to 1% (e.g., 0.001 to 1%) | 5 ppm to 0.5% | 10 ppm to 0.1% |
| HI | 0 to 1% (e.g., 1 ppt to 0.1%) | 100 ppt to 0.01% | 10 ppb to 1 ppm |
| FrOH | 0 to 1% (e.g., 1 ppb to 0.1%) | 10 ppb to 100 ppm | 100 ppb to 10 ppm |
| PrOH | 0 to 1% (e.g., 1 ppb to 0.1%) | 10 ppb to 100 ppm | 100 ppb to 10 ppm |
| DME | 0 to 1% (e.g., 0.1 ppm to 1%) | 1 ppm to 0.1% | 5 ppm to 0.05% |
| $(CH_3)_2C=O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the composition of the feed line 111 of the lower phase (organic phase or heavy phase) may be substantially the same as (or similar to) the composition of the lower phase (organic phase) 39 in the decanter S2.

For example, the composition of the feed line 112 may be substantially the same as (or similar to) the composition of the lower phase (organic phase) 39 in the decanter S2. Moreover, the composition of the feed line 112 may have a component ratio (content of each component) obtained or calculated by the weighted average of the component ratio of the feed line 111 of the lower phase (organic phase or heavy phase) and the component ratio of the line 36 of the condensate.

The ratio (weight ratio) of the flow rate of the upper phase withdrawn from the decanter S2 relative to that of the lower phase withdrawn from the decanter S2 [the upper phase/the lower phase] may be, for example, about 0.1/1 to 10/1 (e.g., about 0.3/1 to 3/1) and preferably about 0.5/1 to 2/1 (e.g., about 0.7/1 to 1.5/1). The ratio (weight ratio) of the flow rate of the upper phase refluxed to the splitter column (3) relative to that of the upper phase recycled to the reaction system (1) [the former/the latter] may be about 2/1 to 1000/1 (e.g., about 5/1 to 200/1) and preferably about 10/1 to 100/1 (e.g., about 15/1 to 50/1).

The first overhead (3A) may be fed to the first aldehyde separation step (11) without condensation or liquid-liquid separation in the decanter S2.

Alternatively, the first overhead (3A) may biphasically be separated into an upper phase (an aqueous phase or light phase) rich in acetaldehyde and a lower phase (an organic phase or heavy phase) rich in methyl iodide in the decanter, and at least one phase of the upper phase and the lower phase may be fed to the first aldehyde separation step (11) and/or the reactor (1). Moreover, to the reactor (1), a portion of the upper phase (aqueous phase or light phase) is recycled, or, alternatively, the lower phase (organic phase or heavy phase) may be recycled. Further, to the first aldehyde separation step (11), the upper phase (aqueous phase or light phase) may be fed instead of the lower phase (organic phase or heavy phase).

In a case where the first overhead (3A) is cooled successively in sequentially arranged plural condensers successively lower in cooling temperature to form a plurality of condensates successively lower in temperature, a condensate formed by a subsequent condenser has a higher concentration of acetaldehyde compared with a process liquid (a condensate) formed by a first condenser. Accordingly, a condensate having a high concentration of acetaldehyde may be fed to the fourth distillation step (11) to separate acetaldehyde from the condensate.

(11) First Aldehyde Separation Step (Fifth Distillation Step)

The condensate of the line 112 from the decanter S2 in the liquid-liquid separation step (10) [at least the portion 112 of the organic phase or heavy phase 39 being rich in methyl iodide and containing methyl acetate or other compounds] is heated by a heating unit and is then held in a hold tank S4 for gas-liquid separation or degasification treatment to form a condensation mixture (being rich in methyl iodide and containing methyl acetate or other compounds) and a gaseous phase. The condensation mixture from the hold tank S4 is fed, for distillation, to the first aldehyde separation step (fifth distillation step or distillation column) (11) via a line 114 to form a fifth overhead (11A) rich in acetaldehyde and methyl iodide. Specifically, in this embodiment, the organic phase (heavy phase rich in methyl iodide) formed in the liquid-liquid separation step (10) is fed to the first aldehyde separation step (distillation step or distillation column) (11) via the feed lines 112, 114, and is distilled to form a fifth overhead (11A) and a lower stream (11B); the fifth overhead (11A) is withdrawn from a top or upper part of the column via a withdrawing line (a line 115), and the lower stream (11B) is withdrawn via a bottom line 123. The gaseous phase from the hold tank S4, which contains methyl iodide or other compounds, is mixed, through a line 113, with the noncondensable gas from the decanter S2 of the liquid-liquid separation step (10), and the mixture is cooled and condensed in a condenser.

The lower stream (11B) 123 contains acetic acid, water, or other compounds. A first portion of the lower stream (11B) is recycled to the first aldehyde separation step (distillation column) (11); a second portion (or residual portion) of the lower stream (11B) is mixed, through a line 124, with the lower phase (organic phase), rich in methyl iodide, from the decanter S2, and the resulting mixture is recycled to the reactor (1).

The fifth overhead (11A) (the line 115) is rich in acetaldehyde and methyl iodide. The fifth overhead (11A) is cooled and condensed in condensers to form condensates and a noncondensable gases. The condensates are sent to a hold tank T6 for holding or storage via lines 117, 119. The noncondensable gases, which contain methyl iodide or other compounds, are mixed, through lines 116, 118, with the noncondensable gas from the decanter S2 of the liquid-liquid separation step (10), and the mixture is cooled and condensed in a condenser. Moreover, a portion of the condensate from the hold tank T6 is returned to the first aldehyde separation step (distillation step) (11) via lines 120, 121 for reflux, and the residual portion of the condensate is cooled in a condenser on a line 122 and is fed to a water extraction unit (water extractive distillation column) (12) of the extraction step (12) via a line 125.

For example, the condensate (the line 114) from the decanter S4 may have the following composition.

Incidentally, the composition of the condensate (the line 114) from the decanter S4 may be substantially the same as (or similar to) the composition of the organic phase 39 in the decanter S2 or the composition of the feed line 112, except for the concentrations of components in the noncondensable gas and the concentration of DME. Thus, the following table shows the concentrations of components in the noncondensable gas and the concentration of DME.

TABLE 36

| Average molecular weight 119.03 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 0.1%) | 1 ppm to 0.01% | 2 to 500 ppm |
| CO | 0 to 1% (e.g., 0.1 ppm to 0.1%) | 1 ppm to 0.01% | 1 to 500 ppm |
| $CO_2$ | 0 to 1% (e.g., 0.1 ppm to 0.1%) | 1 ppm to 0.01% | 1 to 500 ppm |
| $CH_4$ | 0 to 1% (e.g., 0.1 ppm to 0.1%) | 1 ppm to 0.01% | 1 to 500 ppm |
| $N_2$ | 0 to 1% (e.g., 0.1 ppm to 1%) | 1 ppm to 0.1% | 2 ppm to 0.1% |
| DME | 0 to 1% (e.g., 0.01 ppm to 0.1%) | 0.05 to 100 ppm | 0.5 to 20 ppm |

For example, the noncondensable gas (the line 113) from the decanter S4 may have the following composition.

TABLE 37

| Average molecular weight 100.95 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 5% (e.g., 1 ppm to 5%) | 10 ppm to 1% | 100 ppm to 0.1% |
| CO | 0.001 to 10% | 0.01 to 5% | 0.1 to 1% |
| $CO_2$ | 0.001 to 20% | 0.01 to 10% | 0.1 to 2% |
| $CH_4$ | 0 to 5% (e.g., 1 ppm to 5%) | 10 ppm to 1% | 100 ppm to 0.1% |
| $N_2$ | 0 to 5% (e.g., 1 ppm to 5%) | 10 ppm to 1% | 100 ppm to 0.1% |
| AD | 0.001 to 10% | 0.01 to 5% | 0.1 to 1% |
| MeOH | 0 to 1% (e.g., 1 ppm to 1%) | 5 ppm to 0.5% | 10 ppm to 0.1% |
| MeI | 1 to 99% | 10 to 95% | 40 to 90% |
| MA | 0.01 to 50% | 0.1 to 20% | 1 to 10% |
| $H_2O$ | 0.001 to 20% | 0.01 to 10% | 0.1 to 5% |
| AcOH | 0 to 2% (e.g., 0.001 to 2%) | 0.005 to 1% | 0.01 to 0.5% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 1% (e.g., 0.1 ppm to 1%) | 1 ppm to 0.1% | 5 ppm to 0.05% |
| $(CH_3)_2C=O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |

TABLE 37-continued

| Average molecular weight 100.95 | Range | Preferred range | More preferred range |
|---|---|---|---|
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the fifth overhead (11A) (the line 115) may have the following composition.

TABLE 38

| Average molecular weight 71.30 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.01 ppm to 1%) | 0.1 ppm to 0.1% | 1 ppm to 0.01% |
| CO | 0 to 3% (e.g., 0.1 ppm to 3%) | 1 ppm to 1% | 10 ppm to 0.1% |
| $CO_2$ | 0 to 3% (e.g., 0.1 ppm to 3%) | 1 ppm to 1% | 10 ppm to 0.1% |
| $CH_4$ | 0 to 1% (e.g., 0.01 ppm to 1%) | 0.1 ppm to 0.1% | 1 ppm to 0.01% |
| $N_2$ | 0 to 1% (e.g., 0.01 ppm to 1%) | 0.1 ppm to 0.1% | 1 ppm to 0.01% |
| AD | 5 to 90% (e.g., 10 to 80%) | 15 to 75% | 20 to 60% |
| MeOH | 0 to 5% (e.g., 0.1 ppm to 5%) | 1 ppm to 1% | 10 ppm to 0.1% |
| MeI | 5 to 95% (e.g., 10 to 90%) | 20 to 85% | 40 to 80% |
| MA | 0.1 ppm to 5% | 1 ppm to 1% | 10 ppm to 0.5% |
| $H_2O$ | 1 ppm to 10% | 10 ppm to 2% | 100 ppm to 1% |
| AcOH | 0 to 1% (e.g., 1 ppb to 1%) | 10 ppb to 0.1% | 100 ppb to 0.01% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 1% (e.g., 0.1 ppm to 1%) | 1 ppm to 0.1% | 5 ppm to 0.05% |
| $(CH_3)_2C=O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the condensates (lines 120, 121, 122) of the fifth overhead (the line 115) from the condenser (s) may have the following composition.

Incidentally, the composition of the condensates (lines 120, 121, 122) may be substantially the same as (or similar to) the composition of the fifth overhead (11A) (the line 115), except for the concentrations of components in the noncondensable gas. Thus, the following table shows the concentrations of components in the noncondensable gas.

For example, the noncondensable gas (line 118) of the fifth overhead (the line 115) from the condenser(s) may have the following composition.

As described above, an inactive gas (nitrogen gas, carbon monoxide gas) purge may be introduced in order to control the pressure of a distillation column and to protect a level gauge, a pressure gauge, a thermometer, or other measuring instruments, from a condensable gas. The composition of the noncondensable gas in the lines 115, 116, 118 significantly changes due to the introduction of such a component, and the concentrations of other components also significantly change due to the dilution with the introduced inactive gas.

TABLE 39

| Average molecular weight 71.33 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppb to 0.1%) | 10 ppb to 0.01% | 100 ppb to 0.001% |
| CO | 0 to 1% (e.g., 0.01 ppm to 1%) | 0.1 ppm to 0.1% | 1 ppm to 0.01% |
| $CO_2$ | 0 to 2% (e.g., 0.1 ppm to 2%) | 1 ppm to 1% | 10 ppm to 0.5% |
| $CH_4$ | 0 to 1% (e.g., 0.01 ppm to 1%) | 0.1 ppm to 0.1% | 1 ppm to 0.01% |
| $N_2$ | 0 to 1% (e.g., 0.01 ppm to 1%) | 0.1 ppm to 0.1% | 1 ppm to 0.01% |

TABLE 40

| Average molecular weight 39.25 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.1 ppm to 1%) | 1 ppm to 0.1% | 10 ppm to 0.01% |
| CO | 0.01 to 20% | 0.1 to 15% | 0.5 to 10% |
| $CO_2$ | 0.01 to 70% | 0.1 to 60% | 0.5 to 50% |
| $CH_4$ | 0 to 1% (e.g., 0.1 ppm to 1%) | 1 ppm to 0.1% | 10 ppm to 0.01% |
| $N_2$ | 10 ppm to 70% | 100 ppm to 50% | 0.1% to 40% |
| AD | 1 ppm to 30% | 10 ppm to 25% | 100 ppm to 20% |
| MeOH | 0 to 1% (e.g., 0.1 ppm to 1%) | 1 ppm to 0.5% | 10 ppm to 0.1% |
| MeI | 1 to 50% | 2 to 40% | 5 to 25% |
| MA | 0 to 10% (e.g., 5 ppm to 1%) | 10 ppm to 0.5% | 25 ppm to 0.1% |
| $H_2O$ | 0 to 10% (e.g., 10 ppm to 5%) | 50 ppm to 1% | 50 ppm to 0.1% |
| AcOH | 0 to 1% (e.g., 1 ppm to 1%) | 10 ppm to 0.3% | 100 ppm to 0.1% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 2% (e.g., 0.1 ppm to 1%) | 1 ppm to 1% | 10 ppm to 0.1% |
| $(CH_3)_2C{=}O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the lower streams (11B) 123, 124 of the fifth distillation column (11) may have the following composition.

TABLE 41

| Average molecular weight 119.33 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 1% (e.g., 1 ppt to 0.1%) | 10 ppt to 0.01% | 100 ppt to 0.001% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.1%) | 10 ppt to 0.01% | 100 ppt to 0.001% |
| AD | 0 to 1% (e.g., 1 ppm to 0.5%) | 10 ppm to 0.2% | 100 to 700 ppm |
| MeOH | 0 to 1% (e.g., 0.1 ppm to 0.5%) | 1 ppm to 0.1% | 10 ppm to 0.01% |
| MeI | 1 to 99% (e.g., 10 to 95%) | 30 to 98% (e.g., 50 to 95%) | 70 to 90% |
| MA | 1 to 40% | 5 to 30% | 7 to 20% |
| $H_2O$ | 0.01 to 30% | 0.1 to 10% | 0.5 to 5% |
| AcOH | 0.01 to 10% | 0.1 to 5% | 0.5 to 3% |
| HI | 0 to 1% (e.g., 0.01 ppm to 0.1%) | 0.05 ppm to 0.2% (e.g., 0.1 to 500 ppm) | 0.5 ppm to 0.1% (e.g., 1 to 100 ppm) |
| FrOH | 0 to 1% (e.g., 1 ppb to 100 ppm) | 10 ppb to 10 ppm | 100 ppb to 5 ppm |
| PrOH | 0 to 1% (e.g., 1 ppb to 100 ppm) | 10 ppb to 10 ppm | 100 ppb to 5 ppm |
| DME | 0 to 1% (e.g., 1 ppb to 100 ppm) | 5 ppb to 0.5% (e.g., 10 ppb to 10 ppm) | 50 ppb to 0.1% (e.g., 100 ppb to 5 ppm) |
| $(CH_3)_2C{=}O$ | 0 to 1% (e.g., 1 ppb to 100 ppm) | 10 ppb to 10 ppm | 100 ppb to 5 ppm |
| EtOH | 0 to 1% (e.g., 1 ppb to 100 ppm) | 10 ppb to 10 ppm | 100 ppb to 5 ppm |
| EA | 0 to 1% (e.g., 1 ppb to 100 ppm) | 10 ppb to 10 ppm | 100 ppb to 5 ppm |
| EtI | 0 to 1% (e.g., 1 ppb to 100 ppm) | 10 ppb to 10 ppm | 100 ppb to 5 ppm |
| Li | 0 to 0.1% (e.g., 0.01 ppt to 100 ppb) | 1 ppt to 10 ppb | 10 ppt to 1 ppb |
| Rh | 0 to 0.1% (e.g., 0.01 ppt to 100 ppb) | 1 ppt to 10 ppb | 10 ppt to 1 ppb |

In the first aldehyde separation step (distillation step or distillation column) (11), the condensate formed in the liquid-liquid separation step (10) is distilled to form a fifth overhead (11A) rich in acetaldehyde and methyl iodide. The upper phase (aqueous phase, light phase rich in acetaldehyde) may be distilled, the lower phase (organic phase, heavy phase rich in methyl iodide) may be distilled, or the condensation mixture of the upper phase and the lower phase may be distilled. As the distillation column of the fifth distillation step (11), there may be used a plate column, a packed column, or other columns.

(12) Extraction Step (Extractive Distillation Column or Sixth Distillation Column)

In the water extraction unit (water extractive distillation column) of the extraction step (12), acetaldehyde is extracted from the fifth overhead (11A) (a condensate cooled in a condenser), forming an extract rich in acetaldehyde and a raffinate rich in methyl iodide. Specifically, to the extraction step (extractive distillation column or sixth distillation column) (12), the condensate and an extractant (water) are fed from a feed line 125 and a lower feed line 126, respectively. In the extraction step (water extraction column) (12), the fifth overhead (11A) is separated into a water extract (an extract containing acetaldehyde) (12A) withdrawn from the column top or via an upper withdrawing line 131, and a raffinate (12B) rich in methyl iodide withdrawn via a bottom line 132. The raffinate 132 may be discharged as a waste fluid or may be recycled to the reactor (1). The water extract 131 is further fed to the second aldehyde separation step (distillation step or distillation column) (13).

For example, the extractant (water) from the feed line 126 may have the following composition.

TABLE 42

| Average molecular weight 18.02 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 1%) | 10 ppt to 0.1% | 100 ppt to 0.01% |
| CO | 0 to 1% (e.g., 1 ppt to 1%) | 10 ppt to 0.1% | 100 ppt to 0.01% |
| $CO_2$ | 0 to 1% (e.g., 1 ppt to 1%) | 10 ppt to 0.1% | 100 ppt to 0.01% |
| $CH_4$ | 0 to 1% (e.g., 1 ppt to 1%) | 10 ppt to 0.1% | 100 ppt to 0.01% |
| $N_2$ | 0 to 1% (e.g., 1 ppt to 1%) | 10 ppt to 0.1% | 100 ppt to 0.01% |
| AD | 0 to 0.01% (e.g., 0.001 to 100 ppm) | 0.01 to 50 ppm | 0.1 to 10 ppm |
| MeOH | 0 to 0.01% (e.g., 0.001 to 100 ppm) | 0.01 to 50 ppm | 0.1 to 10 ppm |
| MeI | 0 to 0.01% (e.g., 0.001 to 100 ppm) | 0.01 to 50 ppm | 0.1 to 10 ppm |
| MA | 0 to 0.01% (e.g., 0.001 to 100 ppm) | 0.01 to 50 ppm | 0.1 to 10 ppm |
| $H_2O$ | 99 to 100% | 99.5 to 99.999% | 99.9 to 99.99% |
| AcOH | 0 to 1% (e.g., 0 to 0.01%) | 0.01 to 50 ppm | 0.1 to 10 ppm |
| HI | 0 to 0.01% (e.g., 0.001 to 100 ppm) | 0.01 to 50 ppm | 0.1 to 10 ppm |
| FrOH | 0 to 0.01% (e.g., 0.001 to 100 ppm) | 0.01 to 50 ppm | 0.1 to 10 ppm |
| PrOH | 0 to 0.01% (e.g., 0.001 to 100 ppm) | 0.01 to 50 ppm | 0.1 to 10 ppm |
| DME | 0 to 0.01% (e.g., 0.001 to 100 ppm) | 0.01 to 50 ppm | 0.1 to 10 ppm |
| $(CH_3)_2C=O$ | 0 to 0.01% (e.g., 0.001 to 100 ppm) | 0.01 to 50 ppm | 0.1 to 10 ppm |
| EtOH | 0 to 0.01% (e.g., 0.001 to 100 ppm) | 0.01 to 50 ppm | 0.1 to 10 ppm |
| EA | 0 to 0.01% (e.g., 0.001 to 100 ppm) | 0.01 to 50 ppm | 0.1 to 10 ppm |
| EtI | 0 to 0.01% (e.g., 0.001 to 100 ppm) | 0.01 to 50 ppm | 0.1 to 10 ppm |
| Li | 0 to 0.1% (e.g., 0 to 1 ppm) | 1 ppt to 10 ppb | 10 ppt to 1 ppb |
| Rh | 0 to 0.1% (e.g., 0 to 1 ppm) | 1 ppt to 10 ppb | 10 ppt to 1 ppb |

For example, the water extract 131 may have the following composition.

TABLE 43

| Average molecular weight 21.43 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0.1% or less (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 5% (e.g., 1 ppb to 5%) | 10 ppt to 3% | 100 ppt to 1% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.5%) | 10 ppt to 0.1% | 100 ppt to 0.01% |
| AD | 1 to 50% | 3 to 40% | 5 to 30% |
| MeOH | 0 to 1% (e.g., 0.1 ppm to 0.5%) | 1 ppm to 0.1% | 10 ppm to 0.01% |
| MeI | 0 to 25% (e.g., 0.1 to 20%) | 0.5 to 20% | 1 to 15% |
| MA | 0 to 2% (e.g., 10 ppb to 1%) | 100 ppb to 1% | 1 ppm to 0.5% |
| $H_2O$ | 10 to 98% | 50 to 95% | 60 to 90% |
| AcOH | 0 to 5% (e.g., 10 ppb to 1%) | 100 ppb to 3% | 1 ppm to 1% |
| HI | 0 to 1% (e.g., 0.01 ppm to 0.1%) | 0.1 to 500 ppm | 1 to 100 ppm |
| FrOH | 0 to 1% (e.g., 0.1 ppb to 100 ppm) | 1 ppb to 10 ppm | 10 ppb to 1 ppm |
| PrOH | 0 to 1% (e.g., 0.1 ppb to 100 ppm) | 1 ppb to 10 ppm | 10 ppb to 1 ppm |
| DME | 0 to 1% (e.g., 10 ppb to 1%) | 100 ppb to 0.2% | 1 to 500 ppm |
| $(CH_3)_2C=O$ | 0 to 1% (e.g., 1 ppb to 100 ppm) | 10 ppb to 10 ppm | 100 ppb to 5 ppm |
| EtOH | 0 to 1% (e.g., 1 ppb to 100 ppm) | 10 ppb to 10 ppm | 100 ppb to 5 ppm |
| EA | 0 to 1% (e.g., 1 ppb to 100 ppm) | 10 ppb to 10 ppm | 100 ppb to 5 ppm |

TABLE 43-continued

| Average molecular weight 21.43 | Range | Preferred range | More preferred range |
|---|---|---|---|
| EtI | 0 to 1% (e.g., 1 ppb to 100 ppm) | 10 ppb to 10 ppm | 100 ppb to 5 ppm |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For example, the raffinate 132 may have the following composition.

TABLE 44

| Average molecular weight 115.86 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 5% (e.g., 1 ppt to 5%) | 10 ppt to 2% | 100 ppt to 1% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.5%) | 10 ppt to 0.1% | 100 ppt to 0.01% |
| AD | 0.1 to 30% | 1 to 20% | 5 to 15% |
| MeOH | 0 to 1% (e.g., 0.01 ppm to 1%) | 0.1 ppm to 0.1% | 1 to 100 ppm |
| MeI | 80 to 100% | 90 to 99.999% | 99 to 99.99% |
| MA | 0.1 ppm to 2% | 1 ppm to 1% | 10 ppm to 0.5% |
| $H_2O$ | 10 ppm to 2% | 100 ppm to 1% | 500 ppm to 0.5% |
| AcOH | 0 to 1% (e.g., 10 ppb to 1%) | 100 ppb to 0.5% | 1 ppm to 0.1% |
| HI | 0 to 1% (e.g., 1 ppb to 0.1%) | 10 ppb to 500 ppm | 100 ppb to 100 ppm |
| FrOH | 0 to 1% (e.g., 0.1 ppb to 100 ppm) | 1 ppb to 10 ppm | 10 ppb to 1 ppm |
| PrOH | 0 to 1% (e.g., 0.1 ppb to 100 ppm) | 1 ppb to 10 ppm | 10 ppb to 1 ppm |
| DME | 0 to 1% (e.g., 10 ppb to 1%) | 100 ppb to 0.2% | 1 to 500 ppm |
| $(CH_3)_2C=O$ | 0 to 1% (e.g., 1 ppb to 100 ppm) | 10 ppb to 10 ppm | 100 ppb to 5 ppm |
| EtOH | 0 to 1% (e.g., 1 ppb to 100 ppm) | 10 ppb to 10 ppm | 100 ppb to 5 ppm |
| EA | 0 to 1% (e.g., 1 ppb to 100 ppm) | 10 ppb to 10 ppm | 100 ppb to 5 ppm |
| EtI | 0 to 1% (e.g., 1 ppb to 100 ppm) | 10 ppb to 10 ppm | 100 ppb to 5 ppm |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

For the water extractive distillation, the condensation mixture is fed to the water extractive distillation column, and an extractant (water) is fed to an upper part of the distillation column for forming a raffinate rich in methyl iodide as an overhead and a water extract (an extract containing acetaldehyde) as a bottom liquid. As the water extractive distillation column, there may be used a plate column, a packed column, or other columns.

In the extraction step (12), an extraction unit (extractor) may be used instead of the extractive distillation. The extraction unit may comprise one or a plurality of extractors. As each one of the extractors, for example, there may be used a combination of a mixer with a settler, a combination of a static mixer with a decanter, a rotated disk contactor (RDC), a Karr column, a spray column, a packed column, a perforated plate column, a baffled column, and a pulse column. The extractor (extraction column) may be a single-stage extraction unit for extracting an object from a mixture of the object and water and separating the mixture into liquid phases, or may have a plurality of the single-stage extraction units arranged in a cascade manner. For example, the extractor may be a multi-stage extraction unit that comprises a plurality of extractors (each extractor having a theoretical number of plates of 1) for sequential extraction. Moreover, the extractor may be a multi-stage extraction unit in which a plurality of extractors has been installed in a single unit, for example, a single extraction unit having the theoretical number of plates equivalent to a multi-stage extraction unit (the theoretical number of plates corresponding to multi-stage extraction). Moreover, the extraction may be either a batch system or a continuous system, or may be performed in either a parallel extraction or a countercurrent extraction.

Further, at least a portion of the raffinate may be recycled to the reactor, or at least a portion of the water extract may be fed to the succeeding second aldehyde separation step (distillation step or distillation column) (13).

(13) Second Aldehyde Separation Step (Seventh Distillation Column)

In the second aldehyde separation step (seventh distillation step or distillation column) (13), the water extract 131 rich in acetaldehyde is distilled to give a sixth overhead (13A) withdrawn from a top or upper part of the column via a withdrawing line 141 and a lower stream (13B) withdrawn via a bottom line 146, in the same manner as in the first aldehyde separation step (distillation step or distillation column) (11).

The lower stream (13B) (the line 146) contains water or other compounds. A first portion of the lower stream (13B) is recycled to the second aldehyde separation step (distillation column) (13), and a second portion (or residual portion) of the lower stream (13B) is sent to an incinerator via a line 146 for incineration.

The sixth overhead (13A), which is rich in acetaldehyde, is cooled and condensed in condenser on the withdrawing line 141 to form a condensate and a noncondensable gas. The condensate is held in a hold tank T7 via a line 142, a portion of the condensate is returned to the second aldehyde separation step (distillation step) (13) for reflux via a reflux line 143, and the residual portion of the condensate is incinerated by an incineration unit via a line 144. Moreover, the noncondensable gas that is not condensed in the condenser is mixed, through a line 145, with the noncondensable gas from the decanter S2 of the liquid-liquid separation step (10), and the mixture is cooled and condensed in a condenser.

For example, the sixth overhead (13A) (the line 141) may have the following composition.

TABLE 45

| Average molecular weight 42.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 1% (e.g., 1 ppt to 1%) | 10 ppt to 0.5% | 100 ppt to 0.05% |
| $CH_4$ | 0 to 1% (e.g., 1 ppt to 0.1%) | 10 ppt to 0.01% | 100 ppt to 0.001% |
| $N_2$ | 0 to 5% (e.g., 1 ppt to 5%) | 10 ppt to 1% | 100 ppt to 0.1% |
| AD | 50 to 99% | 70 to 95% | 80 to 90% |
| MeOH | 0 to 5% (e.g., 0.1 ppm to 5%) | 1 ppm to 1% | 10 ppm to 0.1% |
| MeI | 0.1 to 30% | 0.5 to 20% | 1 to 10% |
| MA | 0.1 ppm to 3% | 1 ppm to 1% | 10 ppm to 0.5% |
| $H_2O$ | 0.1 to 30% | 1 to 20% | 3 to 10% |
| AcOH | 0 to 1% (e.g., 0.1 ppb to 0.1%) | 1 ppb to 0.01% | 10 ppb to 0.001% |
| HI | 0 to 1% (e.g., 1 ppt to 0.5%) | 10 ppt to 0.1% | 100 ppb to 200 ppm |
| FrOH | 0 to 1% (e.g., 0.1 ppb to 100 ppm) | 1 ppb to 10 ppm | 10 ppb to 1 ppm |
| PrOH | 0 to 1% (e.g., 0.1 ppb to 100 ppm) | 1 ppb to 10 ppm | 10 ppb to 1 ppm |
| DME | 0 to 1% (e.g., 10 ppb to 1%) | 100 ppb to 0.2% | 1 to 500 ppm |
| $(CH_3)_2C=O$ | 0 to 1% (e.g., 1 ppb to 100 ppm) | 10 ppb to 10 ppm | 100 ppb to 5 ppm |
| EtOH | 0 to 1% (e.g., 1 ppb to 100 ppm) | 10 ppb to 10 ppm | 100 ppb to 5 ppm |
| EA | 0 to 1% (e.g., 1 ppb to 100 ppm) | 10 ppb to 10 ppm | 100 ppb to 5 ppm |
| EtI | 0 to 1% (e.g., 1 ppb to 100 ppm) | 10 ppb to 10 ppm | 100 ppb to 5 ppm |
| Li | 0 to 0.1% (e.g., 0.01 ppt to 100 ppb) | 0.1 ppt to 10 ppb | 1 ppt to 1 ppb |
| Rh | 0 to 0.1% (e.g., 0.01 ppt to 100 ppb) | 0.1 ppt to 10 ppb | 1 ppt to 1 ppb |

The composition of the condensates 143, 144 from the condenser may be substantially the same as (or similar to) the composition of the sixth overhead (13A) (the line 141), except for the concentrations of components in the noncondensable gas. Thus, the following table shows the concentrations of components in the noncondensable gas.

TABLE 46

| Average molecular weight 42.08 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 1 ppt to 0.1%) | 10 ppt to 0.01% | 100 ppt to 0.001% |
| CO | 0 to 1% (e.g., 1 ppt to 0.01%) | 10 ppt to 0.001% | 100 ppt to 0.0001% |
| $CO_2$ | 0 to 1% (e.g., 1 ppt to 0.1%) | 10 ppt to 0.05% | 100 ppt to 0.005% |
| $CH_4$ | 0 to 1% (e.g., 1 ppt to 0.01%) | 10 ppt to 0.001% | 100 ppt to 0.0001% |
| $N_2$ | 0 to 1% (e.g., 1 ppt to 0.5%) | 10 ppt to 0.1% | 100 ppt to 0.01% |

For example, the noncondensable gas 145 from the condenser may have the following composition.

As described above, the composition of the noncondensable gas 145 significantly changes according to the amount of the inactive purge gas.

In the second aldehyde separation step (distillation step or distillation column) (13), at least a portion of the raffinate 132 rich in methyl iodide may be distilled instead of at least a portion of the water extract 131; at least a portion of the

TABLE 47

| Average molecular weight 37.56 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 1% (e.g., 0.1 ppm to 1%) | 1 ppm to 0.1% | 10 ppm to 0.01% |
| CO | 0.01 to 60% | 0.1 to 50% | 0.5 to 40% |
| $CO_2$ | 0.01 to 60% | 0.1 to 50% | 0.5 to 40% |
| $CH_4$ | 0 to 3% (e.g., 0.1 ppm to 2%) | 1 ppm to 1% | 10 ppm to 0.5% |
| $N_2$ | 0 to 3% (e.g., 10 ppm to 2%) | 50 ppm to 1% | 100 ppm to 0.5% |
| AD | 0.1 to 90% | 1 to 80% | 5 to 70% |
| MeOH | 0 to 1% (e.g., 0.1 ppm to 1%) | 1 ppm to 0.5% | 10 ppm to 0.1% |
| MeI | 100 ppm to 50% | 0.1 to 20% | 0.5 to 5% |
| MA | 0.001 to 10% | 0.01 to 5% | 0.1 to 2% |
| $H_2O$ | 0 to 1% (e.g., 0.0001 to 2%) | 0.001 to 1% | 0.01 to 0.1% |
| AcOH | 0 to 1% (e.g., 0.0001 to 2%) | 0.001 to 1% | 0.01 to 0.1% |
| HI | 0 to 1% (e.g., 1 ppb to 0.1%) | 10 ppb to 0.01% | 100 ppb to 0.001% |
| FrOH | 0 to 1% (e.g., 1 ppb to 0.1%) | 10 ppb to 0.01% | 100 ppb to 0.001% |
| PrOH | 0 to 1% (e.g., 1 ppb to 0.1%) | 10 ppb to 0.01% | 100 ppb to 0.001% |
| DME | 0 to 1% (e.g., 0.1 ppm to 10%) | 1 ppm to 2% | 10 ppm to 1% |
| $(CH_3)_2C=O$ | 0 to 1% (e.g., 0.01 ppm to 1%) | 0.1 ppm to 0.1% | 1 ppm to 0.05% |
| EtOH | 0 to 1% (e.g., 0.01 ppm to 1%) | 0.1 ppm to 0.1% | 1 ppm to 0.05% |
| EA | 0 to 1% (e.g., 0.01 ppm to 1%) | 0.1 ppm to 0.1% | 1 ppm to 0.05% |
| EtI | 0 to 1% (e.g., 0.01 ppm to 1%) | 0.1 ppm to 0.1% | 1 ppm to 0.05% |
| Li | 0 to 0.1% (e.g., 0.1 ppt to 100 ppb) | 1 ppt to 10 ppb | 10 ppt to 1 ppb |
| Rh | 0 to 0.1% (e.g., 0.1 ppt to 100 ppb) | 1 ppt to 10 ppb | 10 ppt to 1 ppb |

For example, the lower stream (13B) (the line 146) may have the following composition.

water extract 131 and at least a portion of the raffinate 132 may be distilled to form the overhead (13A) containing

TABLE 48

| Average molecular weight 18.02 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 1% (e.g., 1 ppt to 0.1%) | 10 ppt to 0.01% | 100 ppt to 0.001% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.1%) | 10 ppt to 0.01% | 100 ppt to 0.001% |
| AD | 0 to 1% (e.g., 1 ppm to 0.5%) | 10 ppm to 0.2% | 100 to 700 ppm |
| MeOH | 0 to 1% (e.g., 0.1 ppm to 0.5%) | 1 ppm to 0.1% | 10 ppm to 0.01% |
| MeI | 0 to 1% (e.g., 0.1 ppm to 0.5%) | 1 ppm to 0.1% | 10 ppm to 0.01% |
| MA | 0 to 1% (e.g., 0.1 ppm to 0.5%) | 1 ppm to 0.1% | 10 ppm to 0.01% |
| $H_2O$ | 90 to 100% | 98 to 99.999% | 99 to 99.99% |
| AcOH | 0 to 1% (e.g., 0.1 ppm to 0.5%) | 1 ppm to 0.1% | 10 ppm to 0.01% |
| HI | 0 to 1% (e.g., 0.01 ppm to 0.1%) | 0.1 to 500 ppm | 1 to 100 ppm |
| FrOH | 0 to 1% (e.g., 1 ppb to 100 ppm) | 10 ppb to 10 ppm | 100 ppb to 5 ppm |
| PrOH | 0 to 1% (e.g., 1 ppb to 100 ppm) | 10 ppb to 10 ppm | 100 ppb to 5 ppm |
| DME | 0 to 1% (e.g., 1 ppb to 100 ppm) | 10 ppb to 10 ppm | 100 ppb to 5 ppm |
| $(CH_3)_2C=O$ | 0 to 1% (e.g., 1 ppb to 100 ppm) | 10 ppb to 10 ppm | 100 ppb to 5 ppm |
| EtOH | 0 to 1% (e.g., 1 ppb to 100 ppm) | 10 ppb to 10 ppm | 100 ppb to 5 ppm |
| EA | 0 to 1% (e.g., 1 ppb to 100 ppm) | 10 ppb to 10 ppm | 100 ppb to 5 ppm |
| EtI | 0 to 1% (e.g., 1 ppb to 100 ppm) | 10 ppb to 10 ppm | 100 ppb to 5 ppm |
| Li | 0 to 0.1% (e.g., 0.01 ppt to 100 ppb) | 1 ppt to 10 ppb | 10 ppt to 1 ppb |
| Rh | 0 to 0.1% (e.g., 0.01 ppt to 100 ppb) | 1 ppt to 10 ppb | 10 ppt to 1 ppb | acetaldehyde. As the distillation column of the fifth distillation step (13), there may be used a plate column, a packed column, or other columns.

(14) Alkane Separation Step (Distillation Step, Eighth Distillation Column)

In the alkane separation step (distillation step) (14), an alkane is separated from the portion 41 of the upper phase and/or the portion 40 of the lower phase formed in the liquid-liquid separation step (10). Specifically, in this embodiment, the portion 40 of the lower phase (organic phase or heavy phase rich in methyl iodide) is distilled in the alkane separation step (distillation step) (14) to give a seventh overhead (14A) withdrawn from a top or upper part of the column via a withdrawing line 151 and a lower stream (14B) withdrawn via a bottom line 152.

A portion of the lower stream (14B) containing an alkane may be heated to be recycled to the alkane separation step (distillation step) (14), and the residual portion of the lower stream (14B) may be sent to an incinerator unit for incineration.

The seventh overhead (14A), which contains acetaldehyde and methyl iodide, is cooled and condensed in a condenser on a withdrawing line 151 to form a condensate and a noncondensable gas. The condensate is held in a tank T8, a portion of the condensate is returned to the alkane separation step (distillation step) (14) for reflux, and the residual portion of the condensate is recycled to the reactor (1). The noncondensable gas is mixed, through a line 113, with the noncondensable gas from the decanter S2 of the liquid-liquid separation step (10), and the mixture is cooled and condensed in a condenser.

For example, the composition of the seventh overhead (14A) (the line 151) may have substantially the same as (or similar to) the composition of the organic phase 39 in the decanter S2.

For example, the lower stream (14B) (the line 152) may have the following composition.

TABLE 49

| Average molecular weight 119.79 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 0.1 ppm to 1%) | 1 ppm to 0.1% | 2 ppm to 0.1% |
| CO | 0 to 1% (e.g., 0.1 ppm to 1%) | 1 ppm to 0.1% | 10 ppm to 0.05% |
| $CO_2$ | 0 to 1% (e.g., 0.1 ppm to 1%) | 1 ppm to 0.1% | 10 ppm to 0.05% |
| $CH_4$ | 0 to 1% (e.g., 0.1 ppm to 1%) | 1 ppm to 0.1% | 2 ppm to 0.1% |
| $N_2$ | 0 to 1% (e.g., 0.1 ppm to 1%) | 1 ppm to 0.1% | 2 ppm to 0.1% |
| AD | 0 to 2% (e.g., 0.01 to 2%) | 0.05 to 1% | 0.08 to 0.5% |
| MeOH | 0 to 2% (e.g., 1 ppm to 2%) | 10 ppm to 1% | 100 ppm to 0.3% |
| MeI | 0 to 1% (e.g., 0.1 ppm to 5%) | 1 ppm to 1% | 10 ppm to 0.1% |
| Alkane ($C_4$ to $C_{20}$) | 1 to 99% | 10 to 80% | 20 to 70% |
| MA | 1 to 40% | 4 to 30% | 7 to 20% |
| $H_2O$ | 0.01 to 20% | 0.1 to 10% | 0.5 to 3% |
| AcOH | 0.1 to 30% | 0.3 to 20% | 0.5 to 15% |
| HI | 0 to 1% (e.g., 0.01 ppm to 0.1%) | 0.1 to 500 ppm | 1 to 100 ppm |
| FrOH | 0 to 1% (e.g., 0.1 ppm to 0.1%) | 1 to 100 ppm | 3 to 50 ppm |
| PrOH | 0 to 1% (e.g., 0.1 ppm to 0.1%) | 1 to 100 ppm | 3 to 30 ppm |
| DME | 0 to 1% (e.g., 1 ppm to 1%) | 10 ppm to 0.5% | 100 ppm to 0.1% |
| $(CH_3)_2C{=}O$ | 0 to 1% (e.g., 1 ppm to 0.5%) | 10 ppm to 0.2% | 50 ppm to 0.1% |
| EtOH | 0 to 1% (e.g., 1 ppm to 0.5%) | 10 ppm to 0.2% | 50 ppm to 0.1% |
| EA | 0 to 1% (e.g., 1 ppm to 0.5%) | 10 ppm to 0.2% | 50 ppm to 0.1% |
| EtI | 0 to 1% (e.g., 1 ppm to 0.5%) | 10 ppm to 0.2% | 50 ppm to 0.1% |
| Li | 0 to 1% (e.g., 0.01 ppt to 0.1 ppm) | 0.1 ppt to 0.01 ppm | 1 ppt to 0.001 ppm |
| Rh | 0 to 1% (e.g., 0.01 ppt to 0.1 ppm) | 0.1 ppt to 0.01 ppm | 1 ppt to 0.001 ppm |

As the distillation column of the eighth distillation step or alkane separation step (14), there may be used a plate column, a packed column, or other columns.

Among the above-mentioned steps (10) to (14), the separation section (9) usually comprises at least the liquid-liquid separation step (10), the first aldehyde separation step or distillation step (11), the extraction step (12), and the first aldehyde separation step or distillation step (13).

(15) Off-Gas Treatment Section (or Step Group or Unit Group)

The off-gas produced from the process described above also contains useful components such as carbon monoxide and methyl iodide. Thus, preferably, the off-gas is treated in the off-gas treatment section (15) to give the useful components which are then collected. The off-gas treatment section (15) may comprise, for example, the steps of: (16) absorbing the off-gas to the absorption solvent at a high pressure (a high-pressure absorption step), (17) absorbing the off-gas to the absorption solvent at a low pressure (a low-pressure absorption step), and (18) diffusing a gaseous component absorbed in the absorption steps (16) and (17) (a diffusion step).

Examples of the absorption solvent to be used may include an acetic acid-based solvent and a methanol-based solvent. For example, the acetic acid-based solvent may have the following composition.

TABLE 50

|  | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppb to 0.1%) | 10 ppb to 0.01% | 100 ppb to 0.001% |
| CO | 0 to 1% (e.g., 1 ppb to 0.1%) | 10 ppb to 0.01% | 100 ppb to 0.001% |
| $CO_2$ | 0 to 1% (e.g., 1 ppb to 0.1%) | 10 ppb to 0.01% | 100 ppb to 0.001% |
| $CH_4$ | 0 to 1% (e.g., 1 ppb to 0.1%) | 10 ppb to 0.01% | 100 ppb to 0.001% |
| $N_2$ | 0 to 1% (e.g., 1 ppb to 0.1%) | 10 ppb to 0.01% | 100 ppb to 0.001% |
| AD | 0 to 1% (e.g., 1 ppb to 0.1%) | 10 ppb to 0.01% | 100 ppb to 0.001% |
| MeOH | 0 to 1% (e.g., 1 ppb to 0.1%) | 10 ppb to 0.01% | 100 ppb to 0.001% |
| MeI | 0 to 1% (e.g., 1 ppb to 0.1%) | 10 ppb to 0.01% | 100 ppb to 0.001% |
| MA | 0 to 1% (e.g., 1 ppb to 0.1%) | 10 ppb to 0.01% | 100 ppb to 0.001% |
| $H_2O$ | 10 ppm to 5% | 100 ppm to 2% | 0.1 to 1% |
| AcOH | 80 to 100% | 90 to 99.99% | 98 to 99.9% |
| HI | 0 to 1% (e.g., 0.1 ppb to 0.5%) | 1 ppb to 0.1% | 10 ppb to 100 ppm |
| FrOH | 0 to 1% (e.g., 1 to 300 ppm) | 5 to 100 ppm | 10 to 50 ppm |
| PrOH | 0 to 1% (e.g., 0.1 ppm to 0.1%) | 1 to 200 ppm | 10 to 100 ppm |
| DME | 0 to 1% (e.g., 1 ppb to 100 ppm) | 10 ppb to 10 ppm | 100 ppb to 5 ppm |
| AcA | 0 to 1% (e.g., 1 ppb to 0.1%) | 10 ppb to 100 ppm | 100 ppb to 50 ppm |
| $(CH_3)_2C=O$ | 0 to 1% (e.g., 1 ppb to 0.1%) | 10 ppb to 100 ppm | 100 ppb to 50 ppm |
| EtOH | 0 to 1% (e.g., 1 ppb to 0.1%) | 10 ppb to 100 ppm | 100 ppb to 50 ppm |
| EA | 0 to 1% (e.g., 1 ppb to 0.1%) | 10 ppb to 100 ppm | 100 ppb to 50 ppm |
| EtI | 0 to 1% (e.g., 1 ppb to 0.1%) | 10 ppb to 100 ppm | 100 ppb to 50 ppm |
| Li | 0 to 0.1% (e.g., 0.01 ppt to 100 ppb) | 1 ppt to 10 ppb | 10 ppt to 1 ppb |
| Rh | 0 to 0.1% (e.g., 0.01 ppt to 100 ppb) | 1 ppt to 10 ppb | 10 ppt to 1 ppb |

For example, the methanol-based solvent may have the following composition.

TABLE 51

|  | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppt to 0.1%) | 10 ppt to 0.01% | 100 ppt to 0.001% |
| CO | 0 to 1% (e.g., 1 ppt to 0.1%) | 10 ppt to 0.01% | 100 ppt to 0.001% |
| $CO_2$ | 0 to 1% (e.g., 1 ppt to 0.1%) | 10 ppt to 0.01% | 100 ppt to 0.001% |
| $CH_4$ | 0 to 1% (e.g., 1 ppt to 0.1%) | 10 ppt to 0.01% | 100 ppt to 0.001% |
| $N_2$ | 0 to 1% (e.g., 1 ppt to 0.1%) | 10 ppt to 0.01% | 100 ppt to 0.001% |
| AD | 0 to 1% (e.g., 1 ppb to 0.1%) | 10 ppb to 0.01% | 100 ppb to 0.001% |
| MeOH | 95 to 100% | 98 to 99.999% | 99 to 99.99% |
| MeI | 0 to 1% (e.g., 1 ppt to 0.1%) | 10 ppt to 0.01% | 100 ppt to 0.001% |
| MA | 0 to 1% (e.g., 1 ppb to 0.1%) | 10 ppb to 0.01% | 100 ppb to 0.001% |
| $H_2O$ | 0 to 1% (e.g., 1 ppm to 0.1%) | 10 ppm to 0.05% | 100 ppm to 0.01% |
| AcOH | 0 to 1% (e.g., 1 ppb to 0.1%) | 10 ppb to 0.01% | 100 ppb to 0.001% |
| HI | 0 to 1% (e.g., 0.1 ppb to 0.5%) | 1 ppb to 0.1% | 10 ppb to 100 ppm |
| FrOH | 0 to 1% (e.g., 1 to 300 ppm) | 5 to 100 ppm | 10 to 50 ppm |
| PrOH | 0 to 1% (e.g., 0.1 ppm to 0.1%) | 1 to 200 ppm | 10 to 100 ppm |
| DME | 0 to 1% (e.g., 1 ppb to 100 ppm) | 10 ppb to 10 ppm | 100 ppb to 5 ppm |
| AcA | 0 to 1% (e.g., 1 ppb to 0.1%) | 10 ppb to 100 ppm | 100 ppb to 50 ppm |
| $(CH_3)_2C=O$ | 0 to 1% (e.g., 1 ppb to 100 ppm) | 10 ppb to 50 ppm | 100 ppb to 30 ppm |
| EtOH | 0 to 1% (e.g., 1 ppb to 100 ppm) | 10 ppb to 50 ppm | 100 ppb to 10 ppm |

TABLE 51-continued

| | Range | Preferred range | More preferred range |
|---|---|---|---|
| EA | 0 to 1% (e.g., 1 ppb to 100 ppm) | 10 ppb to 50 ppm | 100 ppb to 10 ppm |
| EtI | 0 to 1% (e.g., 1 ppb to 100 ppm) | 10 ppb to 50 ppm | 100 ppb to 10 ppm |
| Li | 0 to 0.1% (e.g., 0.01 ppt to 100 ppb) | 1 ppt to 10 ppb | 10 ppt to 1 ppb |
| Rh | 0 to 0.1% (e.g., 0.01 ppt to 100 ppb) | 1 ppt to 10 ppb | 10 ppt to 1 ppb |
| Fe | 0 to 0.1% (e.g., 1 ppt to 1 ppm) | 10 ppt to 0.5 ppm | 100 ppt to 0.1 ppm |

Incidentally, methyl iodide MeI, methyl acetate MA, acetic acid AcOH, hydrogen iodide HI, formic acid FrOH, propionic acid PrOH, acetic anhydride AcA, lithium Li, and rhodium Rh are not usually detected from the methanol-based solvent.

(16) High-Pressure Absorption Step

In the off-gas treatment section (15), the noncondensable gas (the off-gas rich in carbon monoxide and methyl iodide) 11 from the reactor (1) is put into contact with an acetic acid 197 as an absorption solvent in the high-pressure absorption column (16) of the high-pressure absorption step or first absorption step (16), and the mixture is scrubbed to form an overhead stream 171 and a bottom or lower acetic acid stream 174; the overhead stream 171 is rich in carbon monoxide, and the bottom or lower acetic acid stream 174 is rich in methyl iodide, methyl acetate, and water. A portion 172 of the overhead stream (or gas stream) 171 is fed to the flasher (catalyst separation column) (2), and the residual portion 173 of the overhead stream 171 is fed to a boiler and used as a heat source for the process or is atmospherically discharged from a flare stack or a vent stack. The residual portion 173 of the overhead stream 171 may be incinerated or collected. The bottom or lower acetic acid stream 174 is fed to the diffusion column (18).

For example, the overhead stream 171 may have the following composition.

TABLE 52

| Average molecular weight 26.22 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 5% (e.g., 0.001 to 2.5%) | 0.01 to 2% | 0.1 to 1% |
| CO | 1 to 99% | 5 to 90% | 10 to 85% |
| $CO_2$ | 0 to 5% (e.g., 0.01 to 5%) | 0.1 to 3% | 0.2 to 2% |
| $CH_4$ | 0.01 to 15% | 0.1 to 10% | 1 to 6% |
| $N_2$ | 0.01 to 20% | 0.1 to 15% | 1 to 10% |
| AD | 0 to 1% (e.g., 0.001 to 1%) | 0.01 to 0.5% | 0.02 to 0.2% |
| MeOH | 0 to 1% (e.g., 1 ppm to 1%) | 5 ppm to 0.5% | 10 ppm to 0.1% |
| MeI | 0 to 90% (e.g., 1 to 90%) | 5 to 80% (e.g., 10 to 70%) | 20 to 50% |
| MA | 0 to 5% (e.g., 0.001 to 2%) | 0.01 to 1% | 0.05 to 0.5% |
| $H_2O$ | 0 to 1% (e.g., 1 ppm to 1%) | 5 ppm to 0.5% | 10 ppm to 0.1% |
| AcOH | 0 to 10% (e.g., 0.001 to 10%) | 0.01 to 5% | 0.1 to 2% |
| HI | 0 to 1% (e.g., 1 ppm to 1%) | 5 ppm to 0.5% | 10 ppm to 0.1% |
| FrOH | 0 to 1% (e.g., 0.1 ppm to 0.5%) | 1 ppm to 0.2% | 10 ppm to 0.1% |
| PrOH | 0 to 1% (e.g., 0.1 ppm to 0.5%) | 1 ppm to 0.2% | 10 ppm to 0.1% |
| DME | 0 to 1% (e.g., 0.1 ppm to 1%) | 1 ppm to 0.1% | 5 ppm to 0.05% |
| $(CH_3)_2C=O$ | 0 to 1% (e.g., 1 ppt to 0.1%) | 10 ppt to 100 ppm | 100 ppt to 10 ppm |
| EtOH | 0 to 1% (e.g., 1 ppt to 0.1%) | 10 ppt to 100 ppm | 100 ppt to 10 ppm |
| EA | 0 to 1% (e.g., 1 ppt to 0.1%) | 10 ppt to 100 ppm | 100 ppt to 10 ppm |
| EtI | 0 to 1% (e.g., 1 ppt to 0.1%) | 10 ppt to 100 ppm | 100 ppt to 10 ppm |
| Li | 0 to 0.1% (e.g., 1 ppt to 0.1%) | 10 ppt to 100 ppm | 100 ppt to 10 ppm |
| Rh | 0 to 0.1% (e.g., 1 ppt to 0.1%) | 10 ppt to 100 ppm | 100 ppt to 10 ppm |

For example, the bottom acetic acid stream 174 may have the following composition.

TABLE 53

| Average molecular weight 59.64 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |

TABLE 53-continued

| Average molecular weight 59.64 | Range | Preferred range | More preferred range |
|---|---|---|---|
| $H_2$ | 0 to 1% (e.g., 1 ppm to 1%) | 10 ppm to 0.5% | 50 ppm to 0.1% |
| CO | 0 to 5% (e.g., 1 ppm to 2%) | 10 ppm to 1% | 100 ppm to 0.5% |
| $CO_2$ | 0 to 1% (e.g., 1 ppm to 1%) | 10 ppm to 0.5% | 50 ppm to 0.1% |
| $CH_4$ | 0 to 1% (e.g., 1 ppm to 1%) | 10 ppm to 0.5% | 50 ppm to 0.1% |
| $N_2$ | 0 to 1% (e.g., 1 ppm to 1%) | 10 ppm to 0.5% | 50 ppm to 0.1% |
| AD | 0 to 1% (e.g., 0.1 ppm to 1%) | 1 ppm to 0.5% | 10 ppm to 0.1% |
| MeOH | 0 to 1% (e.g., 1 ppm to 1%) | 10 ppm to 0.5% | 50 ppm to 0.1% |
| MeI | 10 ppm to 10% | 100 ppm to 5% | 0.1 to 2% |
| MA | 10 ppm to 10% | 100 ppm to 5% | 0.1 to 2% |
| $H_2O$ | 10 ppm to 10% | 100 ppm to 5% | 0.1 to 2% |
| AcOH | 80 to 99.9% | 90 to 99.5% | 97 to 99% |
| HI | 0 to 1% (e.g., 0.1 ppb to 0.5%) | 1 ppb to 0.1% | 10 ppb to 100 ppm |
| FrOH | 0 to 1% (e.g., 1 ppm to 0.1%) | 5 to 200 ppm | 10 to 100 ppm |
| PrOH | 0 to 1% (e.g., 0.1 ppm to 0.1%) | 1 to 300 ppm | 10 to 100 ppm |
| DME | 0 to 1% (e.g., 1 ppb to 0.1%) | 10 ppb to 100 ppm | 100 ppb to 20 ppm |
| $(CH_3)_2C{=}O$ | 0 to 1% (e.g., 1 ppb to 0.1%) | 10 ppb to 100 ppm | 100 ppb to 50 ppm |
| EtOH | 0 to 1% (e.g., 1 ppb to 0.1%) | 10 ppb to 100 ppm | 100 ppb to 50 ppm |
| EA | 0 to 1% (e.g., 1 ppb to 0.1%) | 10 ppb to 100 ppm | 100 ppb to 50 ppm |
| EtI | 0 to 1% (e.g., 1 ppb to 0.1%) | 10 ppb to 100 ppm | 100 ppb to 50 ppm |
| Li | 0 to 0.1% (e.g., 0.1 ppt to 1000 ppb) | 1 ppt to 100 ppb | 10 ppt to 10 ppb |
| Rh | 0 to 0.1% (e.g., 0.1 ppt to 1000 ppb) | 1 ppt to 100 ppb | 10 ppt to 10 ppb |

(17) Low-Pressure Absorption Step

The noncondensable gas (the non-liquified gas in the decanter S2) 37, which is not condensed in the condenser of the first distillation step (3), and the noncondensable gas (the off-gas rich in acetic acid, methyl iodide, and methyl acetate) 30 from the flasher (catalyst separation column) (2) are mixed together to give a mixture (or mixed gas) 176. The mixture 176 is put into contact and scrub with an acetic acid 196 as an absorption solvent in the low-pressure absorption column (17) of the low-pressure absorption step or second absorption step (17), thus forming an overhead stream 181 and a bottom acetic acid stream 182; the overhead stream 181 is rich in carbon monoxide, carbon dioxide, and nitrogen, and the bottom acetic acid stream 182 is rich in acetic acid, methyl iodide, and methyl acetate. The overhead stream 181 is mixed with the overhead stream 171 from the high-pressure absorption column (16), and the resulting mixed gas 173 is fed to a boiler and is used as a heat source for the process. A portion 184 of the bottom acetic acid stream 182 is mixed with a portion of the bottom or lower acetic acid stream 174 from the high-pressure absorption column (16), and the resulting mixtures is fed to the flasher (catalyst separation column) (2). The residual portion 183 of the bottom or lower acetic acid stream 182 is mixed with the bottom acetic acid stream 175 from the high-pressure absorption column (16), and the resulting mixed acetic acid stream 185 is fed to the diffusion column (18).

For example, the mixture (or mixed gas) 176 may have the following composition.

TABLE 54

| Average molecular weight 41.94 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01 to 5% | 0.05 to 2% | 0.1 to 1% |
| CO | 1 to 99% | 5 to 80% | 10 to 70% |
| $CO_2$ | 0.1 to 20% | 0.5 to 15% | 1 to 15% |
| $CH_4$ | 0.1 to 20% | 0.5 to 15% | 1 to 10% |
| $N_2$ | 0.1 to 20% | 0.5 to 15% | 1 to 10% |
| AD | 0 to 10% (e.g., 0.001 to 7%) | 0.01 to 5% | 0.1 to 3% |
| MeOH | 0 to 1% (e.g., 1 ppm to 1%) | 5 ppm to 0.5% | 10 ppm to 0.1% |
| MeI | 1 to 95% | 10 to 90% | 20 to 80% |
| MA | 0.01 to 40% | 0.1 to 20% | 1 to 10% |
| $H_2O$ | 0 to 20% (e.g., 0.01 to 20%) | 0.02 to 10% | 0.05 to 1% |
| AcOH | 0 to 10% (e.g., 0.001 to 10%) | 0.01 to 1% | 0.03 to 0.5% |
| HI | 0 to 1% (e.g., 1 ppt to 0.1%) | 100 ppt to 0.01% | 10 ppb to 1 ppm |
| FrOH | 0 to 1% (e.g., 1 ppb to 0.1%) | 10 ppb to 100 ppm | 100 ppb to 10 ppm |
| PrOH | 0 to 1% (e.g., 1 ppb to 0.1%) | 10 ppb to 100 ppm | 100 ppb to 10 ppm |
| DME | 0 to 1% (e.g., 0.1 ppm to 1%) | 1 ppm to 0.1% | 5 ppm to 0.05% |
| $(CH_3)_2C{=}O$ | 0 to 1% (e.g., 0.01 ppb to 100 ppm) | 0.1 ppb to 10 ppm | 1 ppb to 1 ppm |
| EtOH | 0 to 1% (e.g., 0.01 ppb to 100 ppm) | 0.1 ppb to 10 ppm | 1 ppb to 1 ppm |
| EA | 0 to 1% (e.g., 0.01 ppb to 100 ppm) | 0.1 ppb to 10 ppm | 1 ppb to 1 ppm |
| EtI | 0 to 1% (e.g., 0.01 ppb to 100 ppm) | 0.1 ppb to 10 ppm | 1 ppb to 1 ppm |

TABLE 54-continued

| Average molecular weight 41.94 | Range | Preferred range | More preferred range |
|---|---|---|---|
| Li | 0 to 0.1% (e.g., 0.01 ppb to 100 ppm) | 0.1 ppb to 10 ppm | 1 ppb to 1 ppm |
| Rh | 0 to 0.1% (e.g., 0.01 ppb to 100 ppm) | 0.1 ppb to 10 ppm | 1 ppb to 1 ppm |

For example, the overhead stream (the line 181) may have the following composition.

TABLE 55

| Average molecular weight 26.57 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0.01 to 10% | 0.1 to 5% | 0.2 to 2% |
| CO | 10 to 90% | 20 to 80% | 40 to 75% |
| $CO_2$ | 0.1 to 40% | 1 to 30% | 5 to 20% |
| $CH_4$ | 0.1 to 20% | 0.5 to 15% | 1 to 10% |
| $N_2$ | 0.1 to 20% | 1 to 15% | 2 to 10% |
| AD | 0 to 1% (e.g., 0.1 ppm to 1%) | 1 ppm to 0.5% | 10 ppm to 0.1% |
| MeOH | 0 to 1% (e.g., 1 ppm to 1%) | 5 ppm to 0.5% | 10 ppm to 0.1% |
| MeI | 0 to 1% (e.g., 0.01 ppm to 1%) | 0.1 ppm to 0.1% | 1 to 100 ppm |
| MA | 0 to 5% (e.g., 0.001 to 5%) | 0.01 to 1% | 0.05 to 0.5% |
| $H_2O$ | 0 to 1% (e.g., 1 ppm to 1%) | 5 ppm to 0.5% | 10 ppm to 0.1% |
| AcOH | 0 to 30% (e.g., 0.001 to 30%) | 0.01 to 10% | 0.1 to 5% |
| HI | 0 to 1% (e.g., 1 ppb to 1%) | 10 ppb to 0.1% | 100 ppb to 0.01% |
| FrOH | 0 to 1% (e.g., 0.01 ppm to 0.5%) | 0.1 ppm to 0.1% | 10 ppm to 0.01% |
| PrOH | 0 to 1% (e.g., 1 ppb to 0.1%) | 10 ppb to 0.01% | 100 ppb to 0.001% |
| DME | 0 to 1% (e.g., 0.1 ppm to 1%) | 1 ppm to 0.1% | 5 ppm to 0.05% |
| $(CH_3)_2C=O$ | 0 to 1% (e.g., 1 ppt to 0.1%) | 10 ppt to 100 ppm | 100 ppt to 10 ppm |
| EtOH | 0 to 1% (e.g., 1 ppt to 0.1%) | 10 ppt to 100 ppm | 100 ppt to 10 ppm |
| EA | 0 to 1% (e.g., 1 ppt to 0.1%) | 10 ppt to 100 ppm | 100 ppt to 10 ppm |
| EtI | 0 to 1% (e.g., 1 ppt to 0.1%) | 10 ppt to 100 ppm | 100 ppt to 10 ppm |
| Li | 0 to 0.1% (e.g., 1 ppt to 0.1%) | 10 ppt to 100 ppm | 100 ppt to 10 ppm |
| Rh | 0 to 0.1% (e.g., 1 ppt to 0.1%) | 10 ppt to 100 ppm | 100 ppt to 10 ppm |

For example, the bottom acetic acid stream (the line 182) may have the following composition.

TABLE 56

| Average molecular weight 63.17 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppm to 1%) | 10 ppm to 0.5% | 50 ppm to 0.1% |
| CO | 0 to 2% (e.g., 1 ppm to 2%) | 10 ppm to 1% | 100 ppm to 0.5% |
| $CO_2$ | 0 to 5% (e.g., 1 ppm to 3%) | 10 ppm to 1% | 50 ppm to 0.5% |
| $CH_4$ | 0 to 1% (e.g., 1 ppm to 1%) | 10 ppm to 0.5% | 50 ppm to 0.1% |
| $N_2$ | 0 to 1% (e.g., 1 ppm to 1%) | 10 ppm to 0.5% | 50 ppm to 0.1% |
| AD | 0 to 5% (e.g., 1 ppm to 2%) | 10 ppm to 1% | 100 ppm to 0.5% |
| MeOH | 0 to 1% (e.g., 1 ppm to 1%) | 10 ppm to 0.5% | 50 ppm to 0.1% |
| MeI | 100 ppm to 30% | 0.1 to 20% | 1 to 15% |
| MA | 10 ppm to 10% | 100 ppm to 5% | 0.1 to 2% |
| $H_2O$ | 10 ppm to 10% | 100 ppm to 5% | 0.1 to 1% |
| AcOH | 70 to 99% | 80 to 98% | 85 to 95% |
| HI | 0 to 1% (e.g., 1 ppb to 0.5%) | 10 ppb to 0.1% | 100 ppb to 100 ppm |
| FrOH | 0 to 1% (e.g., 1 ppm to 0.1%) | 5 to 100 ppm | 10 to 50 ppm |
| PrOH | 0 to 1% (e.g., 0.1 ppm to 0.1%) | 1 to 300 ppm | 10 to 100 ppm |
| DME | 0 to 1% (e.g., 1 ppb to 0.1%) | 10 ppb to 100 ppm | 100 ppb to 20 ppm |
| $(CH_3)_2C=O$ | 0 to 1% (e.g., 1 ppb to 0.1%) | 10 ppb to 100 ppm | 100 ppb to 50 ppm |

TABLE 56-continued

| Average molecular weight 63.17 | Range | Preferred range | More preferred range |
|---|---|---|---|
| EtOH | 0 to 1% (e.g., 1 ppb to 0.1%) | 10 ppb to 100 ppm | 100 ppb to 50 ppm |
| EA | 0 to 1% (e.g., 1 ppb to 0.1%) | 10 ppb to 100 ppm | 100 ppb to 50 ppm |
| EtI | 0 to 1% (e.g., 1 ppb to 0.1%) | 10 ppb to 100 ppm | 100 ppb to 50 ppm |
| Li | 0 to 0.1% (e.g., 0.1 ppt to 1000 ppb) | 1 ppt to 100 ppb | 10 ppt to 10 ppb |
| Rh | 0 to 0.1% (e.g., 0.1 ppt to 1000 ppb) | 1 ppt to 100 ppb | 10 ppt to 10 ppb |

(18) Diffusion Step

In the diffusion column (stripping column) of the diffusion step (18), the mixed acetic acid stream 185 is distilled and stripped to form an overhead stream 191 and a bottom acetic acid stream 194; the overhead stream 191 is rich in methyl iodide and acetic acid (and also contains methyl acetate, acetaldehyde, or other compounds), and the bottom acetic acid stream 194 is rich in acetic acid, methyl acetate, and water. A first portion of the bottom acetic acid stream 194 is heated by a heating unit and is returned to a lower part of the diffusion column (18). A second portion (or residual portion) of the bottom acetic acid stream 194 is mixed with a portion 65 of the condensate (a portion of the condensate that is rich in acetic acid and is held in the hold tank T3) of the third overhead 61 from the third distillation column (6), forming a mixture 195. A portion 197 of the resulting mixture 195 is recycled to an upper part of the high-pressure absorption column (16), and the residual portion 196 of the mixture 195 is recycled to an upper part of the low-pressure absorption column (17).

The overhead stream 191 is cooled and condensed in a condenser to form a noncondensable gas 192 and a condensate 193. The noncondensable gas 192 (a stream being rich in methyl iodide and carbon monoxide and also containing carbon dioxide, methane, ethyl acetate, acetaldehyde, or other compounds) is mixed with the noncondensable gas from the decanter S2 of the liquid-liquid separation step (10), and the mixture is cooled and condensed in a condenser. The condensate (a stream being rich in methyl iodide, acetic acid, and methyl acetate and also containing water, acetaldehyde, or other compounds) 193 of the overhead stream 191 is fed to the hold tank T1 for holding the condensates 26, 28 of the volatile phase 24 from the flasher (catalyst separation column) (2). The condensate 193 is recycled to the reactor (1) via the hold tank T1. The condensate 193 may directly be recycled to the reactor (1).

For example, the mixed acetic acid stream 185 may have the following composition.

TABLE 57

| Average molecular weight 62.31 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppm to 1%) | 10 ppm to 0.5% | 50 ppm to 0.1% |
| CO | 0 to 2% (e.g., 1 ppm to 2%) | 10 ppm to 1% | 100 ppm to 0.5% |
| $CO_2$ | 0 to 2% (e.g., 1 ppm to 1%) | 10 ppm to 0.5% | 50 ppm to 0.2% |
| $CH_4$ | 0 to 1% (e.g., 1 ppm to 1%) | 10 ppm to 0.5% | 50 ppm to 0.1% |
| $N_2$ | 0 to 1% (e.g., 1 ppm to 1%) | 10 ppm to 0.5% | 50 ppm to 0.1% |
| AD | 0 to 2% (e.g., 1 ppm to 2%) | 10 ppm to 1% | 100 ppm to 0.5% |
| MeOH | 0 to 1% (e.g., 1 ppm to 1%) | 10 ppm to 0.5% | 50 ppm to 0.1% |
| MeI | 100 ppm to 30% | 0.1% to 20% | 1 to 15% |
| MA | 10 ppm to 10% | 100 ppm to 5% | 0.1 to 2% |
| $H_2O$ | 10 ppm to 10% | 100 ppm to 5% | 0.1 to 1% |
| AcOH | 70 to 99% | 80 to 98% | 85 to 95% |
| HI | 0 to 1% (e.g., 1 ppb to 0.5%) | 10 ppb to 0.1% | 100 ppb to 100 ppm |
| FrOH | 0 to 1% (e.g., 1 ppm to 0.1%) | 5 to 100 ppm | 10 to 50 ppm |
| PrOH | 0 to 1% (e.g., 0.1 ppm to 0.1%) | 1 to 300 ppm | 10 to 100 ppm |
| DME | 0 to 1% (e.g., 1 ppb to 0.1%) | 10 ppb to 100 ppm | 100 ppb to 50 ppm |
| $(CH_3)_2C=O$ | 0 to 1% (e.g., 1 ppb to 0.1%) | 10 ppb to 100 ppm | 100 ppb to 50 ppm |
| EtOH | 0 to 1% (e.g., 1 ppb to 0.1%) | 10 ppb to 100 ppm | 100 ppb to 50 ppm |
| EA | 0 to 1% (e.g., 1 ppb to 0.1%) | 10 ppb to 100 ppm | 100 ppb to 50 ppm |
| EtI | 0 to 1% (e.g., 1 ppb to 0.1%) | 10 ppb to 100 ppm | 100 ppb to 50 ppm |
| Li | 0 to 0.1% (e.g., 0.1 ppt to 1000 ppb) | 1 ppt to 100 ppb | 10 ppt to 10 ppb |
| Rh | 0 to 0.1% (e.g., 0.1 ppt to 1000 ppb) | 1 ppt to 100 ppb | 10 ppt to 10 ppb |

For example, the overhead stream 191 may have the following composition.

TABLE 58

| Average molecular weight 95.18 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 2% (e.g., 0.1 ppm to 2%) | 1 ppm to 1% | 10 ppm to 0.1% |
| CO | 0.001 to 10% | 0.01 to 5% | 0.1 to 2% |
| $CO_2$ | 0.001 to 10% | 0.01 to 5% | 0.1 to 2% |
| $CH_4$ | 0 to 5% (e.g., 1 ppm to 5%) | 10 ppm to 2% | 100 ppm to 1% |
| $N_2$ | 0 to 2% (e.g., 0.1 ppm to 2%) | 1 ppm to 1% | 10 ppm to 0.1% |
| AD | 10 ppm to 5% | 100 ppm to 2% | 0.1 to 1% |
| MeOH | 0 to 1% (e.g., 1 ppm to 1%) | 5 ppm to 0.5% | 10 ppm to 0.1% |
| MeI | 5 to 99% | 10 to 90% | 30 to 80% |
| MA | 0.01 to 30% | 0.1 to 20% | 1 to 10% |
| $H_2O$ | 0.001 to 10% | 0.01 to 5% | 0.1 to 2% |
| AcOH | 0.1 to 50% | 1 to 40% | 5 to 30% |
| HI | 0 to 1% (e.g., 1 ppb to 1%) | 10 ppb to 0.1% | 100 ppb to 0.01% |
| FrOH | 0 to 1% (e.g., 0.01 ppm to 0.5%) | 0.1 ppm to 0.1% | 1 ppm to 0.01% |
| PrOH | 0 to 1% (e.g., 0.01 ppm to 0.5%) | 0.1 ppm to 0.1% | 1 ppm to 0.01% |
| DME | 0 to 1% (e.g., 0.1 ppm to 1%) | 1 ppm to 0.1% | 5 ppm to 0.05% |
| $(CH_3)_2C=O$ | 0 to 1% (e.g., 1 ppt to 0.1%) | 10 ppt to 100 ppm | 100 ppt to 10 ppm |
| EtOH | 0 to 1% (e.g., 1 ppt to 0.1%) | 10 ppt to 100 ppm | 100 ppt to 10 ppm |
| EA | 0 to 1% (e.g., 1 ppt to 0.1%) | 10 ppt to 100 ppm | 100 ppt to 10 ppm |
| EtI | 0 to 1% (e.g., 1 ppt to 0.1%) | 10 ppt to 100 ppm | 100 ppt to 10 ppm |
| Li | 0 to 0.1% (e.g., 1 ppt to 0.1%) | 10 ppt to 100 ppm | 100 ppt to 10 ppm |
| Rh | 0 to 0.1% (e.g., 1 ppt to 0.1%) | 10 ppt to 100 ppm | 100 ppt to 10 ppm |

For example, the bottom acetic acid stream 194 may have the following composition.

TABLE 59

| Average molecular weight 59.59 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppb to 0.1%) | 10 ppb to 0.01% | 100 ppb to 0.001% |
| CO | 0 to 2% (e.g., 1 ppb to 1%) | 10 ppb to 0.5% | 100 ppb to 0.3% |
| $CO_2$ | 0 to 2% (e.g., 1 ppb to 1%) | 10 ppb to 0.5% | 100 ppb to 0.3% |
| $CH_4$ | 0 to 1% (e.g., 1 ppb to 0.1%) | 10 ppb to 0.01% | 100 ppb to 0.001% |
| $N_2$ | 0 to 1% (e.g., 1 ppb to 0.1%) | 10 ppb to 0.01% | 100 ppb to 0.001% |
| AD | 0 to 1% (e.g., 1 ppb to 0.1%) | 10 ppb to 0.01% | 100 ppb to 0.001% |
| MeOH | 0 to 1% (e.g., 1 ppb to 0.1%) | 10 ppb to 0.01% | 100 ppb to 0.001% |
| MeI | 0 to 1% (e.g., 1 ppb to 0.1%) | 10 ppb to 0.01% | 100 ppb to 0.001% |
| MA | 0 to 2% (e.g., 1 ppb to 1%) | 10 ppb to 0.5% | 100 ppb to 0.1% |
| $H_2O$ | 0 to 5% (e.g., 10 ppm to 5%) | 100 ppm to 2% | 0.1 to 1% |
| AcOH | 80 to 100% | 90 to 99.99% | 98 to 99.9% |
| HI | 0 to 1% (e.g., 0.1 ppb to 0.5%) | 1 ppb to 0.1% | 10 ppb to 100 ppm |
| FrOH | 0 to 1% (e.g., 1 to 100 ppm) | 5 to 1000 ppm | 10 to 300 ppm |
| PrOH | 0 to 1% (e.g., 0.1 ppm to 0.1%) | 1 to 1000 ppm | 10 to 200 ppm |
| DME | 0 to 1% (e.g., 1 ppb to 100 ppm) | 10 ppb to 10 ppm | 100 ppb to 5 ppm |
| $(CH_3)_2C=O$ | 0 to 1% (e.g., 1 ppb to 0.1%) | 10 ppb to 100 ppm | 100 ppb to 50 ppm |
| EtOH | 0 to 1% (e.g., 1 ppb to 0.1%) | 10 ppb to 100 ppm | 100 ppb to 50 ppm |
| EA | 0 to 1% (e.g., 1 ppb to 0.1%) | 10 ppb to 100 ppm | 100 ppb to 50 ppm |
| EtI | 0 to 1% (e.g., 1 ppb to 0.1%) | 10 ppb to 100 ppm | 100 ppb to 50 ppm |
| Li | 0 to 0.1% (e.g., 1 ppb to 0.1%) | 10 ppb to 100 ppm | 100 ppb to 50 ppm |
| Rh | 0 to 0.1% (e.g., 0.01 ppt to 100 ppb) | 1 ppt to 10 ppb | 10 ppt to 1 ppb |

For example, the composition of the portions 197, 196 of the mixture 195 may be substantially the same as the composition of the bottom acetic acid stream 194.

For example, the noncondensable gas 192 of the overhead stream 191 may have the following composition.

TABLE 60

| Average molecular weight 73.51 | Range | Preferred range | More preferred range |
|---|---|---|---|
| $O_2$ | 10% or less (e.g., 10 ppb to 10%), e.g., 10 ppb to 3.6% (e.g., 20 ppb to 2%), or less than 7% (e.g., 1 ppt to 5%), e.g., less than 3.6% (e.g., 0.1 ppb to 2%), e.g., 1 ppb to 1% (e.g., 10 ppb to 0.5%) | 30 ppb to 1% (e.g., 100 ppb to 0.1%), or 20 ppb to 0.3% | 500 ppb to 500 ppm (e.g., 1 to 100 ppm), or 50 ppb to 0.1% (e.g., 100 ppb to 200 ppm) |
| $H_2$ | 0 to 2% (e.g., 1 ppm to 2%) | 10 ppm to 1% | 100 ppm to 0.2% |
| CO | 0.1 to 90% | 1 to 60% | 5 to 30% |
| $CO_2$ | 0.1 to 90% | 1 to 60% | 5 to 30% |
| $CH_4$ | 0.01 to 20% | 0.1 to 10% | 0.5 to 5% |
| $N_2$ | 0.01 to 20% | 0.1 to 10% | 0.3 to 3% |
| AD | 100 ppm to 20% | 0.1 to 10% | 0.5 to 5% |
| MeOH | 0 to 1% (e.g., 1 ppm to 1%) | 5 ppm to 0.5% | 10 ppm to 0.1% |
| MeI | 1 to 95% | 10 to 90% | 40 to 80% |
| MA | 0.01 to 20% | 0.1 to 10% | 0.5 to 5% |
| $H_2O$ | 10 ppm to 5% | 100 ppm to 2% | 500 ppm to 1% |
| AcOH | 10 ppm to 10% | 100 ppm to 5% | 0.1 to 2% |
| HI | 0 to 1% (e.g., 1 ppb to 1%) | 10 ppb to 0.1% | 100 ppb to 0.01% |
| FrOH | 0 to 1% (e.g., 0.01 ppm to 0.5%) | 0.1 ppm to 0.1% | 1 ppm to 0.01% |
| PrOH | 0 to 1% (e.g., 1 ppb to 0.1%) | 10 ppb to 0.01% | 100 ppb to 0.001% |
| DME | 0 to 1% (e.g., 0.1 ppm to 1%) | 1 ppm to 0.1% | 5 ppm to 0.05% |
| $(CH_3)_2C=O$ | 0 to 1% (e.g., 1 ppb to 0.1%) | 10 ppb to 100 ppm | 100 ppt to 10 ppm |
| EtOH | 0 to 1% (e.g., 1 ppb to 0.1%) | 10 ppb to 100 ppm | 100 ppt to 10 ppm |
| EA | 0 to 1% (e.g., 1 ppb to 0.1%) | 10 ppb to 100 ppm | 100 ppt to 10 ppm |
| EtI | 0 to 1% (e.g., 1 ppb to 0.1%) | 10 ppb to 100 ppm | 100 ppt to 10 ppm |
| Li | 0 to 0.1% (e.g., 1 ppt to 1 ppm) | 10 ppt to 0.1 ppm | 100 ppt to 0.01 ppm |
| Rh | 0 to 0.1% (e.g., 1 ppt to 1 ppm) | 10 ppt to 0.1 ppm | 100 ppt to 0.01 ppm |

For example, the condensate 193 of the overhead stream 191 may have the following composition.

TABLE 61

| Average molecular weight 97.27 | Range | Preferred range | More preferred range |
|---|---|---|---|
| $O_2$ | 10% or less (e.g., 0.1 ppb to 10%), e.g., 0.2 ppb to 3.6% (e.g., 1 ppb to 2%) | less than 1% (e.g., 1 ppt to 1000 ppm), e.g., less than 700 ppm (e.g., 1 ppt to 500 ppm) | 10 ppt to 300 ppm, e.g., 100 ppt to 100 ppm |
| $H_2$ | 0 to 1% (e.g., 1 ppm to 1%) | 10 ppm to 0.5% | 50 ppm to 0.1% |
| CO | 0 to 2% (e.g., 1 ppm to 2%) | 10 ppm to 1% | 100 ppm to 0.5% |
| $CO_2$ | 0 to 3% (e.g., 1 ppm to 1%) | 10 ppm to 1% | 50 ppm to 0.5% |
| $CH_4$ | 0 to 1% (e.g., 1 ppm to 1%) | 10 ppm to 0.5% | 50 ppm to 0.1% |
| $N_2$ | 0 to 1% (e.g., 1 ppm to 1%) | 10 ppm to 0.5% | 50 ppm to 0.1% |
| AD | 0 to 3% (e.g., 1 ppm to 2%) | 10 ppm to 1.5% | 100 ppm to 1% |
| MeOH | 0 to 1% (e.g., 1 ppm to 1%) | 10 ppm to 0.5% | 50 ppm to 0.1% |
| MeI | 10 to 95% | 30 to 90% | 50 to 80% |
| MA | 0.1 to 30% | 1 to 20% | 3 to 10% |
| $H_2O$ | 0.001 to 10% | 0.01 to 5% | 0.1 to 2% |
| AcOH | 1 to 70% | 5 to 50% | 10 to 35% |
| HI | 0 to 1% (e.g., 1 ppb to 0.5%) | 10 ppb to 0.1% | 100 ppb to 100 ppm |
| FrOH | 0 to 1% (e.g., 0.01 ppm to 0.1%) | 0.1 to 100 ppm | 1 to 50 ppm |
| PrOH | 0 to 1% (e.g., 0.01 ppm to 0.1%) | 0.1 to 300 ppm | 1 to 100 ppm |
| DME | 0 to 1% (e.g., 1 ppb to 0.1%) | 10 ppb to 100 ppm | 100 ppb to 20 ppm |
| $(CH_3)_2C=O$ | 0 to 1% (e.g., 1 ppb to 0.1%) | 10 ppb to 100 ppm | 100 ppb to 50 ppm |
| EtOH | 0 to 1% (e.g., 1 ppb to 0.1%) | 10 ppb to 100 ppm | 100 ppb to 50 ppm |
| EA | 0 to 1% (e.g., 1 ppb to 0.1%) | 10 ppb to 100 ppm | 100 ppb to 50 ppm |
| EtI | 0 to 1% (e.g., 1 ppb to 0.1%) | 10 ppb to 100 ppm | 100 ppb to 50 ppm |
| Li | 0 to 0.1% (e.g., 0.1 ppt to 1000 ppb) | 1 ppt to 100 ppb | 10 ppt to 10 ppb |
| Rh | 0 to 0.1% (e.g., 0.1 ppt to 1000 ppb) | 1 ppt to 100 ppb | 10 ppt to 10 ppb |

The off-gas treatment section (15) usually comprises at least one absorption step selected from the high-pressure absorption step (16) and the low-pressure absorption step (17) among these steps (16) to (18).

EXAMPLES

The following examples are intended to describe this invention in further detail and should by no means be interpreted as defining the scope of the invention.

For corrosion tests, the following test pieces were used.
[Test piece]
Zr: zirconium, manufactured by ATI Japan
HB2: HASTELLOY B2 (nickel-based alloy), manufactured by Oda Koki Co., Ltd.
HC276: HASTELLOY C (nickel-based alloy), manufactured by Oda Koki Co., Ltd.
SUS316: Stainless steel, manufactured by Oda Koki Co., Ltd.
The following test items for corrosion were evaluated.
[Corrosion Rate of Test Piece]
The weight of each test piece after corrosion test was measured to determine a corrosion rate. Specifically, the decrease in weight of the test piece by corrosion was measured to determine a corrosion rate of the test piece per year, and the corrosion rate was converted into a decrease in thickness (mm) of the test piece per year (unit: "mm/Y"), thus evaluating the corrosion amount (corrosion rate).
[Presence of Partial Corrosion]
The presence of partial corrosion of each test piece was visually observed. Incidentally, the "partial corrosion" includes bead corrosion, pitting corrosion, and spot corrosion.
[Degree of Coloration]
The APHA (Hazen color number) of a mixture was measured according to Japanese Industrial Standards (JIS). A larger APHA value means a larger degree of coloration.
[Compositions (Component Ratios) of Liquid Phase and Gaseous Phase]
In the compositions (component ratios) shown in Comparative Examples and Examples and Tables, the concentrations of organic matters and water were measured by gas chromatography, and the concentration of lithium iodide (LiI) was measured by atomic absorption analysis. The concentration of hydrogen iodide (HI) was calculated by subtracting the concentration of an iodide ion derived from an iodide ion from the total iodide ion ($I^-$) concentration. The total amount of components in each of the liquid and the gaseous phases, including impurities and minor (or trace) components, is 100%. In this respect, the total of the components shown in Tables may be inconsistent with 100% in some cases due to analysis error and rounding up or down to significant figures (or predetermined digit number).

Incidentally, for each of noncondensable gaseous components (hydrogen, carbon monoxide, carbon dioxide, methane, nitrogen, oxygen) other than methyl iodide, when a component had a concentration of less than 1% by weight and less than 1% by volume, the concentration of the component was rounded off to two significant digits; when a component had a concentration of 1% by weight or more and 1% by volume or more, the concentration of the component was rounded off to the closest whole number.

Comparative Examples 1 to 14 and Examples 1 to 22

Comparative Example 1

In an autoclave (capacity: 500 ml) made of zirconium Zr, 39 g of MeI, 6.3 g of water, 0.003 g of HI, 8.4 g of MA, 207 g of acetic acid, 0.03 g of PA, and 46 g of LiI were charged, and a test piece (size: 36 mm×25=mm×2.5 mm) was set in the autoclave, and the autoclave was closed with a lid. Oxygen dissolved in the liquid in the autoclave was replaced by bubbling nitrogen gas $N_2$, and then 0.003 g of DME and 0.06 g of AD were fed to the autoclave. Increasing the pressure of the autoclave from the atmospheric pressure to 1 MPa with nitrogen gas $N_2$ and then releasing the pressure to the atmospheric pressure were performed three times; and increasing the pressure of the autoclave to 1 MPa with a mixed gas (93 vol % of CO, 7 vol % of $O_2$) and then releasing the pressure to the atmospheric pressure were performed three times; and a mixed gas (93 vol % of CO, 7 vol % of $O_2$) was injected until the pressure of the autoclave was 4 MPa. After injection of the mixed gas, the pressure was gradually released, and the oxygen concentration in the released gas was measured by an oxygen analyzer [a galvanic oxygen analyzer ("Model 1000RS" manufactured by TEKHNE Corporation)] to determine that the oxygen concentration reached 7 vol %. Thereafter, the pressure of the autoclave was released to 1 MPa, and then the autoclave was heated to 190° C. in an oil bath. The pressure after the heating was maintained to 2.8 MPa. After 100 hours under the steady condition, the autoclave was cooled to a room temperature, and the reaction mixture was sampled from a nozzle of the autoclave. The sample was subjected to composition analysis to determine a degree of coloration (APHA). Moreover, the atmosphere in the autoclave was replaced with $N_2$, and the autoclave was opened. The test piece was taken out and weighed to determine a corrosion rate.

The concentration of oxygen in the gaseous phase was 7 vol %. The concentration of oxygen dissolved in the liquid phase under a total pressure of 1 MPa was calculated to be $7.0 \times 10^{-5}$ g/g by Aspen Plus (manufactured by Aspen Technology, Inc.).

Comparative Examples 2 to 11

A corrosion test was performed in the same manner as in Comparative Example 1 except that the feed composition, the pressure, and the heating temperature were changed.

Comparative Example 12

A corrosion test was performed in the same manner as in Comparative Example 1 except that the feed composition, the feed gas composition (93 vol % of $N_2$, 7 vol % of $O_2$), the pressure, and the heating temperature were changed.

Comparative Example 13

In the process for continuously producing acetic acid as shown in FIG. 1, methanol was allowed to react with carbon monoxide (carbon monoxide having a concentration of oxygen of 10% by weight (9 vol %)) in a carbonylation reactor, the reaction mixture was continuously fed, for flash evaporation, from the reactor to a flasher to form a less-volatile phase (a bottom fraction at least containing a rhodium catalyst, lithium iodide, acetic acid, methyl acetate, methyl iodide, water, and hydrogen iodide) and a volatile phase (liquid temperature of liquefied gaseous fraction: 140° C.), and the volatile phase was fed to a first distillation column.

The volatile phase contained 26.8% by weight of methyl iodide (MeI), 4.5% by weight of methyl acetate (MA), 2.0% by weight of water ($H_2O$), 500 ppm by weight of hydrogen iodide (HI), 600 ppm by weight of acetaldehyde (AD), 62.8% by weight of acetic acid, 0.0070% by weight (70 ppm by weight) of hydrogen, 2% by weight of carbon monoxide, 0.060% by weight (600 ppm by weight) of carbon dioxide, 0.070% by weight (700 ppm by weight) of methane, 0.070% by weight (700 ppm by weight) of nitrogen, and oxygen and other minor components (total: 100% by weight).

In a case where acetic acid vapor and/or liquid enters a pressure sensor of a differential pressure type level gauge for measuring a liquid level of the bottom liquid of the first distillation column, the level gauge may be operated improperly. In order to prevent such a trouble, 9 parts by weight of purge air relative to 100 parts by weight of the volatile phase fed to the first distillation column was supplied to the gaseous phase side of the differential pressure type level gauge.

The volatile phase (100 parts by weight) was fed to the first distillation column (actual number of plates: 20 plates, feed plate: the 2nd plate from the bottom) and was distilled under conditions of at a gauge pressure of 150 kPa, a column bottom temperature of 143° C., a column top temperature of 115° C., and a light-phase reflux ratio of 12. The resulting overhead was cooled in a condenser to form a condensate and a noncondensable gas. The condensate (temperature: 40° C.) was liquid-liquid (or biphasically) separated in a decanter to form an aqueous phase (light phase) and an organic phase (heavy phase), and 1.3 parts by weight of the aqueous phase and 30 parts by weight of the organic phase were recycled to the reactor. From the condenser, 13 parts by weight of the noncondensable gas (off-gas stream) was withdrawn.

The overhead (column top) composition from the first distillation column (the composition of the overhead) was as follows: 43.2% by weight of methyl iodide (MeI), 7.5% by weight of methyl acetate (MA), 21.1% by weight of water ($H_2O$), 100 ppm by weight of hydrogen iodide (HI), 5.9% by weight of acetic acid, 0.010% by weight (100 ppm by weight) of hydrogen, 4% by weight of carbon monoxide, 0.10% by weight (1000 ppm by weight) of carbon dioxide, 0.11% by weight (1100 ppm by weight) of methane, 12% by weight of nitrogen, 6% by weight (7 vol %) of oxygen, and other minor components (total: 100% by weight); and the composition of the noncondensable gas (off-gas stream) from the condenser was as follows: 3.6% by weight of methyl iodide (MeI), 0.2% by weight of methyl acetate (MA), 200 ppm by weight of water ($H_2O$), hydrogen iodide (HI) (not measured), 200 ppm by weight of acetic acid, 0.040% by weight (400 ppm by weight) of hydrogen, 17% by weight of carbon monoxide, 0.50% by weight of carbon dioxide, 0.50% by weight of methane, 53% by weight of nitrogen, 25% by weight (23 vol %) of oxygen, and other minor components (total: 100% by weight). The composition of the aqueous phase (light phase) from the condenser was as follows: 3.3% by weight of methyl iodide (MeI), 6.6% by weight of methyl acetate (MA), 73.0% by weight of water ($H_2O$), 100 ppm by weight of hydrogen iodide (HI), 17.0% by weight of acetic acid, 0.0080% by weight (80 ppm by weight) of oxygen, and other minor components (total: 100% by weight); and the composition of the organic phase (heavy phase) was as follows: 86% by weight of methyl iodide (MeI), 11.1% by weight of methyl acetate (MA), 0.5% by weight of water ($H_2O$), 100 ppm by weight of hydrogen iodide (HI), 2.0% by weight of acetic acid, 0.0090% by weight (90 ppm by weight) of oxygen, and other minor components (total: 100% by weight).

A side-cut stream (62.8 parts by weight) of the first distillation column was fed to a second distillation column for dehydration and purification. The composition of the above side-cut stream was as follows: 2.4% by weight of methyl iodide (MeI), 1.6% by weight of methyl acetate (MA), 1.3% by weight of water ($H_2O$), 45 ppm by weight of hydrogen iodide (HI), 94.6% by weight of acetic acid, 0.0090% by weight (90 ppm by weight) of oxygen, and other minor components (total: 100% by weight). The remainder of the feed (volatile phase) was recycled as a bottom stream to the reaction system. The term "parts by weight" of a fluid (e.g., a volatile phase, an aqueous phase (light phase) and an organic phase (heavy phase), an off-gas stream, a side-cut stream, and a bottom stream) indicates a flow rate per unit hour (per hour) (the same applies hereinafter).

In such a continuous reaction process, the above-mentioned test pieces were placed on the feed plate of the first distillation column (the 2nd plate from the bottom, temperature: 140° C.) and the upper part of the column (the 19th plate from the bottom). After the process was operated for 500 hours, each test piece was examined for a corrosion test. The weight of each test piece before and after the corrosion test was measured to determine a corrosion amount.

Moreover, the crude acetic acid (side-cut stream) from the first distillation column was examined for the APHA.

Comparative Example 14

In the process for continuously producing acetic acid as shown in FIG. 1, methanol was allowed to react with carbon monoxide (concentration of oxygen: 10 ppm by weight) in a carbonylation reactor. In the same manner as in Comparative Example 13, a volatile phase from a flasher was distilled in a first distillation column, and 100 parts by weight of a side-cut stream of the first distillation column was fed to a second distillation column for dehydration and purification. In a case where acetic acid vapor and/or liquid enters a pressure sensor of a differential pressure type level gauge for measuring a liquid level of the bottom liquid of the second distillation column, the level gauge may be operated improperly. In order to prevent such a trouble, 11 parts by weight of purge air relative to 100 parts by weight of the side-cut stream fed was supplied to the gaseous phase side of the differential pressure type level gauge.

In the second distillation column (actual number of plates: 50 plates, distance or place spacing between a feed plate and a plate from which a column-top vapor is withdrawn: 15 plates as actual plates), distillation was carried out at a column top gauge pressure of 200 kPa, a column bottom temperature of 161° C., a column top temperature of 150° C., and a reflux ratio of 0.5 (reflux amount/distillate amount).

From the top of the second distillation column, 60 parts by weight of an overhead was withdrawn. The overhead had a composition containing 6.3% by weight of methyl iodide (MeI), 4.1% by weight of methyl acetate (MA), 3.3% by weight of water ($H_2O$), 10 ppm by weight of hydrogen iodide (HI), 0 ppm by weight of hydrogen, 0.00010% by weight (1.0 ppm by weight) of carbon monoxide, 0 ppm by weight of carbon dioxide, 0 ppm by weight of methane, 14% by weight of nitrogen, 4% by weight (7 vol %) of oxygen, and other minor components, and the remainder was acetic acid.

The overhead from the second distillation column was cooled in a condenser, and the resulting condensate was held in a reflux tank. A portion (32 parts by weight) of the condensate in the tank was withdrawn and was recycled to the reaction system. A portion (16 parts by weight) of the condensate was returned to the second distillation column for reflux at a reflux ratio of 0.5 as mentioned above. The condensate had a composition containing 7.7% by weight of methyl iodide (MeI), 5.0% by weight of methyl acetate (MA), 4.1% by weight of water ($H_2O$), 9 ppm by weight of hydrogen iodide (HI), 0.0070% by weight (70 ppm by weight) of oxygen, and other minor components, and the remainder was acetic acid. From the condenser, 11 parts by weight of a noncondensable gas was withdrawn. The noncondensable gas had a composition having 22% by weight (20 vol %) of oxygen and 78% by weight (70 vol %) of nitrogen, and negligible amounts of other components.

A crude acetic acid obtained by the dehydration and purification was withdrawn as a bottom stream from the second distillation column. The bottom stream (crude acetic acid) has a composition containing 6 ppb by weight of methyl iodide (MeI), 0.05% by weight of water ($H_2O$), 4 ppb by weight of hydrogen iodide (HI), 6 ppm by weight of methyl acetate (MA), and other minor components (containing oxygen), and the remainder was acetic acid. The term "parts by weight" of a fluid (e.g., a feed liquid, an overhead (distillate), an off-gas stream, and a bottom stream) indicates a flow rate per unit hour (per hour) (the same applies hereinafter).

In such a continuous reaction process, the above-mentioned test pieces were placed on the 2nd plate from the bottom (a plate above an air purge line) of the second distillation column and the column top (the 50th plate from the bottom) of the second distillation column and were left for 500 hours, and each test piece was examined for a corrosion test. The weight of each test piece before and after the corrosion test was measured to determine a corrosion amount.

Moreover, the feed liquid to the second distillation column (the side-cut stream from the first distillation column) and the bottom stream (crude acetic acid) from the second distillation column were examined for the APHA.

Examples 1 to 10

A corrosion test was performed in the same manner as in Comparative Example 1 except that the feed composition, the feed gas composition (a mixed gas containing oxygen $O_2$ at a concentration of 0.010 vol % and carbon monoxide CO as the remainder), the pressure, and the heating temperature were changed.

Example 11

A corrosion test was performed in the same manner as in Comparative Example 1 except that the feed composition, the feed gas composition (95 vol % of CO, 5 vol % of $O_2$), the pressure, and the heating temperature were changed. The concentration of oxygen in the gaseous phase was 1 vol %. The concentration of oxygen dissolved in the liquid phase under a total pressure of 140 kPa was calculated to be $4.0 \times 10^{-6}$ g/g by Aspen Plus (manufactured by Aspen Technology, Inc.).

Example 12

A corrosion test was performed in the same manner as in Comparative Example 1 except that the feed composition, the feed gas composition (99 vol % of CO, 1 vol % of $O_2$), the pressure, and the heating temperature were changed.

Example 13

A corrosion test was performed in the same manner as in Comparative Example 1 except that the feed composition, the feed gas composition (a mixed gas containing oxygen $O_2$ at a concentration of 0.00010 vol % (1.0 vol ppm) and carbon monoxide CO as the remainder), the pressure, and the heating temperature were changed. Provided that, until the concentration of oxygen in a released gas was 1.0 vol ppm, a pressurization to 1 MPaG with a mixed gas (a mixed gas containing oxygen $O_2$ at a concentration of 0.00010 vol % and carbon monoxide CO as the remainder) and a pressure release to the atmospheric pressure were repeated four times. That is, as a result, the pressurization to 1 MPaG and the pressure release to the atmospheric pressure were repeated seven times in total, and thereafter, the pressure was increased to 4 MPa and was then released. The oxygen concentration in the released gas was measured by an oxygen analyzer to determine that the oxygen concentration reached 1.0 vol ppm. Then, the corrosion test was performed in the same manner as in Comparative Example 1.

Example 14

A corrosion test was performed in the same manner as in Comparative Example 1 except that the feed composition, the feed gas composition (a mixed gas containing oxygen $O_2$ at a concentration of 0.10 vol % and nitrogen $N_2$ as the remainder), the pressure, and the heating temperature were changed.

Example 15

A corrosion test was performed in the same manner as in Comparative Example 1 except that the feed composition, the feed gas composition (a mixed gas containing oxygen $O_2$ at a concentration of 0.010 vol % and nitrogen $N_2$ as the remainder), the pressure, and the heating temperature were changed.

Example 16

A corrosion test was performed in the same manner as in Comparative Example 1 except that the feed composition, the feed gas composition (a mixed gas containing oxygen $O_2$ at a concentration of 0.0010 vol % and nitrogen $N_2$ as the remainder), the pressure, and the heating temperature were changed. Provided that, until the concentration of oxygen in a released gas was 0.0010 vol %, a pressurization to 1 MPaG with a mixed gas (a mixed gas containing oxygen $O_2$ at a concentration of 0.0010 vol % and $N_2$ as the remainder) and a pressure release to the atmospheric pressure were repeated three times. That is, as a result, the pressure release to the atmospheric pressure and the pressurization to 1 MPaG were repeated six times in total, and thereafter, the pressure was increased to 4 MPa and was then released. The oxygen concentration in the released gas was measured by an oxygen analyzer to determine that the oxygen concentration reached 0.0010 vol %. Then, the corrosion test was performed in the same manner as in Comparative Example 1.

Example 17

A corrosion test was performed in the same manner as in Comparative Example 1 except that the feed composition, the feed gas composition (a mixed gas containing 2 vol % of $H_2$, 15 vol % of $CO_2$, 7 vol % of $CH_4$, 8 vol % of $N_2$, 0.010 vol % of $O_2$, and carbon monoxide CO as the remainder), the pressure, and the heating temperature were changed.

Example 18

A corrosion test was performed in the same manner as in Comparative Example 1 except that the feed composition, the feed gas composition (a mixed gas containing oxygen $O_2$ at a concentration of 0.00010 vol % (1.0 vol ppm) and carbon monoxide CO as the remainder), the pressure, and the heating temperature were changed. Provided that, until the concentration of oxygen in a released gas was 1.0 vol ppm, a pressurization to 1 MPaG with a mixed gas (a mixed gas containing oxygen $O_2$ at a concentration of 0.00010 vol % and carbon monoxide CO as the remainder) and a pressure release to the atmospheric pressure were repeated four times. That is, as a result, the pressure release to the atmospheric pressure and the pressurization to 1 MPaG were repeated seven times in total, and thereafter, the pressure was increased to 4 MPa and was then released. The oxygen concentration in the released gas was measured by an oxygen analyzer to determine that the oxygen concentration reached 1.0 vol ppm. Then, the corrosion test was performed in the same manner as in Comparative Example 1.

Example 19

A corrosion test was performed in the same manner as in Comparative Example 1 except that the feed composition, the feed gas composition (a mixed gas containing oxygen $O_2$ at a concentration of 0.000010 vol % (0.10 vol ppm) and carbon monoxide CO as the remainder), the pressure, and the heating temperature were changed. Provided that, until the concentration of oxygen in a released gas was 0.10 vol ppm, a pressurization to 1 MPaG with a mixed gas (a mixed gas containing oxygen $O_2$ at a concentration of 0.000010 vol % and carbon monoxide CO as the remainder) and a pressure release to the atmospheric pressure were repeated four times. That is, as a result, the pressure release to the atmospheric pressure and the pressurization to 1 MPaG were repeated seven times in total, and thereafter, the pressure was increased to 4 MPa and was then released. The oxygen concentration in the released gas was measured by an oxygen analyzer to determine that the oxygen concentration reached 0.10 vol ppm. Then, the corrosion test was performed in the same manner as in Comparative Example 1.

Example 20

A corrosion test was performed in the same manner as in Comparative Example 13 except that the concentration of oxygen in the volatile phase from the flasher was changed from 3% by weight to 0.1% by weight by regulating the concentration of oxygen in carbon monoxide fed to the carbonylation reactor. By reducing the concentration of oxygen in carbon monoxide, the composition of the volatile phase fed to the first distillation column was changed. The volatile phase contained 27.6% by weight of methyl iodide (MeI), 4.6% by weight of methyl acetate (MA), 2.0% by weight of water ($H_2O$), 450 ppm by weight of hydrogen iodide (HI), 64.6% by weight of acetic acid, 0.0070% by weight (70 ppm by weight) of hydrogen, 0.60% by weight (6000 ppm by weight) of carbon monoxide, 0.070% by weight (700 ppm by weight) of carbon dioxide, 0.070% by weight (700 ppm by weight) of methane, 0.070% by weight (700 ppm by weight) of nitrogen, 0.30% by weight (0.60 vol %) of oxygen, and other minor components (total: 100% by weight). Moreover, the overhead (column top) composition from the first distillation column (the composition of the overhead) was as follows: 54.2% by weight of methyl iodide (MeI), 9.4% by weight of methyl acetate (MA), 26.5% by weight of water ($H_2O$), 100 ppm by weight of hydrogen iodide (HI), 7.3% by weight of acetic acid, 0.010% by weight (100 ppm by weight) of hydrogen, 1% by weight of carbon monoxide, 0.14% by weight (1400 ppm by weight) of carbon dioxide, 0.15% by weight (1500 ppm by weight) of methane, 0.15% by weight (1500 ppm by weight) of nitrogen, 0.20% by weight (2000 ppm by weight) (0.30 vol %) of oxygen, and other minor components (total: 100% by weight). From the condenser for cooling the column top overhead, 1.4 parts by weight of a noncondensable gas (off-gas stream) was withdrawn. The composition of the noncondensable gas was as follows: 35% by weight of methyl iodide (MeI), 2.0% by weight of methyl acetate (MA), 1000 ppm by weight of water ($H_2O$), hydrogen iodide (HI) (not measured), 700 ppm by weight of acetic acid, 0.50% by weight (5000 ppm by weight) of hydrogen, 41% by weight of carbon monoxide, 5% by weight of carbon dioxide, 5% by weight of methane, 5% by weight of nitrogen, 6% by weight (6 vol %) of oxygen, and other minor components (total: 100% by weight). The condensate of the overhead was liquid-liquid separated in a decanter to form an aqueous phase (light phase) and an organic phase (heavy phase), and 1.4 parts by weight of the aqueous phase and 30 parts by weight of the organic phase were recycled to the reactor. The bottom stream (3 parts by weight) from the first distillation column was recycled to the reactor, and the remainder of the feed (volatile phase) was withdrawn as a side-cut stream from the first distillation column. The compositions of these process streams (the aqueous phase, the organic phase, and the side-cut stream) were substantially the same as those in Comparative Example 13.

Example 21

A corrosion test was performed in the same manner as in Comparative Example 14 except that 1 part by weight of purge nitrogen containing 6% by weight of oxygen relative to 100 parts by weight of the feed amount of the side-cut stream of the first distillation column was supplied to the gaseous phase side of the differential pressure type level gauge for measuring a liquid level of the bottom liquid of the second distillation column.

From the top of the second distillation column, 50 parts by weight of an overhead was withdrawn. The overhead had a composition containing 7.5% by weight of methyl iodide (MeI), 4.9% by weight of methyl acetate (MA), 4.0% by weight of water ($H_2O$), 10 ppm by weight of hydrogen iodide (HI), 0 ppm by weight of hydrogen, 0.00010% by weight (1.0 ppm by weight) of carbon monoxide, 0 ppm by weight of carbon dioxide, 0 ppm by weight of methane, 2% by weight of nitrogen, 0.40% by weight (0.90 vol %) of oxygen, and other minor components, and the remainder was acetic acid.

The overhead from the second distillation column was cooled in a condenser, and the resulting condensate was held in a reflux tank. A portion (32 parts by weight) of the condensate in the tank was withdrawn and was recycled to the reaction system. A portion (16 parts by weight) of the condensate was returned to the second distillation column for reflux at a reflux ratio of 0.5. The condensate had a composition containing 7.7% by weight of methyl iodide (MeI), 5.0% by weight of methyl acetate (MA), 4.1% by weight of water ($H_2O$), 9 ppm by weight of hydrogen iodide (HI), 0.00020% by weight (2.0 ppm by weight) of oxygen, and other minor components, and the remainder was acetic acid. From the condenser, 1 part by weight of a noncondensable gas was withdrawn. The noncondensable gas had a composition having 7% by weight (6 vol %) of oxygen and 93% by weight (94 vol %) of nitrogen, and the negligible amounts of other components. A bottom stream (crude acetic acid) from the second distillation column had a composition containing 4 ppb by weight of methyl iodide (MeI), 0.05% by weight of water (H$_2$O), 5 ppb by weight of hydrogen iodide (HI), 5 ppm by weight of methyl acetate (MA), and other minor components (containing oxygen), and the remainder was acetic acid.

Example 22

In the process for continuously producing acetic acid as shown in FIG. 1, methanol was allowed to react with carbon monoxide (carbon monoxide having a concentration of oxygen of 2% by weight (2 vol %)) in a carbonylation reactor, the reaction mixture was continuously fed from the reactor to a flasher for flash evaporation to form a less-volatile phase (a bottom fraction at least containing a rhodium catalyst, lithium iodide, acetic acid, methyl acetate, methyl iodide, water, and hydrogen iodide) and a volatile phase (liquid temperature of liquefied gaseous fraction: 140° C.). The volatile phase contained 27.1% by weight of methyl iodide (MeI), 4.5% by weight of methyl acetate (MA), 2.0% by weight of water (H$_2$O), 500 ppm by weight of hydrogen iodide (HI), 63.5% by weight of acetic acid, 0.0070% by weight (70 ppm by weight) of hydrogen, 2% by weight of carbon monoxide, 0.060% by weight (600 ppm by weight) of carbon dioxide, 0.070% by weight (700 ppm by weight) of methane, 0.070% by weight (700 ppm by weight) of nitrogen, 0.30% by weight (0.70 vol %) of oxygen, and other minor components (total: 100% by weight).

The volatile phase (100 parts by weight) was fed to the first distillation column (actual number of plates: 20, feed plate: the 2nd plate from the bottom) and was distilled at a gauge pressure of 150 kPa, a column bottom temperature of 143° C., a column top temperature of 115° C., and a light-phase reflux ratio of 12. The resulting overhead from the column was cooled in a condenser to form a condensate and a noncondensable gas. The condensate (temperature: 40° C.) was liquid-liquid separated in a decanter to form an aqueous phase (light phase) and an organic phase (heavy phase), and 1.3 parts by weight of the aqueous phase (light phase) and 30 parts by weight of the organic phase (heavy phase) were recycled to the reactor. From the condenser, 4.1 parts by weight of the noncondensable gas (off-gas stream) was withdrawn. The overhead (column top) composition from the first distillation column (the composition of the overhead) was as follows: 52.4% by weight of methyl iodide (MeI), 9.1% by weight of methyl acetate (MA), 25.6% by weight of water (H$_2$O), 100 ppm by weight of hydrogen iodide (HI), 7.1% by weight of acetic acid, 0.010% by weight (100 ppm by weight) of hydrogen, 5% by weight of carbon monoxide, 0.12% by weight (1200 ppm by weight) of carbon dioxide, 0.14% by weight (1400 ppm by weight) of methane, 0.14% by weight (1400 ppm by weight) of nitrogen, 0.50% by weight (0.70 vol %) of oxygen, and other minor components (total: 100% by weight); and the composition of the noncondensable gas (off-gas stream) from the condenser was as follows: 15% by weight of methyl iodide (MeI), 1% by weight of methyl acetate (MA), 200 ppm by weight of water (H$_2$O), hydrogen iodide (HI) (not measured), 200 ppm by weight of acetic acid, 0.20% by weight (2000 ppm by weight) of hydrogen, 71% by weight of carbon monoxide, 2% by weight of carbon dioxide, 2% by weight of methane, 2% by weight of nitrogen, 6% by weight (6 vol %) of oxygen, and other minor components (total: 100% by weight). The composition of the aqueous phase (light phase) was as follows: 3.3% by weight of methyl iodide (MeI), 6.6% by weight of methyl acetate (MA), 73.0% by weight of water (H$_2$O), 100 ppm by weight of hydrogen iodide (HI), 17.0% by weight of acetic acid, 0.0014% by weight (14 ppm by weight) of oxygen, and other minor components (total: 100% by weight); and the composition of the organic phase (heavy phase) was as follows: 86% by weight of methyl iodide (MeI), 11.4% by weight of methyl acetate (MA), 0.6% by weight of water (H$_2$O), 100 ppm by weight of hydrogen iodide (HI), 1.9% by weight of acetic acid, 0.0016% by weight (16 ppm by weight) of oxygen, and other minor components (total: 100% by weight).

A side-cut stream (62.8 parts by weight) of the first distillation column was fed to a second distillation column for dehydration and purification. The composition of the above side-cut stream was as follows: 2.4% by weight of methyl iodide (MeI), 1.6% by weight of methyl acetate (MA), 1.3% by weight of water (H$_2$O), 48 ppm by weight of hydrogen iodide (HI), 94.6% by weight of acetic acid, 0.0010% by weight (10 ppm by weight) of oxygen, and other minor components (total: 100% by weight). The remainder of the feed (volatile phase) was recycled as a bottom stream to the reaction system.

In such a continuous reaction process, the above-mentioned test pieces were placed on the feed plate of the first distillation column (the 2nd plate from the bottom, temperature: 140° C.) and the upper part of the column (the 19th plate from the bottom). After the process was operated for 500 hours, each test piece was examined for a corrosion test. The weight of each test piece before and after the corrosion test was measured to determine a corrosion amount.

Moreover, the crude acetic acid (side-cut stream) from the first distillation column was examined for the APHA.

Tables 62 to 66 show the compositions (component ratios) and the results of the corrosion test. Incidentally, Table 62 shows the compositions of the liquid phases in Comparative Examples 1 to 12, Table 63 shows the compositions of the liquid phases in Examples 1 to 19, Table 64 shows the compositions of the gaseous phases in Comparative Examples 1 to 12 and Examples 1 to 19, and Table 65 and Table 66 show the results of the corrosion test. In Table 62 to Table 64, "wt %" represents % by weight, "vol %" denotes % by volume, "MeI" represents methyl iodide, "HI" denotes hydrogen iodide, "MA" represents methyl acetate, "MeOH" denotes methanol, "Ac" represents acetic acid, "AD" denotes acetaldehyde, "PA" represents propionic acid, and "LiI" denotes lithium iodide.

In Comparative Examples and Examples conducted under a concentration of oxygen of 1 to 7 vol % in a gaseous phase, the oxygen concentration after the corrosion test was reduced by about 0 to 2 vol %. In examples conducted under a concentration of oxygen of less than 1% in a gaseous phase, the oxygen concentration after the corrosion test was reduced by about 2 to 10 vol %.

Since it is difficult to measure the concentration of DME, which has a low boiling point, the concentration of DME was determined to be the calculation concentration of DME fed.

In replacing oxygen in the liquid with nitrogen gas by nitrogen gas bubbling after feeding of the liquid, a portion of components in the mixture was discharged to the outside of the system in accompanying with nitrogen gaseous phase. Thus, there is a difference, particularly in a concentration of methyl iodide, between the feed composition and the composition after the experiment.

Incidentally, for all Comparative Examples and Examples except for Comparative Examples 8, 9 and Examples 8, 9, a peak originated from DME in the liquid was observed by gas chromatography after finishing of the experiment. The concentration of DME calculated from the percentage of area was about 10 to 1000 ppm by weight.

TABLE 62

| | MeI wt % | Water wt % | HI wt % | MA wt % | MeOH wt % | DME wt % | Ac wt % | AD wt % | PA wt % | LiI wt % | Temperature ° C. | Pressure KPG |
|---|---|---|---|---|---|---|---|---|---|---|---|---|
| Com. Ex. 1 | 10.9 | 2.1 | 0.1 | 2.8 | 0.1 | 0.01 | 69 | 0.02 | 0.01 | 15.3 | 190 | 2800 |
| Com. Ex. 2 | 0.8 | 3.2 | 0.01 | 1.1 | 0.1 | 0.01 | Remainder | 0.005 | 0.01 | 19.7 | 140 | 140 |
| Com. Ex. 3 | 32.1 | 2.2 | 0.1 | 5.5 | 0.1 | 0.01 | Remainder | 0.08 | 0.01 | 0.01 | 140 | 130 |
| Com. Ex. 4 | 60.5 | 23.1 | 0.1 | 10.5 | 0.1 | 0.01 | Remainder | 0.19 | 0.01 | less than detection limit (less than 1 ppb) | 116 | 130 |
| Com. Ex. 5 | 0.9 | 1.1 | 0.01 | 0.8 | 0 | 0.01 | Remainder | 0 | 0.01 | 0.4 | 140 | 130 |
| Com. Ex. 6 | 2.9 | 1.5 | 0.01 | 2.2 | 0.01 | 0.01 | Remainder | 0.01 | 0.01 | 0.0003 | 136 | 140 |
| Com. Ex. 7 | 8.4 | 4.9 | 0.01 | 6.5 | 0.1 | 0.01 | Remainder | 0.0003 | 0.01 | less than detection limit (less than 1 ppb) | 150 | 200 |
| Com. Ex. 8 | 95 ppb | 0.2 | 23 ppb | 18 ppm | 0 | 0 | Remainder | 0 | 0 | less than detection limit (less than 1 ppb) | 137 | 80 |
| Com. Ex. 9 | 6 ppb | 0.05 | 4 ppb | 5 ppm | 0 | 0 | Remainder | 0 | 0.01 | 0.0002 | 160 | 230 |
| Com. Ex. 10 | Remainder | 1.1 | 0.01 | 9.7 | 0.01 | 0.01 | 2.1 | 0.05 | 0 | less than detection limit (less than 1 ppb) | 80 | 250 |
| Com. Ex. 11 | 1 ppb | 0.05 | 0.7 ppb | 9 ppm | less than detection limit (less than 1 ppm) | less than detection limit (less than 1 ppm) | Remainder | 0.8 ppm | 0.01 | less than detection limit (less than 1 ppb) | 138 | 80 |
| Com. Ex. 12 | 3 | 1.5 | 0.01 | 2 | 0.01 | 0.01 | Remainder | 0.01 | 0.01 | 0.0003 | 136 | 140 |

TABLE 63

| | MeI wt % | Water wt % | HI wt % | MA wt % | MeOH wt % | DME wt % | Ac wt % | AD wt % | PA wt % | LiI wt % | Temperature ° C. | Pressure KPG |
|---|---|---|---|---|---|---|---|---|---|---|---|---|
| Ex. 1 | 10.5 | 2.2 | 0.1 | 3 | 0.1 | 0.01 | Remainder | 0.02 | 0.01 | 14.9 | 190 | 2800 |
| Ex. 2 | 0.9 | 3 | 0.01 | 1.2 | 0.1 | 0.01 | Remainder | 0.004 | 0.01 | 20.1 | 140 | 140 |
| Ex. 3 | 32.8 | 1.9 | 0.1 | 6.1 | 0.1 | 0.01 | Remainder | 0.09 | 0.01 | 0.01 | 140 | 130 |
| Ex. 4 | 59.9 | 22.8 | 0.1 | 11 | 0.1 | 0.01 | Remainder | 0.2 | 0.01 | less than detection limit (less than 1 ppb) | 116 | 130 |
| Ex. 5 | 1.1 | 0.9 | 0.01 | 1.1 | 0 | 0.01 | Remainder | 0 | 0.01 | 0.4 | 140 | 130 |
| Ex. 6 | 3.2 | 1.8 | 0.01 | 2 | 0.01 | 0.01 | Remainder | 0.008 | 0.01 | 0.0003 | 136 | 140 |
| Ex. 7 | 7.9 | 4.7 | 0.01 | 6 | 0.1 | 0.01 | Remainder | 0.0003 | 0.01 | less than detection limit (less than 1 ppb) | 150 | 200 |
| Ex. 8 | 102 ppb | 0.18 | 19 ppb | 23 ppm | 0 | 0 | Remainder | 0 | 0 | less than detection limit (less than 1 ppb) | 137 | 80 |
| Ex. 9 | 5 ppb | 0.04 | 6 ppb | 5 ppm | 0 | 0 | Remainder | 0 | 0.01 | 0.0002 | 160 | 230 |
| Ex. 10 | Remainder | 0.8 | 0.01 | 10.1 | 0.008 | 0.01 | 1.9 | 0.08 | 0 | less than detection limit (less than 1 ppb) | 80 | 250 |
| Ex. 11 | 2.9 | 1.3 | 0.01 | 1.8 | 0.011 | 0.01 | Remainder | 0.009 | 0.01 | 0.0003 | 136 | 140 |
| Ex. 12 | 3.2 | 1.6 | 0.01 | 1.9 | 0.008 | 0.01 | Remainder | 0.01 | 0.01 | 0.0003 | 136 | 140 |
| Ex. 13 | 3.1 | 1.4 | 0.01 | 2.1 | 0.012 | 0.01 | Remainder | 0.011 | 0.01 | 0.0003 | 136 | 140 |
| Ex. 14 | 2.8 | 1.5 | 0.01 | 2 | 0.01 | 0.01 | Remainder | 0.008 | 0.01 | 0.0003 | 136 | 140 |
| Ex. 15 | 3.3 | 1.6 | 0.01 | 2 | 0.007 | 0.01 | Remainder | 0.011 | 0.01 | 0.0003 | 136 | 140 |
| Ex. 16 | 3 | 1.2 | 0.01 | 2.1 | 0.09 | 0.01 | Remainder | 0.008 | 0.01 | 0.0003 | 136 | 140 |
| Ex. 17 | 3.3 | 1.5 | 0.01 | 1.9 | 0.012 | 0.01 | Remainder | 0.012 | 0.01 | 0.0003 | 136 | 140 |
| Ex. 18 | 0.9 ppb | 0.05 | 0.8 ppb | 8 ppm | less than detection limit (less than 1 ppm) | less than detection limit (less than 1 ppm) | Remainder | 1 ppm | 0.01 | less than detection limit (less than 1 ppb) | 138 | 80 |
| Ex. 19 | 1.1 ppb | 0.05 | 0.9 ppb | 7 ppm | less than detection limit (less than 1 ppm) | less than detection limit (less than 1 ppm) | Remainder | 1.1 ppm | 0.01 | less than detection limit (less than 1 ppb) | 138 | 80 |

TABLE 64

| | H₂ vol % | CO vol % | CO₂ vol % | CH₄ vol % | N₂ vol % | O₂ vol % | H₂ kPa | CO kPa | CO₂ kPa | CH₄ kPa | N₂ kPa | O₂ kPa |
|---|---|---|---|---|---|---|---|---|---|---|---|---|
| Com. Ex. 1 | 0 | 93 | 0 | 0 | 0 | 7 | 0 | 94 | 0 | 0 | 0 | 7.09 |
| Com. Ex. 2 | 0 | 93 | 0 | 0 | 0 | 7 | 0 | 94 | 0 | 0 | 0 | 7.09 |
| Com. Ex. 3 | 0 | 93 | 0 | 0 | 0 | 7 | 0 | 94 | 0 | 0 | 0 | 7.09 |
| Com. Ex. 4 | 0 | 93 | 0 | 0 | 0 | 7 | 0 | 94 | 0 | 0 | 0 | 7.09 |
| Com. Ex. 5 | 0 | 93 | 0 | 0 | 0 | 7 | 0 | 94 | 0 | 0 | 0 | 7.09 |
| Com. Ex. 6 | 0 | 93 | 0 | 0 | 0 | 7 | 0 | 94 | 0 | 0 | 0 | 7.09 |
| Com. Ex. 7 | 0 | 93 | 0 | 0 | 0 | 7 | 0 | 94 | 0 | 0 | 0 | 7.09 |
| Com. Ex. 8 | 0 | 93 | 0 | 0 | 0 | 7 | 0 | 94 | 0 | 0 | 0 | 7.09 |
| Com. Ex. 9 | 0 | 93 | 0 | 0 | 0 | 7 | 0 | 94 | 0 | 0 | 0 | 7.09 |
| Com. Ex. 10 | 0 | 93 | 0 | 0 | 0 | 7 | 0 | 94 | 0 | 0 | 0 | 7.09 |
| Com. Ex. 11 | 0 | 93 | 0 | 0 | 0 | 7 | 0 | 94 | 0 | 0 | 0 | 7.09 |
| Com. Ex. 12 | 0 | 0 | 0 | 0 | 93 | 7 | 0 | 0 | 0 | 0 | 94 | 7.09 |
| Ex. 1 | 0 | Remainder | 0 | 0 | 0 | 0.010 | 0 | 101 | 0 | 0 | 0 | 0.01 |
| Ex. 2 | 0 | Remainder | 0 | 0 | 0 | 0.010 | 0 | 101 | 0 | 0 | 0 | 0.01 |
| Ex. 3 | 0 | Remainder | 0 | 0 | 0 | 0.010 | 0 | 101 | 0 | 0 | 0 | 0.01 |
| Ex. 4 | 0 | Remainder | 0 | 0 | 0 | 0.010 | 0 | 101 | 0 | 0 | 0 | 0.01 |
| Ex. 5 | 0 | Remainder | 0 | 0 | 0 | 0.010 | 0 | 101 | 0 | 0 | 0 | 0.01 |
| Ex. 6 | 0 | Remainder | 0 | 0 | 0 | 0.010 | 0 | 101 | 0 | 0 | 0 | 0.01 |
| Ex. 7 | 0 | Remainder | 0 | 0 | 0 | 0.010 | 0 | 101 | 0 | 0 | 0 | 0.01 |
| Ex. 8 | 0 | Remainder | 0 | 0 | 0 | 0.010 | 0 | 101 | 0 | 0 | 0 | 0.01 |
| Ex. 9 | 0 | Remainder | 0 | 0 | 0 | 0.010 | 0 | 101 | 0 | 0 | 0 | 0.01 |
| Ex. 10 | 0 | Remainder | 0 | 0 | 0 | 0.010 | 0 | 101 | 0 | 0 | 0 | 0.01 |
| Ex. 11 | 0 | 95 | 0 | 0 | 0 | 5 | 0 | 96 | 0 | 0 | 0 | 5.07 |
| Ex. 12 | 0 | 99 | 0 | 0 | 0 | 1 | 0 | 100 | 0 | 0 | 0 | 1.01 |
| Ex. 13 | 0 | Remainder | 0 | 0 | 0 | 0.00010 | 0 | 101 | 0 | 0 | 0 | 0.00 |
| Ex. 14 | 0 | 0 | 0 | 0 | Remainder | 0.10 | 0 | 0 | 0 | 0 | 101 | 0.10 |
| Ex. 15 | 0 | 0 | 0 | 0 | Remainder | 0.010 | 0 | 0 | 0 | 0 | 101 | 0.01 |
| Ex. 16 | 0 | 0 | 0 | 0 | Remainder | 0.0010 | 0 | 0 | 0 | 0 | 101 | 0.001 |
| Ex. 17 | 2 | Remainder | 15 | 7 | 8 | 0.010 | 2 | 69 | 15 | 7 | 8 | 0.00 |
| Ex. 18 | 0 | Remainder | 0 | 0 | 0 | 0.00010 | 0 | 101 | 0 | 0 | 0 | 0.00 |
| Ex. 19 | 0 | Remainder | 0 | 0 | 0 | 0.000010 | 0 | 101 | 0 | 0 | 0 | 0.00 |

TABLE 65

| | | Corrosion test results | | | | | | | |
|---|---|---|---|---|---|---|---|---|---|
| | | Zr | | HB2 | | HC276 | | SUS316 | |
| | | mm/Y | Partial corrosion | mm/Y | Partial corrosion | mm/Y | Partial corrosion | mm/Y | Partial corrosion | APHA |
| Com. Ex. 1 | | 0.000 | none | 0.1 | present | — | — | — | — | 500< |
| Com. Ex. 2 | | 0.000 | none | 0.1 | present | — | — | — | — | 500< |
| Com. Ex. 3 | | 0.000 | none | 0.05 | present | 0.02 | present | 0.06 | none | 500< |
| Com. Ex. 4 | | 0.000 | none | 0.08 | present | 0.027 | present | 0.09 | none | 500< |
| Com. Ex. 5 | | 0.000 | none | 0.12 | present | 0.02 | present | 0.11 | none | 500< |
| Com. Ex. 6 | | 0.000 | none | 0.15 | present | 0.12 | present | — | — | 500< |
| Com. Ex. 7 | | 0.000 | none | 0.19 | present | 0.28 | present | — | — | 500< |
| Com. Ex. 8 | | 0.000 | none | 0.05 | present | 0.03 | none | 0.19 | none | 80 |
| Com. Ex. 9 | | 0.000 | none | 0.09 | present | 0.02 | present | 0.08 | present | 90 |
| Com. Ex. 10 | | 0.000 | none | 0.04 | present | 0.03 | present | 0.01 | present | 500< |
| Com. Ex. 11 | | 0.000 | none | 0.08 | present | 0.03 | present | 0.02 | — | 70 |
| Com. Ex. 12 | | 0.000 | none | 0.29 | present | 0.3 | present | — | — | 500< |
| Com. Ex. 13 | Feed plate | 0.000 | none | 0.05 | present | 0.02 | present | 0.09 | none | 500< |
| | Upper part of column | 0.000 | none | 0.06 | present | 0.01 | present | 0.06 | none | |
| Com. Ex. 14 | 2nd plate from bottom | 0.000 | none | 0.17 | present | 0.21 | present | — | — | 500< |
| | Upper part of column | 0.000 | none | 0.09 | present | 0.2 | present | — | — | |

TABLE 66

| | Corrosion test results | | | | | | | | |
|---|---|---|---|---|---|---|---|---|---|
| | Zr | | HB2 | | HC276 | | SUS316 | | |
| | mm/Y | Partial corrosion | mm/Y | Partial corrosion | mm/Y | Partial corrosion | mm/Y | Partial corrosion | APHA |
| Ex. 1 | 0.000 | none | 0.01 | none | — | — | — | — | 60 |
| Ex. 2 | 0.000 | none | 0.001 | none | — | — | — | — | 50 |

TABLE 66-continued

|  |  | Corrosion test results | | | | | | | |
|---|---|---|---|---|---|---|---|---|---|
|  |  | Zr | | HB2 | | HC276 | | SUS316 | |
|  |  | mm/Y | Partial corrosion | mm/Y | Partial corrosion | mm/Y | Partial corrosion | mm/Y | Partial corrosion | APHA |
| Ex. 3 |  | 0.000 | none | 0.005 | none | 0.01 | none | 0.06 | none | 50 |
| Ex. 4 |  | 0.000 | none | 0.015 | none | 0.025 | none | 0.10 | none | 25 |
| Ex. 5 |  | 0.000 | none | 0.01 | none | 0.02 | none | 0.10 | none | 25 |
| Ex. 6 |  | 0.000 | none | 0.03 | none | 0.09 | none | — | — | 25 |
| Ex. 7 |  | 0.000 | none | 0.07 | none | 0.25 | none | — | — | 35 |
| Ex. 8 |  | 0.000 | none | 0.001 | none | 0.01 | none | 0.05 | none | 10 |
| Ex. 9 |  | 0.000 | none | 0.000 | none | 0.005 | none | 0.03 | none | 10 |
| Ex. 10 |  | 0.000 | none | 0.001 | none | 0.02 | none | 0.13 | none | 40 |
| Ex. 11 |  | 0.000 | none | 0.08 | none | 0.19 | none | — | — | 50 |
| Ex. 12 |  | 0.000 | none | 0.05 | none | 0.11 | none | — | — | 40 |
| Ex. 13 |  | 0.000 | none | 0.03 | none | 0.09 | none | — | — | 20 |
| Ex. 14 |  | 0.000 | none | 0.06 | none | 0.1 | none | — | — | 40 |
| Ex. 15 |  | 0.000 | none | 0.04 | none | 0.09 | none | — | — | 30 |
| Ex. 16 |  | 0.000 | none | 0.03 | none | 0.10 | none | — | — | 25 |
| Ex. 17 |  | 0.000 | none | 0.03 | none | 0.11 | none | — | — | 35 |
| Ex. 18 |  | 0.000 | none | 0.000 | none | 0.000 | none | 0.05 | — | 5 |
| Ex. 19 |  | 0.000 | none | 0.000 | none | 0.000 | none | 0.04 | — | 5 |
| Ex. 20 | Feed plate | 0.000 | none | 0.005 | none | 0.02 | none | — | — | 40 |
|  | Upper part of column | 0.000 | none | 0.002 | none | 0.01 | none | — | — |  |
| Ex. 21 | 2nd plate from bottom | 0.000 | none | 0.01 | none | 0.19 | none | — | — | 10 |
|  | Upper part of column | 0.000 | none | 0.009 | none | 0.18 | none | — | — |  |
| Ex. 22 | 2nd plate from bottom | 0.000 | none | 0.02 | none | 0.02 | none | 0.07 | — | 80 |
|  | Upper part of column | 0.000 | none | 0.03 | none | 0.01 | none | 0.06 | — |  |

From the results shown in Tables 62 to 66, the following are seen.

Carbon monoxide CO reduces the concentration of oxygen by the reduction reaction: $CO + \tfrac{1}{2} O_2 \rightarrow CO_2$ to form what is called a reducing atmosphere. However, a high concentration of oxygen may not form a reducing atmosphere in some cases. From the comparison of Comparative Examples 1 to 11 with Examples 1 to 11, different in the liquid composition, under the condition of the oxygen concentration of 7 vol % in Comparative Examples, the test piece HB2, free from Cr and weak under an oxidizing atmosphere, had an increased corrosion rate. For the SUS316 material, the corrosion rate in Comparative Example 11 tended to slightly decrease compared with that in each of Examples 18 and 19. Such a tendency seems to be one of general characteristics of SUS, and the corrosion rate may tend to be increased adversely in an excessively high reducing atmosphere. Thus, it was found that, according to the condition, the presence of some oxygen in the process sometimes reduced the corrosion.

Moreover, in the test piece HB2 or other materials in Comparative Examples, pitting corrosion or spot corrosion was often observed which seems to be the influence of iodine $I_2$ produced by the reaction: $2HI + \tfrac{1}{2} O_2 \rightarrow I_2 + H_2O$ or other reactions. In the test pieces SUS316 and HC276 containing Cr, under a condition of not a very high oxygen concentration some increase in corrosion rate was observed although such an increase did not lead the test pieces to excessive corrosion.

Further, the solution after the corrosion test had an apparently large APHA value compared with the solution before the corrosion test to become dark to reddish brown color peculiar to iodine. This coloring is caused by production of iodine $I_2$. The APHA value shown in Tables is up to 500. In this regard, in experimental examples in which the oxygen concentration was high and iodine $I_2$ was produced at a high concentration, the solution had little or no transparency and colored to a degree not expressed by APHA. This event shows that iodine $I_2$ flows out to the succeeding step in a process having a high oxygen concentration, resulting in the acceleration of corrosion in the succeeding step and the coloring or the increase in a total iodine concentration due to contamination with iodine in a product.

Comparative Example 12 is an experiment carried out under a nitrogen atmosphere which has no reaction reducing the concentration of oxygen $O_2$, different from a carbon monoxide CO. Thus, the test pieces (particularly, test piece HB2) had a significantly increased corrosion rate compared with Example 6.

In Example 11, the concentration of oxygen was reduced to half (1 vol %) of that in Comparative Example 11. Although there is still an adverse influence of oxygen on the corrosion test and the coloring, these influences are considerably small compared with Comparative Example. Thus, the above oxygen concentration is not an unacceptable concentration.

In Example 12, the concentration of oxygen was reduced to ¼ (0.5 vol %) of that in Comparative Example 11. Although there is still an adverse influence of oxygen on the corrosion test and the coloring, these influences are considerably small compared with Comparative Example. Thus, the above oxygen concentration is also not an unacceptable concentration.

In Example 13, the concentration of oxygen $O_2$ was reduced as low as possible as long as the concentration was measurable. The results of Example 13 are substantially equivalent to those of Example 6, in which the concentration of oxygen was 0.01 vol %. The results show that the concentration of oxygen reduced to some degree or extent has little or no adverse influence and show substantially equivalent behavior therebetween.

Incidentally, in Examples 18 and 19, the corrosion rate of the test piece SUS316 was slightly high compared with that in Comparative Example 11. The reason why is as follows. SUS316 sometimes tend to increase in corrosion rate under a high reducing atmosphere, and thus, under less or no oxygen such as the condition of Examples 18 and 19, corrosion is accelerated. Since this tendency seems to be observed markedly under a lower concentration of oxygen, it is not advisable, particularly for stainless steel (SUS)-based material, to reduce the concentration of oxygen to sufficiently near zero (for example, 1 vol ppt, 1 vol ppb) under a reducing condition in the presence of carbon monoxide CO. However, such a degree of corrosion was not unacceptable level at all. Incidentally, under such a condition, impurities have little or no iodine contents and the oxygen concentration is extremely low, and thus less- or no-colored product acetic acid is obtained.

In Example 14, the concentration of oxygen was reduced to 0.1 vol % under a nitrogen gas $N_2$ atmosphere. According to Example 14, although the test piece HB2 is slightly corroded which results in slight coloring, the test piece HB2 has a reduced corrosion compared with Example 11, and the concentration of oxygen is not an unacceptable concentration.

In Examples 15 and 16, the concentration of oxygen was further reduced under a nitrogen gas $N_2$ atmosphere. In Examples 15 and 16, including Example 13, the degree of the corrosion is not very different from the degree of the corrosion under a carbon monoxide CO atmosphere. Under a lower concentration of oxygen, the corrosion rate and the coloring were substantially the same level as those under a carbon monoxide CO atmosphere.

Example 17 is an experiment using a different feed gas. As compared with Example 6, it is found that different feed gases, each having sufficient carbon monoxide CO gas and the same concentration of oxygen, provide substantially the same corrosion rate and APHA.

From the comparison of Comparative Example 13 with Example 20, when carbon monoxide fed to the reactor has a high concentration of oxygen, the test piece, particularly the test piece HB2 weak in oxygen, is corroded and the side-cut liquid has a high degree of coloring (large APHA value). Moreover, in Comparative Example 13, due to a considerably high concentration of oxygen in the upper part of the column, the test piece HB2 disposed at the upper part of the first distillation column has a large corrosion rate in spite of a low temperature thereof, compared with the test piece HB2 disposed at the feed plate. The test piece HB2 usually shows a high corrosion resistance under a low concentration of oxygen. Thus, the corrosion rate of the test piece HB2 under a low oxygen concentration condition as Example 20 is small compared with that under an overall high concentration of oxygen, while the corrosion rate test piece HB2 at the feed plate having a higher temperature is larger than that at the upper part of the column having a lower temperature.

Comparative Example 14 and Example 21 had the same tendency as the Comparative Example 13 and Example 20, although the feed composition is different.

Generally, the price of the material is low in this order of Zr>HB2>HC>SUS.

Considering the price, the material can be selected on the basis of the corrosion rate as the following standards, although the thickness of the material, the frequency of renovation, or other factors are influenced.

Corrosion rate of 0.05 mm/Y or less: suitable for use
0.05 to 0.1 mm/Y: usable level
0.1 mm/Y to 0.2 mm/Y: usable depending on conditions
0.2 mm/Y or more: unusable

INDUSTRIAL APPLICABILITY

The present invention effectively prevents the corrosion of the process unit and/or line and is significantly useful as a process for stably producing high-quality acetic acid.

REFERENCE SIGNS LIST (1) . . . Reactor
(2) . . . Evaporator
(3) . . . First distillation column
(5) . . . Second distillation column (Dehydration column)
(6) . . . Third distillation column (Heavy end column)
(7) . . . Fourth distillation column (Purification column)
(8) . . . Ion exchange tank
(10) . . . Decanter
(11) . . . Fifth distillation column (First aldehyde-removing column)
(12) . . . Sixth distillation column (Water extractive distillation column)
(13) . . . Seventh distillation column (Second aldehyde-removing column)
(14) . . . Eighth distillation column (Alkane-removing column)
(16) . . . High-pressure absorption column
(17) . . . Low-pressure absorption column
(18) . . . Diffusion column

The invention claimed is:
1. A process for producing acetic acid, comprising:
(1) allowing methanol to carbonylation react with carbon monoxide in the presence of a catalyst system, acetic acid, methyl acetate, and water, wherein the catalyst system comprises a metal catalyst, an ionic metal iodide, and methyl iodide;
(2) separating the reaction mixture into a volatile phase and a less-volatile phase;
(3) distilling the volatile phase to form a first overhead and an acetic acid stream, wherein the first overhead is rich in at least one lower boiling component selected from the group consisting of methyl iodide and acetaldehyde, and the acetic acid stream is rich in acetic acid; and
at least one step group selected from the group consisting of the following step groups (4), (9), and (15):
(4) a purification step group for obtaining purified acetic acid from the acetic acid stream;
(9) a separation step group for separating at least acetaldehyde from the first overhead; and
(15) an off-gas treatment step group for absorption-treating an off-gas from the process with an absorption solvent and forming a carbon monoxide-rich stream and an acetic acid-rich stream;
wherein the process is operated under at least one selected from the group consisting of the following conditions (a) and (b) to produce a product acetic acid having an iodine ($I_2$) concentration of not more than 10 ppb by weight, or a hydrogen iodide concentration of not more than 20 ppb by weight, or an iodine ($I_2$) concentration of not more than 10 ppb by weight and a hydrogen iodide concentration of not more than 20 ppb by weight:
  (a) the concentration of oxygen in a gaseous phase of the process is less than 7% by volume,
  (b) the concentration of oxygen in a liquid phase of the process is less than $7 \times 10^{-5}$ g/g.

2. The process according to claim 1, wherein the gaseous phase of the process contains at least one member selected from the group consisting of methyl iodide and hydrogen iodide.

3. The process according to claim 1, wherein the gaseous phase of the process further contains at least one member selected from the group consisting of acetic acid, methyl acetate, methanol, water, acetaldehyde, a by-product derived from acetaldehyde, and a dialkyl ether; the by-product contains at least one member selected from the group consisting of an alkyl iodide with 2 or more carbon atoms, an alkanal with 4 or more carbon atoms, an alkanecarboxylic acid with 3 or more carbon atoms, an alkane, and a ketone; and the dialkyl ether contains at least dimethyl ether.

4. The process according to claim 1, wherein, in at least one process stream selected from the group consisting of a stream of a process unit and a stream of a process line, the process is operated under at least one selected from the group consisting of the following conditions (a-1) and (b-1):
  (a-1) the concentration of oxygen in the gaseous phase is 5% by volume or less,
  (b-1) the concentration of oxygen in the liquid phase is $2 \times 10^{-5}$ g/g or less.

5. The process according to claim 1, wherein, in at least one process stream selected from the group consisting of a stream of a process unit and a stream of a process line, a ratio of oxygen relative to carbon monoxide in each of the gaseous phase and the liquid phase is 2% by volume or less.

6. The process according to claim 1, wherein, in at least one process stream selected from the group consisting of a stream of a process unit and a stream of a process line, a ratio of oxygen relative to carbon monoxide in each of the gaseous phase and the liquid phase is 1% by volume or less.

7. The process according to claim 1, wherein at least one component selected from the group consisting of an oxygen-containing gas, an oxygen-containing compound, and an oxygen generator is introduced to the process; and in at least one process stream selected from the group consisting of a stream of a process unit and a stream of a process line, the concentration of oxygen in the gaseous phase is 1 ppt by volume or more, and/or the concentration of oxygen in the liquid phase is $0.1 \times 10^{-9}$ g/g or more.

8. The process according to claim 1, wherein the concentration of oxygen in the gaseous phase is 1 ppb by volume or more.

9. The process according to claim 1, wherein a concentration of oxygen in at least one process stream selected from the group consisting of the gaseous phase and the liquid phase is 0.25 mol or less relative to 1 mol of a total amount of hydrogen iodide and methyl iodide.

10. The process according to claim 1, wherein the purification step group (4) comprises at least (5) a dehydration step among the following steps (5) to (8):
  (5) dehydrating the acetic acid stream;
  (6) removing a higher boiling component from the acetic acid stream;
  (7) further purification-distilling an acetic acid stream from the step (6); and
  (8) ion-exchange separating an iodine compound from an acetic acid stream from the step (7).

11. The process according to claim 1, wherein the separation step group (9) comprises at least steps (10) to (13) among the following steps (10) to (14):
  (10) condensing the first overhead to form two liquid phases with an upper phase and a lower phase;
  (11) forming a fifth overhead from the upper phase, the lower phase, or both, wherein the fifth overhead is rich in acetaldehyde and methyl iodide;
  (12) extracting acetaldehyde from the fifth overhead to form an extract and a raffinate, wherein the extract is rich in acetaldehyde and the raffinate is rich in methyl iodide;
  (13) separating an aldehyde from the extract, the raffinate, or both; and
  (14) separating an alkane from the upper phase, the lower phase, or both.

12. The process according to claim 1, wherein the off-gas treatment step group (15) comprises at least one absorption step selected from the group consisting of steps (16) and (17) among the following steps (16) to (18):
  (16) absorbing the off-gas to an absorption solvent at a high pressure;
  (17) absorbing the off-gas to an absorption solvent at a low pressure; and
  (18) diffusing a gaseous component absorbed in the absorption steps (16) and (17).

13. The process according to claim 1, wherein the gaseous phase of the process comprises an off-gas from the process.

14. The process according to claim 2, wherein the product acetic acid has a hydrogen iodide concentration of not more than 10 ppb by weight.

15. A method for reducing formation of iodine in a process, comprising:
  (1) allowing methanol to carbonylation react with carbon monoxide in the presence of a catalyst system, acetic acid, methyl acetate, and water, wherein the catalyst system comprises a metal catalyst, an ionic metal iodide, and methyl iodide;
  (2) separating the reaction mixture into a volatile phase and a less-volatile phase;
  (3) distilling the volatile phase to form a first overhead and an acetic acid stream, wherein the first overhead is rich in at least one lower boiling component selected from the group consisting of methyl iodide and acetaldehyde, and the acetic acid stream is rich in acetic acid; and
at least one step group selected from the group consisting of the following step groups (4), (9), and (15):
  (4) a purification step group for obtaining purified acetic acid from the acetic acid stream;
  (9) a separation step group for separating at least acetaldehyde from the first overhead; and
  (15) an off-gas treatment step group for absorption-treating an off-gas from the process with an absorption solvent and forming a carbon monoxide-rich stream and an acetic acid-rich stream;
wherein the process is operated under at least one selected from the group consisting of the following conditions (a) and (b) to produce a product acetic acid having an iodine ($I_2$) concentration of not more than 10 ppb by weight, or a hydrogen iodide concentration of not more than 20 ppb by weight, or an iodine ($I_2$) concentration of not more than 10 ppb by weight and a hydrogen iodide concentration of not more than 20 ppb by weight:
  (a) the concentration of oxygen in a gaseous phase portion of the process is less than 7% by volume, (b) the concentration of oxygen in a liquid stream of the process is less than $7 \times 10^{-5}$ g/g.

16. The method according to claim 15, wherein the product acetic acid has a hydrogen iodide concentration of not more than 10 ppb by weight.

* * * * *